US008921567B2

(12) United States Patent
Körber et al.

(10) Patent No.: US 8,921,567 B2
(45) Date of Patent: Dec. 30, 2014

(54) PROCESS FOR PREPARING N-SUBSTITUTED 1H-PYRAZOLE-5-CARBONYLCHLORIDE COMPOUNDS

(75) Inventors: Karsten Körber, Eppelheim (DE); Prashant Deshmukh, Mannheim (DE); Florian Kaiser, Mannheim (DE); Michael Rack, Eppelheim (DE); Timo Frassetto, Mannheim (DE); Gemma Veitch, Basel (CH); Markus Kordes, Bobenheim-Roxheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/235,556

(22) PCT Filed: Aug. 10, 2012

(86) PCT No.: PCT/EP2012/065648
§ 371 (c)(1),
(2), (4) Date: Jan. 28, 2014

(87) PCT Pub. No.: WO2013/024007
PCT Pub. Date: Feb. 21, 2013

(65) Prior Publication Data
US 2014/0163234 A1   Jun. 12, 2014

Related U.S. Application Data

(60) Provisional application No. 61/522,746, filed on Aug. 12, 2011.

(30) Foreign Application Priority Data

Aug. 12, 2011   (EP) .................................... 11177494

(51) Int. Cl.
*C07D 401/04*   (2006.01)
(52) U.S. Cl.
CPC ................................... *C07D 401/04* (2013.01)
USPC ..................... 546/278.4; 546/279.1
(58) Field of Classification Search
None
See application file for complete search history.

(56) References Cited

U.S. PATENT DOCUMENTS 7,339,057 B2 *   3/2008   Taylor ............................. 544/92

FOREIGN PATENT DOCUMENTS

| EP | 1265850 | 1/2007 |
|----|---------|--------|
| EP | 2 143 720 | 1/2010 |
| WO | WO 01/70671 | 9/2001 |
| WO | WO 02/070483 | 9/2002 |
| WO | WO 03/015518 | 2/2003 |
| WO | WO 03/015519 | 2/2003 |
| WO | WO 03/016300 | 2/2003 |
| WO | WO 03016284 | 2/2003 |
| WO | WO 03/024222 | 3/2003 |
| WO | WO 2006/000336 | 1/2006 |
| WO | WO 2006/068669 | 6/2006 |
| WO | WO 2007/006670 | 1/2007 |

(Continued)

OTHER PUBLICATIONS

Micetich et al., "The Sequential Lithiation of 1-Phenylpyrazoles", Heterocycles, vol. 23, No. 4, 1985, pp. 943-951.

(Continued)

*Primary Examiner* — Timothy R Rozof
(74) *Attorney, Agent, or Firm* — Brinks Gilson & Lione

(57) ABSTRACT

The present invention relates to a process for preparing an N-substituted 1H-pyrazole-5-carbonylchloride compound of the formula (I)

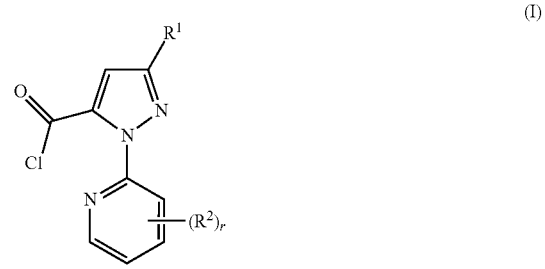

in which $R^1$ is hydrogen, halogen, cyano, $C_1$-$C_6$-alkyl, $C_1$-$C_6$-fluoroalkyl, $C_3$-$C_8$-cycloalkyl, $C_3$-$C_8$-fluorocycloalkyl, $C_2$-$C_6$-alkenyl, $C_2$-$C_6$-fluoroalkenyl, $C_1$-$C_6$-alkoxy, $C_1$-$C_6$-fluoroalkoxy, $C_1$-$C_4$-fluoroalkoxy-$C_1$-$C_4$-alkyl, phenyl and the like; each $R^2$ is independently selected from halogen, $C_1$-$C_6$-alkyl, $C_1$-$C_6$-fluoroalkyl, $C_3$-$C_8$-cycloalkyl, $C_3$-$C_8$-fluorocycloalkyl, $C_2$-$C_6$-alkenyl, $C_2$-$C_6$-fluoroalkenyl, $C_1$-$C_6$-alkoxy, phenyl and the like; r is 0, 1, 2, 3 or 4; comprising the steps of
i) deprotonating a compound of the formula (II)

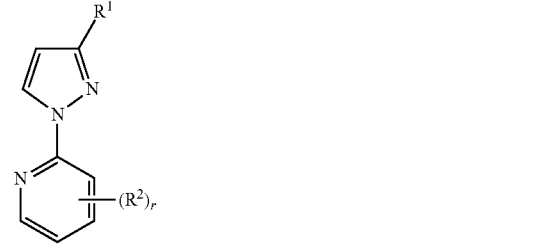

in which the variables $R^1$, $R^2$ and r are each as defined above,
with a base selected from lithium-organic base having a carbon or nitrogen bound lithium or with a magnesium-organic base having a carbon bound magnesium; and
ii) subjecting the product obtained in step (i) to a chlorocarbonylation by reacting it with a reagent selected from the group consisting of phosgene or a phosgene equivalent, to obtain a compound of formula (I).

17 Claims, No Drawings

(56) References Cited

FOREIGN PATENT DOCUMENTS

| WO | WO 2007/043677 | 4/2007 |
|---|---|---|
| WO | WO 2008/011131 | 1/2008 |
| WO | WO 2008/130021 | 10/2008 |
| WO | WO 2011/064188 | 6/2011 |
| WO | WO 2013/024007 | 2/2013 |
| WO | WO 2013/024008 | 2/2013 |
| WO | WO 2013/024009 | 2/2013 |
| WO | WO 2013/024010 | 2/2013 |
| WO | WO 2013/076092 | 5/2013 |

OTHER PUBLICATIONS

Caira, Mino R., "Crystalline Polymorphism of Organic Compounds", Topics in Current Chemistry, vol. 198, 1998, pp. 164-208.
International Search Report, PCT/EP2012/065648, filed Aug. 10, 2012.
International Preliminary Report on Patentability, PCT/EP2012/065648, filed Aug. 10, 2012.
Cho et al., "Synthesis of Pyrroloazepines. Facile Synthesis of 2-Sustituted Pyrrole Derivatives by the Phosgene Method", J. Heterocyclic Chem., vol. 34, No. 87, 1997, pp. 87-91.
Clark et al., "Synthesis of insecticidal fluorinated anthranilic diamides", Bioorganic & Medicinal Chemistry, vol. 16, 2008, pp. 3163-3170.
deGroot et al., "Synthesis and Photoisomerisation of 2,3.17,18,22-pentamethyl-10,23-dihydro-1,19-[21$H$,24$H$]-bilindione, an unsymmetrical bilirubin model compound", Journal of the Royal Netherlands Chemical Society, vol. 101, No. 6, 1982, pp. 219-223.
Gschwend et al., Organic Reactions, vol. 26, 1979, p. 26.
Lahm et al., "Insecticidal anthranilic diamides: A new class of potent ryanodine receptor activators", Bioorganic & Medicinal Chemistry Letters, vol. 15, 2005, pp. 4898-4906.
Lahm et al., "Rynaxypyr™: A new insecticidal anthranilic diamide that acts as a potent and selective ryanodine receptor activator", Bioorganic & Medicinal Chemistry Letters, vol. 17, 2007, pp. 6274-6279.
Liu et al., "Design, Synthesis and Insecticidal Evaluation of Novel Pyrazolecarboxamides Containing Cyano Substituted $N$-Pyridylpyrazole", Chin. J. Chem., vol. 28, 2010, pp. 1757-1760.
Purandare et al., "Pyrazole inhibitors of coactivator associated arginine methyltransferase 1 (CARM1)", Bioorganic & Medicinal Chemistry Letters, vol. 18, 2008, pp. 4438-4441.
Tertov et al., "Reactions of N-Substituted Diazoles and their Halo Derivatives with Naphthyllithium and Naphthylsodium", Khimiya Geterotsiklicheskikh Soedinenii, No. 3, 1975, pp. 392-395.
Mutule, Ilga, et al. "Arylzinc species by microwave assisted Gringnard formation—transmetallation sequence: application in the Negishi coupling", Tetrahedron, 2005, p. 11168-11176, vol. 61.
Gschwend, Heinz W., et al., "Heteroatom-Facilitated Lthiations", H.R. Organic Reactions, 1979, p. 1-111, vol. 26.

\* cited by examiner

PROCESS FOR PREPARING N-SUBSTITUTED 1H-PYRAZOLE-5-CARBONYLCHLORIDE COMPOUNDS

This application is a National Stage application of International Application No. PCT/EP2012/065648, filed Aug. 10, 2012, which claims the benefit of U.S. Provisional Application No. 61/522,746, filed Aug. 12, 2011, the entire contents of which are hereby incorporated herein by reference. This application also claims priority under 35 U.S.C. §119 to EP Patent Application No. 11177494.9, filed Aug. 12, 2011, the entire contents of which is hereby incorporated herein by reference.

The present invention relates to a process for preparing N-substituted 1H-pyrazole-5-carbonylchloride compounds. It also relates to the use of these acid chlorides for preparing anthranilamide derivatives that are useful pesticides.

N-substituted 1H-pyrazole-5-carbonylchloride compounds, in particular substituted 1-pyridin-2-yl-1H-pyrazole-5-carbonylchlorides are important precursors for anthranilamide derivates that carry a 1-pyridin-2-yl-1H-pyrazol-5-yl-carbonyl substituent at the aromatic amino group. Such compounds find use as pesticides, especially as insecticides, which are disclosed, for example, in WO 01/70671, WO 03/015518, WO 03/016284, WO 03/016300, WO 03/024222, WO 06/000336; WO 06/068669, WO 07/043677 and WO 08/130021.

For preparation of substituted 1-pyridin-2-yl-1H-pyrazole-5-carbonylchlorides, a process described in WO 07/043677 and WO 08/130021 has been found to be useful. It is based on the deprotonation of a 1-pyridin-2-yl-1H-pyrazole compound with either n-butyl lithium or lithium diisoproylamide, followed by reacting the resulting lithiated species with carbon dioxide to the corresponding carboxylic acid, which is subsequently chlorinated using a dehydrative chlorinating agent such as thionyl chloride or oxalyl chloride to give the corresponding acid chloride. Similar synthetic routes that all require the formation of the pyrazole-5-carboxylic acid as an intermediate are described for example in: Khimiya Geterotsiklicheskikh Soedinenii 1975, 3, 392-395; Heterocycles 1985, 23, 943-951; Bioorganic & Medicinal Chemistry Letters 2005, 15, 4898-4906; WO 06/000336; WO 06/068669; Bioorganic & Medicinal Chemistry Letters 2007, 17, 6274-6279; Bioorganic & Medicinal Chemistry 2008, 16, 3163-3170; Organic Reactions 1979, 26; Bioorganic & Medicinal Chemistry Letters 2008, 18, 4438-4441 and WO 08/011131.

However, these procedures of the prior art suffer from several limitations rendering them hardly suitable for industrial scale production. For instance, the application of the highly reactive organolithium bases, such as lithium butyllithium, phenyllithium or lithium diisopropylamide, for the deprotonation of pyrazoles represents a potentially hazardous step in the synthesis, in particular if performed on a large scale. Moreover, these organolithium bases are very expensive and require the very low reaction temperatures, which in itself already results in excessive energy costs. Additionally, a conversion of 1-pyridin-2-yl-1H-pyrazole compounds to the corresponding pyrozole-5-carboxylic acid chloride in less than the four steps required by the known procedures, would be highly desirable, as every synthetic step is time and energy consuming and leads to a loss of material.

It was an object of the present invention to provide processes for preparing N-substituted 1H-pyrazole-5-carbonylchloride compounds and for preparing pyrazolecarboxamides of anthranilamides derived therefrom. These processes should be simple to carry out, require 3 or less steps and be suitable for the industrial scale production. They should additionally be inexpensive and be based on selective reactions.

The object is achieved by the processes described in detail hereinafter.

A first aspect of the present invention relates to a process for preparing an N-substituted 1H-pyrazole-5-carbonylchloride compound of the formula (I)

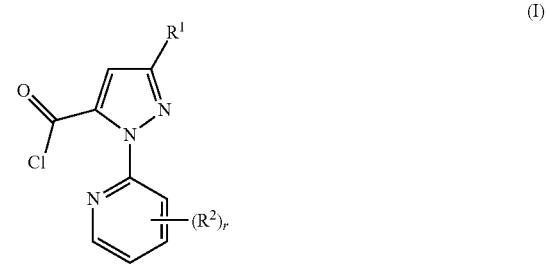

in which
R$^1$ is selected from hydrogen, halogen, cyano, —SF$_5$, C$_1$-C$_6$-alkyl, C$_1$-C$_6$-fluoroalkyl, CBrF$_2$, C$_3$-C$_8$-cycloalkyl, C$_3$-C$_8$-fluorocycloalkyl, C$_2$-C$_6$-alkenyl, C$_2$-C$_6$-fluoroalkenyl, wherein the six last mentioned radicals may be substituted by one or more radicals R$^a$; —Si(R$^f$)$_2$R$^g$, —OR$^b$, —SR$^b$, —S(O)$_m$R$^b$, —S(O)$_n$N(R$^c$)R$^d$, —N(R$^{c1}$)R$^{d1}$, phenyl which may be substituted by 1, 2, 3, 4 or 5 radicals R$^e$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and SO$_2$, as ring members, where the heterocyclic ring may be substituted by one or more radicals R$^e$;

each R$^2$ is independently selected from the group consisting of halogen, SF$_5$, C$_1$-C$_6$-alkyl, C$_1$-C$_6$-fluoroalkyl, C$_3$-C$_8$-cycloalkyl, C$_3$-C$_8$-fluorocycloalkyl, C$_2$-C$_6$-alkenyl, C$_2$-C$_6$-fluoroalkenyl, wherein the six last mentioned radicals may be substituted by one or more radicals R$^a$; —Si(R$^f$)$_2$R$^g$, —OR$^b$, —SR$^b$, —S(O)$_m$R$^b$, —S(O)$_n$N(R$^c$)R$^d$, —N(R$^{c1}$)R$^{d1}$, phenyl which may be substituted by 1, 2, 3, 4 or 5 radicals R$^e$, and a 3-, 4-, 5-, 6- or 7-membered saturated, partially unsaturated or completely unsaturated heterocyclic ring containing 1, 2 or 3 heteroatoms or heteroatom groups selected from N, O, S, NO, SO and SO$_2$, as ring members, where the heterocyclic ring may be substituted by one or more radicals R$^e$;

R$^a$ is selected from the group consisting SF$_5$, C$_1$-C$_6$-alkyl, C$_1$-C$_6$-fluoroalkyl, C$_1$-C$_6$-alkoxy-C$_1$-C$_6$-alkyl, C$_3$-C$_8$-cycloalkyl, C$_3$-C$_8$-fluorocycloalkyl, C$_2$-C$_6$-alkenyl, C$_2$-C$_6$-fluoroalkenyl, —Si(R$^f$)$_2$R$^g$, —OR$^b$, —SR$^b$, —S(O)$_m$R$^b$, —S(O)$_n$N(R$^c$)R$^d$, —N(R$^{c1}$)R$^{d1}$, phenyl which may be substituted by 1, 2, 3, 4 or 5 radicals R$^e$, and a 3-, 4-, 5-, 6- or 7-membered saturated, partially unsaturated or completely unsaturated heterocyclic ring containing 1, 2 or 3 heteroatoms or heteroatom groups selected from N, O, S, NO, SO and SO$_2$, as ring members, where the heterocyclic ring may be substituted by one or more radicals R$^e$;

or two geminally bound radicals R$^a$ together form a group selected from =CR$^h$R$^i$, =NR$^{c1}$, =NOR$^b$ and =NNR$^{c1}$;

or two radicals R$^a$, together with the carbon atoms to which they are bound, form a 3-, 4-, 5-, 6-, 7- or 8-membered saturated or partially unsaturated carbocyclic or heterocyclic ring containing 1, 2 or 3 heteroatoms or heteroatom groups selected from N, O, S, NO, SO and SO$_2$, as ring members;

wherein, in the case of more than one R$^a$, R$^a$ can be identical or different;

R$^b$ is selected from the group consisting of C$_1$-C$_6$-alkyl, C$_1$-C$_6$-fluoroalkyl, C$_2$-C$_6$-alkenyl, C$_2$-C$_6$-fluoroalkenyl, C$_3$-C$_8$-cycloalkyl, C$_3$-C$_8$-fluorocycloalkyl, wherein the six last mentioned radicals may optionally carry 1 or 2 radicals selected from C$_1$-C$_6$-alkoxy, C$_1$-C$_6$-fluoroalkoxy, C$_1$-C$_6$-alkylthio, C$_1$-C$_6$-fluoroalkylthio, C$_1$-C$_6$-alkylsulfinyl, C$_1$-C$_6$- fluoroalkylsulfinyl, $C_1$-$C_6$-alkylsulfonyl, $C_1$-$C_6$-fluoroalkylsulfonyl, —Si($R^f$)$_2R^g$, phenyl, benzyl, pyridyl and phenoxy, wherein the four last mentioned radicals may be unsubstituted, partially or fully halogenated and/or may carry 1, 2 or 3 substituents selected from the group consisting of $C_1$-$C_6$-alkyl, $C_1$-$C_6$-fluoroalkyl, $C_1$-$C_6$-alkoxy and $C_1$-$C_6$-fluoroalkoxy;

wherein, in the case of more than one $R^b$, $R^b$ can be identical or different;

$R^c$, $R^d$ are, independently from one another and independently of each occurrence, selected from the group consisting of cyano, $C_1$-$C_6$-alkyl, $C_1$-$C_6$-fluoroalkyl, $C_2$-$C_6$-alkenyl, $C_2$-$C_6$-fluoroalkenyl, $C_3$-$C_8$-cycloalkyl, $C_3$-$C_8$-fluorocycloalkyl, wherein the six last mentioned radicals may optionally carry 1 or 2 radicals selected from $C_1$-$C_6$-alkoxy, $C_1$-$C_6$-fluoroalkoxy, $C_1$-$C_6$-alkylthio, $C_1$-$C_6$-fluoroalkylthio, $C_1$-$C_6$-alkylsulfinyl, $C_1$-$C_6$-alkylsulfonyl, —Si($R^f$)$_2R^g$, phenyl, benzyl, pyridyl and phenoxy, wherein the four last mentioned radicals may be unsubstituted, partially or fully halogenated and/or may carry 1, 2 or 3 substituents selected from the group consisting of $C_1$-$C_6$-alkyl, $C_1$-$C_6$-fluoroalkyl, $C_1$-$C_6$-alkoxy and $C_1$-$C_6$-fluoroalkoxy;

or $R^c$ and $R^d$, together with the nitrogen atom to which they are bound, form a 3-, 4-, 5-, 6- or 7-membered saturated, partly unsaturated or completely unsaturated heterocyclic ring which may contain 1 or 2 further heteroatoms selected from N, O and S as ring members, where the heterocyclic ring may carry 1, 2, 3 or 4 substituents selected from halogen, $C_1$-$C_4$-alkyl, $C_1$-$C_4$-fluoroalkyl, $C_1$-$C_4$-alkoxy and $C_1$-$C_4$-fluoroalkoxy;

$R^{c1}$ is hydrogen or has one of the meanings given for $R^c$;

$R^{d1}$ is hydrogen or has one of the meanings given for $R^d$;

$R^e$ is selected from the group consisting of halogen, $C_1$-$C_6$-alkyl, $C_1$-$C_6$-fluoroalkyl, $C_2$-$C_6$-alkenyl, $C_2$-$C_6$-fluoroalkenyl, $C_3$-$C_8$-cycloalkyl, $C_3$-$C_8$-fluorocycloalkyl, where the six last mentioned radicals may optionally carry 1 or 2 radicals selected from $C_1$-$C_4$-alkoxy; $C_1$-$C_6$-alkoxy, $C_1$-$C_6$-fluoroalkoxy, $C_1$-$C_6$-alkylthio, $C_1$-$C_6$-fluoroalkylthio, $C_1$-$C_6$-alkylsulfinyl, $C_1$-$C_6$-fluoroalkylsulfinyl, $C_1$-$C_6$-alkylsulfonyl, $C_1$-$C_6$-fluoroalkylsulfonyl, —Si($R^f$)$_2R^g$, phenyl, benzyl, pyridyl and phenoxy, wherein the four last mentioned radicals may be unsubstituted, partially or fully halogenated and/or may carry 1, 2 or 3 substituents selected from the group consisting of $C_1$-$C_6$-alkyl, $C_1$-$C_6$-fluoroalkyl, $C_1$-$C_6$-alkoxy and $C_1$-$C_6$-fluoroalkoxy;

wherein, in the case of more than one $R^e$, $R^e$ can be identical or different;

$R^f$, $R^g$ are, independently of each other and independently of each occurrence, selected from the group consisting of $C_1$-$C_4$-alkyl, $C_3$-$C_6$-cycloalkyl, alkyl, phenyl and benzyl;

$R^h$, $R^i$ are, independently from one another and independently of each occurrence, selected from the group consisting of hydrogen, halogen, $SF_5$, $C_1$-$C_6$-alkyl, $C_1$-$C_6$-fluoroalkyl, $C_2$-$C_6$-alkenyl, $C_2$-$C_6$-fluoroalkenyl, $C_3$-$C_8$-cycloalkyl, $C_3$-$C_8$-fluorocycloalkyl, where the six last mentioned radicals may optionally carry 1 or 2 radicals selected from $C_1$-$C_4$-alkyl and $C_1$-$C_4$-fluoroalkyl; $C_1$-$C_6$-alkoxy, $C_1$-$C_6$-fluoroalkoxy, $C_1$-$C_6$-alkylthio, $C_1$-$C_6$-fluoroalkylthio, $C_1$-$C_6$-alkylsulfinyl, $C_1$-$C_6$-alkylsulfonyl, —Si($R^f$)$_2R^g$, phenyl, benzyl, pyridyl and phenoxy, wherein the four last mentioned radicals may be unsubstituted, partially or fully halogenated and/or may carry 1, 2 or 3 substituents selected from the group consisting of $C_1$-$C_6$-alkyl, $C_1$-$C_6$-fluoroalkyl, $C_1$-$C_6$-alkoxy, $C_1$-$C_6$-fluoroalkoxy, ($C_1$-$C_6$-alkoxy)carbonyl, ($C_1$-$C_6$-alkyl)amino and di-($C_1$-$C_6$-alkyl)amino;

m is 1 or 2, wherein, in the case of several occurrences, m may be identical or different;

n is 0, 1 or 2; wherein, in the case of several occurrences, n may be identical or different;

r is 0, 1, 2, 3 or 4;

comprising the steps of i) deprotonating a compound of the formula (II)

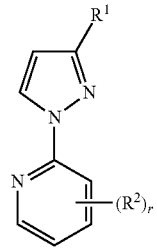

(II)

in which the variables $R^1$, $R^2$ and r are each as defined above, with a base selected from lithium-organic base having a carbon or nitrogen bound lithium or with a magnesium-organic base having a carbon bound magnesium; and ii) subjecting the product obtained in step (i) to a chlorocarbonylation by reacting it with a reagent selected from the group consisting of phosgene or a phosgene equivalent, to obtain a compound of formula (I).

The preceding process of the invention is associated with a series of advantages as it overcomes the aforementioned shortcomings of the prior art processes. For instance, the process according to the invention enables preparation of N-substituted 1H-pyrazole-5-carbonylchloride compounds of the formula (I) de facto in one process step, since the deprotonated intermediate obtained after reaction step i) is converted in-situ without prior work-up or purification into the product of formula (I). Also, after completion of the conversion the acid chloride I can be readily isolated and purified by means of a simple protocol including crystallization and solvent evaporation to remove unwanted byproducts. Furthermore, the deprotonation step is preferably carried out with an inexpensive Grignard reagent, which allows for selective and high-yielding conversions at moderate temperatures that can be safely and smoothly carried out on an industrial scale.

A second aspect of the invention relates to a process for preparing a sulfimine compound of formula (VI)

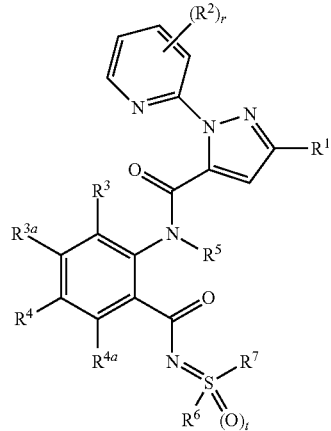

(VI)

in which $R^1$, $R^2$ and r are each as defined herein and in the claims;

$R^3$ and $R^4$ are independently selected from the group consisting of halogen, cyano, azido, nitro, —SCN, $SF_5$, $C_1$-$C_6$-alkyl, $C_1$-$C_6$-haloalkyl, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, wherein the eight last mentioned radicals may be substituted by one or more radicals $R^a$, —Si$(R^f)_2R^g$, —$OR^{b1}$, —$OS(O)_nR^{b1}$, $SR^{b1}$, —$S(O)_mR^{b1}$, —$S(O)_nN(R^{b1})R^{d1}$, —$N(R^{c1})R^{d1}$, —$N(R^{c1})C$(=O)$R^a$, —C(=O)$R^a$, —C(=O)$OR^{b1}$, —C(=S)$R^a$, —C(=S)$OR^{b1}$, —C(=N$R^{c1}$)$R^a$, —C(=N—$OR^{b1}$)H, —C(=N—N($R^{c1}$)$R^{d1}$)H, —C(=O)N($R^{c1}$)$R^{d1}$, —C(=S)N($R^{c1}$)$R^{d1}$, phenyl which may be substituted by 1, 2, 3, 4 or 5 radicals $R^e$, and a 3-, 4-, 5-, 6- or 7-membered saturated, partially unsaturated or completely unsaturated heterocyclic ring containing 1, 2 or 3 heteroatoms or heteroatom groups selected from N, O, S, NO, $SO$ and $SO_2$, as ring members, where the heterocyclic ring may be substituted by one or more radicals $R^e$;

or the radicals $R^4$ and $R^{4a}$ may be together a group selected from —$CH_2CH_2CH_2CH_2$—, —CH=CH—CH=CH—, —N=CH—CH=CH—, —CH=N—CH=CH—, —N=CH—N=CH—, —$OCH_2CH_2CH_2$—, —$OCH$=$CHCH_2$—, —$CH_2OCH_2CH_2$—, —$OCH_2CH_2O$—, —$OCH_2OCH_2$—, —$CH_2CH_2CH_2$—, —CH=$CHCH_2$—, —$CH_2CH_2O$—, —CH=CHO—, —$CH_2OCH_2$—, —$CH_2C$(=O)O—, —C(C=O)$OCH_2$—, —$O(CH_2)O$—, —$SCH_2CH_2CH_2$—, —SCH=$CHCH_2$—, —$CH_2SCH_2CH_2$—, —$SCH_2CH_2S$—, —$SCH_2SCH_2$—, —$CH_2CH_2S$—, —CH=CHS—, —$CH_2SCH_2$—, —$CH_2C$(=S)S—, —C(=S)$SCH_2$—, —$S(CH_2)S$—, —$CH_2CH_2NR^j$—, —$CH_2CH$=N—, —CH=CH—$NR^j$—, —CH=N—$NR^j$—, —OCH=N— and —SCH=N—, thus forming, together with the carbon atoms to which they are bound, a 5- or 6-membered ring, where the hydrogen atoms of the above groups may be replaced by one or more substituents selected from halogen, methyl, halomethyl, hydroxyl, methoxy and halomethoxy or one or more $CH_2$ groups of the above groups may be replaced by a C=O group;

$R^{3a}$ and $R^{4a}$ are independently selected from hydrogen and the meanings given for $R^3$ and $R^4$; or $R^{4a}$ may form together with the radical $R^4$ one of the groups defined above;

$R^5$ is selected from the group consisting of hydrogen; cyano; $C_1$-$C_{10}$-alkyl, $C_1$-$C_{10}$-haloalkyl, $C_3$-$C_8$-cycloalkyl, $C_3$-$C_8$-halocycloalkyl, $C_2$-$C_{10}$-alkenyl, $C_2$-$C_{10}$-haloalkenyl, $C_2$-$C_{10}$-alkynyl, $C_2$-$C_{10}$-haloalkynyl, wherein the eight last radicals may optionally be substituted by one or more radicals $R^a$; —N($R^{c1}$)$R^{d1}$; —Si$(R^f)_2R^g$; —$OR^{b1}$; —$SR^{b1}$; —$S(O)_mR^{b1}$; —$S(O)_nN(R^{c1})R^{d1}$; —C(=O)$R^a$; —C(=O)$OR^{b1}$; —C(=O)N($R^{c1}$)$R^{d1}$; —C(=S)$R^a$; —C(=S)$OR^{b1}$; —C(=S)N($R^{c1}$)$R^{d1}$; —C(=N$R^{c1}$)$R^a$; phenyl which may be substituted by 1, 2, 3, 4 or 5 radicals $R^e$; and a 3-, 4-, 5-, 6- or 7-membered saturated, partially unsaturated or completely unsaturated heterocyclic ring containing 1, 2 or 3 heteroatoms or heteroatom groups selected from N, O, S, NO, SO and $SO_2$, as ring members, where the heterocyclic ring may be substituted by one or more radicals $R^e$;

$R^6$ and $R^7$ are selected independently of one another from the group consisting of hydrogen, $C_1$-$C_{10}$-alkyl, $C_1$-$C_{10}$-haloalkyl, $C_3$-$C_8$-cycloalkyl, $C_3$-$C_8$-halocycloalkyl, $C_2$-$C_{10}$-alkenyl, $C_2$-$C_{10}$-haloalkenyl, $C_2$-$C_{10}$-alkynyl, $C_2$-$C_{10}$-haloalkynyl, wherein the eight last radicals may optionally be substituted by one or more radicals $R^a$;

or $R^6$ and $R^7$ together represent a $C_2$-$C_7$-alkylene, $C_2$-$C_7$-alkenylene or $C_6$-$C_9$-alkynylene chain forming together with the sulfur atom to which they are attached a 3-, 4-, 5-, 6-, 7-, 8-, 9- or 10-membered saturated, partially unsaturated or completely unsaturated ring, wherein 1 to 4 of the $CH_2$ groups in the $C_2$-$C_7$-alkylene chain or 1 to 4 of any of the $CH_2$ or CH groups in the $C_6$-$C_7$-alkenylene chain or 1 to 4 of any of the $CH_2$ groups in the $C_6$-$C_9$-alkynylene chain may be replaced by 1 to 4 groups independently selected from the group consisting of C=O, C=S, O, S, N, NO, SO, $SO_2$ and NH, and wherein the carbon and/or nitrogen atoms in the $C_2$-$C_7$-alkylene, $C_2$-$C_7$-alkenylene or $C_6$-$C_9$-alkynylene chain may be substituted with 1 to 5 substituents independently selected from the group consisting of halogen, cyano, $C_1$-$C_{10}$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl; said substituents being identical or different from one another if more than one substituent is present;

$R^a$, $R^{c1}$, $R^{d1}$, $R^e$, $R^f$, $R^g$, m and n are each as defined herein and in the claims;

$R^{b1}$ is hydrogen or has one of the meanings given herein and in the claims for $R^b$;

$R^j$ is selected from the group consisting of hydrogen, cyano, $C_1$-$C_6$-alkyl, $C_1$-$C_6$-haloalkyl, $C_1$-$C_6$-alkoxy, $C_1$-$C_6$-haloalkoxy, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl and $C_3$-$C_8$-cycloalkyl-$C_1$-$C_4$-alkyl; and t is 0 or 1;

which comprises providing a compound of the formula (I) by the process defined herein and in the claims and subsequently the step of iii) reacting the compound of the formula (I) with a compound of the formula (VII)

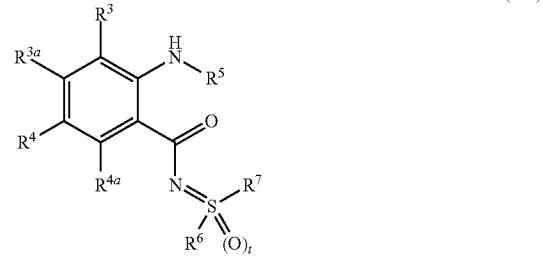

(VII)

in which the variables $R^3$, $R^{3a}$, $R^4$, $R^{4a}$, $R^5$, $R^6$, $R^7$ and t are each as defined above, in the presence of a base, to obtain a compound of the formula VI.

In the context of the present invention, the terms used generically are each defined as follows:

The prefix $C_x$-$C_y$ refers in the particular case to the number of possible carbon atoms.

The term "halogen" denotes in each case fluorine, bromine, chlorine or iodine, in particular fluorine, chlorine or bromine.

The term "partially or fully halogenated" will be taken to mean that 1 or more, e.g. 1, 2, 3, 4 or 5 or all of the hydrogen atoms of a given radical have been replaced by a halogen atom, in particular by fluorine or chlorine.

The term "alkyl" as used herein (and in the alkyl moieties of other groups comprising an alkyl group, e.g. alkoxy, alkylcarbonyl, alkylthio, alkylsulfinyl, alkylsulfonyl and alkoxyalkyl) denotes in each case a straight-chain or branched alkyl group having usually from 1 to 10 carbon atoms, frequently from 1 to 6 carbon atoms, preferably 1 to 4 carbon atoms and in particular from 1 to 3 carbon atoms. Examples of an alkyl group are methyl, ethyl, n-propyl, iso-propyl, n-butyl, 2-butyl, iso-butyl, tert-butyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, 1-methylhexyl, 2-methylhexyl, 3-methylhexyl, 4-methylhexyl, 5-methylhexyl, 1-ethylpentyl, 2-ethylpentyl, 3-ethylpentyl, n-octyl, 1-methyloctyl, 2-methylheptyl, 1-ethylhexyl, 2-ethylhexyl, 1,2-dimethylhexyl, 1-propylpentyl and 2-propylpentyl.

The term "alkylene" (or alkanediyl) as used herein in each case denotes an alkyl radical as defined above, wherein one hydrogen atom at any position of the carbon backbone is replaced by one further binding site, thus forming a bivalent moiety.

The term "haloalkyl" as used herein (and in the haloalkyl moieties of other groups comprising a haloalkyl group, e.g. haloalkoxy and haloalkylthio) denotes in each case a straight-chain or branched alkyl group having usually from 1 to 10 carbon atoms, frequently from 1 to 6 carbon atoms, wherein the hydrogen atoms of this group are partially or totally replaced with halogen atoms. Preferred haloalkyl moieties are selected from $C_1$-$C_4$-haloalkyl, more preferably from $C_1$-$C_2$-haloalkyl, more preferably from halomethyl, in particular from $C_1$-$C_2$-fluoroalkyl such as fluoromethyl, difluoromethyl, trifluoromethyl, 1-fluoroethyl, 2-fluoroethyl, 2,2-difluoroethyl, 2,2,2-trifluoroethyl, pentafluoroethyl, and the like.

The term "fluoroalkyl", as used herein (and in the fluoroalkyl units of fluoroalkoxy, fluoroalkylthio, fluoroalkylsulfinyl and fluoroalkylsulfonyl) denotes in each case straight-chain or branched alkyl groups having usually from 1 to 10 carbon atoms, frequently from 1 to 6 carbon atoms and in particular 1 to 4 carbon atoms, wherein the hydrogen atoms of this group are partially or totally replaced with fluorine atoms. Examples thereof are fluoromethyl, difluoromethyl, trifluoromethyl, 1-fluoroethyl, 2-fluoroethyl, 2,2-difluoroethyl, 2,2,2-trifluoroethyl, pentafluoroethyl, 3,3,3-trifluoroprop-1-yl, 1,1,1-trifluoroprop-2-yl, heptafluoroisopropyl, 1-fluorobutyl, 2-fluorobutyl, 3-fluorobutyl, 4-fluorobutyl, 4,4,4-trifluorobutyl, fluoro-tert-butyl and the like.

The term "cycloalkyl" as used herein (and in the cycloalkyl moieties of other groups comprising a cycloalkyl group, e.g. cycloalkoxy and cycloalkylalkyl) denotes in each case a mono- or bicyclic cycloaliphatic radical having usually from 3 to 10 carbon atoms, 3 to 8 carbon atoms or 3 to 6 carbon atoms, such as cyclopropyl, cyclobutyl, cyclopentyl, cyclohexyl, cycloheptyl, cyclooctyl, bicyclo[2.1.1]hexyl, bicyclo[3.1.1]heptyl, bicyclo[2.2.1]heptyl, and bicyclo[2.2.2]octyl.

The term "halocycloalkyl" as used herein (and in the halocycloalkyl moieties of other groups comprising an halocycloalkyl group, e.g. halocycloalkylmethyl) denotes in each case a mono- or bicyclic cycloaliphatic radical having usually from 3 to 10 carbon atoms, 3 to 8 carbon atoms or 3 to 6 carbon atoms, wherein at least one, e.g. 1, 2, 3, 4 or 5 of the hydrogen atoms are replaced by halogen, in particular by fluorine or chlorine. Examples are 1- and 2-fluorocyclopropyl, 1,2-, 2,2- and 2,3-difluorocyclopropyl, 1,2,2-trifluorocyclopropyl, 2,2,3,3-tetrafluorocyclopropyl, 1- and 2-chlorocyclopropyl, 1,2-, 2,2- and 2,3-dichlorocyclopropyl, 1,2,2-trichlorocyclopropyl, 2,2,3,3-tetrachlorocyclopropyl, 1-, 2- and 3-fluorocyclopentyl, 1,2-, 2,2-, 2,3-, 3,3-, 3,4-, 2,5-difluorocyclopentyl, 1-, 2- and 3-chlorocyclopentyl, 1,2-, 2,2-, 2,3-, 3,3-, 3,4-, 2,5-dichlorocyclopentyl and the like.

The term "fluorocylcoalkyl" as used herein, denotes a halocycloalkyl radical, as defined above, wherein the one or more halogen atoms are fluorine atoms.

The term "alkenyl" as used herein denotes in each case a singly unsaturated hydrocarbon radical having usually 2 to 10, preferably 2 to 4 carbon atoms, e.g. vinyl, allyl(2-propen-1-yl), 1-propen-1-yl, 2-propen-2-yl, methallyl(2-methylprop-2-en-1-yl), 2-buten-1-yl, 3-buten-1-yl, 2-penten-1-yl, 3-penten-1-yl, 4-penten-1-yl, 1-methylbut-2-en-1-yl, 2-ethylprop-2-en-1-yl and the like.

The term "alkenylene" (or alkenediyl) as used herein in each case denotes an alkenyl radical as defined above, wherein one hydrogen atom at any position of the carbon backbone is replaced by one further binding site, thus forming a bivalent moiety.

The term "haloalkenyl" as used herein, which may also be expressed as "alkenyl which may be substituted by halogen", and the haloalkenyl moieties in haloalkenyloxy, haloalkenylcarbonyl and the like refers to unsaturated straight-chain or branched hydrocarbon radicals having 2 to 10 ("$C_2$-$C_{10}$-haloalkenyl") or 2 to 6 ("$C_2$-$C_6$-haloalkenyl") carbon atoms and a double bond in any position, where some or all of the hydrogen atoms in these groups are replaced by halogen atoms as mentioned above, in particular fluorine, chlorine and bromine, for example chlorovinyl, chloroallyl and the like.

The term "fluoroalkenyl" as used herein, denotes a haloalkenyl radical, as defined above, wherein the one or more halogen atoms are fluorine atoms.

The term "alkynyl" as used herein denotes unsaturated straight-chain or branched hydrocarbon radicals having usually 2 to 10, frequently 2 to 6, preferably 2 to 4 carbon atoms and one or two triple bonds in any position, e.g. ethynyl, propargyl(2-propyn-1-yl), 1-propyn-1-yl, 1-methylprop-2-yn-1-yl), 2-butyn-1-yl, 3-butyn-1-yl, 1-pentyn-1-yl, 3-pentyn-1-yl, 4-pentyn-1-yl, 1-methylbut-2-yn-1-yl, 1-ethylprop-2-yn-1-yl and the like.

The term "alkynylene" (or alkynediyl) as used herein in each case denotes an alkynyl radical as defined above, wherein one hydrogen atom at any position of the carbon backbone is replaced by one further binding site, thus forming a bivalent moiety.

The term "haloalkynyl" as used herein, which is also expressed as "alkynyl which may be substituted by halogen", refers to unsaturated straight-chain or branched hydrocarbon radicals having usually 3 to 10 carbon atoms, frequently 2 to 6, preferably 2 to 4 carbon atoms, and one or two triple bonds in any position (as mentioned above), where some or all of the hydrogen atoms in these groups are replaced by halogen atoms as mentioned above, in particular fluorine, chlorine and bromine.

The term "alkoxy" as used herein denotes in each case a straight-chain or branched alkyl group usually having from 1 to 10 carbon atoms, frequently from 1 to 6 carbon atoms, preferably 1 to 4 carbon atoms, which is bound to the remainder of the molecule via an oxygen atom. Examples of an alkoxy group are methoxy, ethoxy, n-propoxy, iso-propoxy, n-butyloxy, 2-butyloxy, iso-butyloxy, tert-butyloxy, and the like.

The term "haloalkoxy" as used herein denotes in each case a straight-chain or branched alkoxy group, as defined above, having from 1 to 10 carbon atoms, frequently from 1 to 6 carbon atoms, preferably 1 to 4 carbon atoms, preferably 1 to 3 carbon atoms, wherein the hydrogen atoms of this group are partially or totally replaced with halogen atoms, in particular fluorine atoms. Preferred haloalkoxy moieties include $C_1$-$C_4$-haloalkoxy, in particular halomethoxy, and also in particular $C_1$-$C_2$-fluoroalkoxy, such as fluoromethoxy, difluoromethoxy, trifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoro-ethoxy, 2,2-dichloro-2-fluoroethoxy, 2,2,2-trichloroethoxy, pentafluoroethoxy and the like.

The term "alkoxy-alkyl" as used herein denotes in each case alkyl usually comprising 1 to 6 carbon atoms, preferably 1 to 4 carbon atoms, wherein 1 carbon atom carries an alkoxy radical usually comprising 1 to 10, frequently 1 to 6, in particular 1 to 4, carbon atoms as defined above. Examples are $CH_2OCH_3$, $CH_2$—$OC_2H_5$, n-propoxymethyl, $CH_2$—$OCH(CH_3)_2$, n-butoxymethyl, (1-methylpropoxy)-methyl, (2-methylpropoxy)methyl, $CH_2$—$OC(CH_3)_3$, 2-(methoxy)ethyl, 2-(ethoxy)ethyl, 2-(n-propoxy)-ethyl, 2-(1-methylethoxy)-ethyl, 2-(n-butoxy)ethyl, 2-(1-methylpropoxy)-ethyl, 2-(2-methylpropoxy)-ethyl, 2-(1,1-dimethylethoxy)-ethyl, 2-(methoxy)-propyl, 2-(ethoxy)-propyl, 2-(n-propoxy)-propyl, 2-(1-methylethoxy)-propyl, 2-(n-butoxy)-propyl, 2-(1-methylpropoxy)-propyl, 2-(2-methylpropoxy)-propyl, 2-(1,1-dimethylethoxy)-propyl, 3-(methoxy)-propyl, 3-(ethoxy)-propyl, 3-(n-propoxy)-propyl, 3-(1-methylethoxy)-propyl, 3-(n-butoxy)-propyl, 3-(1-methylpropoxy)-propyl, 3-(2-methylpropoxy)-propyl, 3-(1,1-dimethylethoxy)-propyl, 2-(methoxy)-butyl, 2-(ethoxy)-butyl, 2-(n-propoxy)-butyl, 2-(1-methylethoxy)-butyl, 2-(n-butoxy)-butyl, 2-(1-methylpropoxy)-butyl, 2-(2-methyl-propoxy)-butyl, 2-(1,1-dimethylethoxy)-butyl, 3-(methoxy)-butyl, 3-(ethoxy)-butyl, 3-(n-propoxy)-butyl, 3-(1-methylethoxy)-butyl, 3-(n-butoxy)-butyl, 3-(1-methylpropoxy)-butyl, 3-(2-methylpropoxy)-butyl, 3-(1,1-dimethylethoxy)-butyl, 4-(methoxy)-butyl, 4-(ethoxy)-butyl, 4-(n-propoxy)-butyl, 4-(1-methylethoxy)-butyl, 4-(n-butoxy)-butyl, 4-(1-methylpropoxy)-butyl, 4-(2-methylpropoxy)-butyl, 4-(1,1-dimethylethoxy)-butyl and the like.

The term "fluoroalkoxy-alkyl" as used herein denotes in each case alkyl as defined above, usually comprising 1 to 6 carbon atoms, preferably 1 to 4 carbon atoms, wherein 1 carbon atom carries an fluoroalkoxy radical as defined above, usually comprising 1 to 10, frequently 1 to 6, in particular 1 to 4, carbon atoms as defined above. Examples are fluoromethoxymethyl, difluoromethoxymethyl, trifluoromethoxymethyl, 1-fluoroethoxymethyl, 2-fluoroethoxymethyl, 1,1-difluoroethoxymethyl, 1,2-difluoroethoxymethyl, 2,2-difluoroethoxymethyl, 1,1,2-trifluoroethoxymethyl, 1,2,2-trifluoroethoxymethyl, 2,2,2-trifluoroethoxymethyl, pentafluoroethoxymethyl, 1-fluoroethoxy-1-ethyl, 2-fluoroethoxy-1-ethyl, 1,1-difluoroethoxy-1-ethyl, 1,2-difluoroethoxy-1-ethyl, 2,2-difluoroethoxy-1-ethyl, 1,1,2-trifluoroethoxy-1-ethyl, 1,2,2-trifluoroethoxy-1-ethyl, 2,2,2-trifluoroethoxy-1-ethyl, pentafluoroethoxy-1-ethyl, 1-fluoroethoxy-2-ethyl, 2-fluoroethoxy-2-ethyl, 1,1-difluoroethoxy-2-ethyl, 1,2-difluoroethoxy-2-ethyl, 2,2-difluoroethoxy-2-ethyl, 1,1,2-trifluoroethoxy-2-ethyl, 1,2,2-trifluoroethoxy-2-ethyl, 2,2,2-trifluoroethoxy-2-ethyl, pentafluoroethoxy-2-ethyl, and the like.

The term "alkylthio" (also alkylsulfanyl or alkyl-S—)" as used herein denotes in each case a straight-chain or branched saturated alkyl group as defined above, usually comprising 1 to 10 carbon atoms, frequently comprising 1 to 6 carbon atoms, preferably 1 to 4 carbon atoms, which is attached via a sulfur atom at any position in the alkyl group. Examples are methylthio, ethylthio, n-propylthio, iso-propylthio, n-butylthio, 2-butylthio, iso-butylthio, tert-butylthio, and the like.

The term "haloalkylthio" as used herein refers to an alkylthio group as defined above wherein the hydrogen atoms are partially or fully substituted by fluorine, chlorine, bromine and/or iodine. Examples are fluoromethylthio, difluoromethylthio, trifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoro-ethylthio, 2,2-dichloro-2-fluorethylthio, 2,2,2-trichloroethylthio, pentafluoroethylthio and the like The terms "alkylsulfinyl" and "$S(O)_n$-alkyl" (wherein n is 1) are equivalent and, as used herein, denote an alkyl group, as defined above, attached via a sulfinyl [S(O)] group. For example, the term "$C_1$-$C_6$-alkylsulfinyl" refers to a $C_1$-$C_6$-alkyl group, as defined above, attached via a sulfinyl [S(O)] group. Examples are methylsulfinyl, ethylsulfinyl, n-propylsulfinyl, 1-methylethylsulfinyl(isopropylsulfinyl), butylsulfinyl, 1-methylpropylsulfinyl(sec-butylsulfinyl), 2-methylpropylsulfinyl(isobutylsulfinyl), 1,1-dimethylethylsulfinyl(tert-butylsulfinyl), pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl and 1-ethyl-2-methylpropylsulfinyl.

The terms "alkylsulfonyl" and "$S(O)_n$-alkyl" (wherein n is 2) are equivalent and, as used herein, denote an alkyl group, as defined above, attached via a sulfonyl $[S(O)_2]$ group. For example, the term "$C_1$-$C_6$-alkylsulfonyl" refers to a $C_1$-$C_6$-alkyl group, as defined above, attached via a sulfonyl $[S(O)_2]$ group. Examples are methylsulfonyl, ethylsulfonyl, n-propylsulfonyl, 1-methylethylsulfonyl(isopropylsulfonyl), butylsulfonyl, 1-methylpropylsulfonyl(sec-butylsulfonyl), 2-methylpropylsulfonyl(isobutylsulfonyl), 1,1-dimethylethylsulfonyl(tert-butylsulfonyl), pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl.

The term "alkylamino" as used herein denotes in each case a group —NHR, wherein R is a straight-chain or branched alkyl group usually having from 1 to 6 carbon atoms, preferably 1 to 4 carbon atoms. Examples of an alkylamino group are methylamino, ethylamino, n-propylamino, isopropylamino, n-butylamino, 2-butylamino, iso-butylamino, tert-butylamino, and the like.

The term "dialkylamino" as used herein denotes in each case a group-NRR', wherein R and R', independently of each other, are a straight-chain or branched alkyl group each usually having from 1 to 6 carbon atoms, preferably 1 to 4 carbon atoms. Examples of a dialkylamino group are dimethylamino, diethylamino, dipropylamino, dibutylamino, methylethyl-amino, methyl-propyl-amino, methyl-isopropylamino, methyl-butyl-amino, methyl-isobutyl-amino, ethyl-propyl-amino, ethyl-isopropylamino, ethyl-butyl-amino, ethyl-isobutyl-amino, and the like.

The suffix "-carbonyl" in a group denotes in each case that the group is bound to the remainder of the molecule via a carbonyl C=O group. This is the case e.g. in alkylcarbonyl, haloalkylcarbonyl, alkoxycarbonyl and haloalkoxycarbonyl.

The term "aryl" as used herein refers to a mono-, bi- or tricyclic aromatic hydrocarbon radical having 6 to 14 carbon atoms. Examples thereof comprise phenyl, naphthyl, fluorenyl, azulenyl, anthracenyl and phenanthrenyl. Aryl is preferably phenyl or naphthyl and especially phenyl.

The term "3-, 4-, 5-, 6-, 7- or 8-membered saturated carbocyclic ring" as used herein refers to carbocyclic rings, which are monocyclic and fully saturated. Examples of such rings include cyclopropane, cyclobutane, cyclopentane, cyclohexane, cycloheptane, cyclooctane and the like.

The terms "3-, 4-, 5-, 6-, 7- or 8-membered partially unsaturated carbocyclic ring" and "5- or 6-membered partially unsaturated carbocyclic ring" refer to carbocyclic rings, which are monocyclic and have one or more degrees of unsaturation. Examples of such rings include cyclopropene, cyclobutene, cyclopentene, cyclohexene, cycloheptene, cyclooctene and the like.

The term "3-, 4-, 5-, 6- or 7-membered saturated, partially unsaturated or completely unsaturated heterocyclic ring containing 1, 2 or 3 heteroatoms or heteroatom groups selected from N, O, S, NO, SO and $SO_2$, as ring members" [wherein "completely/fully unsaturated" includes also "aromatic"] as used herein denotes monocyclic radicals, the monocyclic radicals being saturated, partially unsaturated or fully unsaturated (including aromatic). The heterocyclic ring may be attached to the remainder of the molecule via a carbon ring member or via a nitrogen ring member.

Examples of a 3-, 4-, 5-, 6- or 7-membered saturated heterocyclic ring include: oxiranyl, aziridinyl, azetidinyl, tetrahydrofuran-2-yl, tetrahydrofuran-3-yl, tetrahydrothien-2-yl, tetrahydrothien-3-yl, pyrrolidin-2-yl, pyrrolidin-3-yl, pyrazolidin-3-yl, pyrazolidin-4-yl, pyrazolidin-5-yl, imidazolidin-2-yl, imidazolidin-4-yl, oxazolidin-2-yl, oxazolidin-4-yl, oxazolidin-5-yl, isoxazolidin-3-yl, isoxazolidin-4-yl, isoxazolidin-5-yl, thiazolidin-2-yl, thiazolidin-4-yl, thiazolidin-5-yl, isothiazolidin-3-yl, isothiazolidin-4-yl, isothiazolidin-5-yl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2-tetrahydropyranyl, 4-tetrahydropyranyl, 1,3-dioxan-5-yl, 1,4-dioxan-2-yl, piperidin-2-yl, piperidin-3-yl, piperidin-4-yl, hexahydropyridazin-3-yl, hexahydropyridazin-4-yl, hexahydropyrimidin-2-yl, hexahydropyrimidin-4-yl, hexahydropyrimidin-5-yl, piperazin-2-yl, 1,3,5-hexahydrotriazin-2-yl and 1,2,4-hexahydrotriazin-3-yl, morpholin-2-yl, morpholin-3-yl, thiomorpholin-2-yl, thiomorpholin-3-yl, 1-oxothiomorpholin-2-yl, 1-oxothiomorpholin-3-yl, 1,1-dioxothiomorpholin-2-yl, 1,1-dioxothiomorpholin-3-yl, azepan-1-, -2-, -3- or -4-yl, oxepan-2-, -3-, -4- or -5-yl, hexahydro-1,3-diazepinyl, hexahydro-1,4-diazepinyl, hexahydro-1,3-oxazepinyl, hexahydro-1,4-oxazepinyl, hexahydro-1,3-dioxepinyl, hexahydro-1,4-dioxepinyl and the like. Examples of a 3-, 4-, 5-, 6- or 7-membered partially unsaturated heterocyclic ring include: 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4-di- or tetrahydropyridazinyl, 2-di- or tetrahydropyrimidinyl, 4-di- or tetrahydropyrimidinyl, 5-di- or tetrahydropyrimidinyl, di- or tetrahydropyrazinyl, 1,3,5-di- or tetrahydrotriazin-2-yl, 1,2,4-di- or tetrahydrotriazin-3-yl, 2,3,4,5-tetrahydro[1H]azepin-1-, -2-, -3-, -4-, -5-, -6- or -7-yl, 3,4,5,6-tetrahydro[2H]azepin-2-, -3-, -4-, -5-, -6- or -7-yl, 2,3,4,7-tetrahydro[1H]azepin-1-, -2-, -3-, -4-, -5-, -6- or -7-yl, 2,3,6,7-tetrahydro[1H]azepin-1-, -2-, -3-, -4-, -5-, -6- or -7-yl, tetrahydrooxepinyl, such as 2,3,4,5-tetrahydro[1H]oxepin-2-, -3-, -4-, -5-, -6- or -7-yl, 2,3,4,7-tetrahydro[1H]oxepin-2-, -3-, -4-, -5-, -6- or -7-yl, 2,3,6,7-tetrahydro[1H]oxepin-2-, -3-, -4-, -5-, -6- or -7-yl, tetrahydro-1,3-diazepinyl, tetrahydro-1,4-diazepinyl, tetrahydro-1,3-oxazepinyl, tetrahydro-1,4-oxazepinyl, tetrahydro-1,3-dioxepinyl and tetrahydro-1,4-dioxepinyl.

A 3-, 4-, 5-, 6- or 7-membered completely unsaturated (including aromatic) heterocyclic ring is e.g. a 5- or 6-membered fully unsaturated (including aromatic) heterocyclic ring. Examples are: 2-furyl, 3-furyl, 2-thienyl, 3-thienyl, 2-pyrrolyl, 3-pyrrolyl, 3-pyrazolyl, 4-pyrazolyl, 5-pyrazolyl, 2-oxazolyl, 4-oxazolyl, 5-oxazolyl, 4-isoxazolyl, 2-thiazolyl, 4-thiazolyl, 5-thiazolyl, 4-isothiazolyl, 2-imidazolyl, 4-imidazolyl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl and 2-pyrazinyl.

The term "a 3-, 4-, 5-, 6-, 7- or 8-membered saturated or partially unsaturated carbocyclic or heterocyclic ring containing 1, 2 or 3 heteroatoms or heteroatom groups selected from N, O, S, NO, SO and $SO_2$, as ring members" as used herein denotes a saturated or unsaturated 3- to 8-membered ring system which optionally contains 1 to 3 heteroatoms selected from N, O, S, NO, SO and $SO_2$, as defined above, with the exception of the completely unsaturated ring systems.

The remarks made below concerning preferred embodiments of the variables of the compounds of the formulae (I), (II), (VI) and (VII) are valid on their own as well as preferably in combination with each other concerning the compounds of formula (I) as well as concerning the methods according to the invention.

In the compounds of the formulae (I), (II) and (VI), $R^1$ is preferably selected from halogen, $C_1$-$C_4$-alkyl, $C_1$-$C_4$-fluoroalkyl, $CBrF_2$, $C_5$-$C_6$-cycloalkyl, $C_5$-$C_6$-fluorocycloalkyl, $C_2$-$C_4$-alkenyl, $C_2$-$C_4$-fluoroalkenyl, wherein the six last mentioned radicals may be substituted by 1, 2 or 3 radicals $R^a$; —$OR^b$, —$SR^b$; —$N(R^{c1})R^{d1}$, phenyl which may be substituted by 1, 2 or 3 radicals $R^e$, and a 5- or 6-membered saturated, partially unsaturated or aromatic heterocyclic ring containing 1 or 2 heteroatoms or heteroatom groups selected from N, O and S as ring members, where the heterocyclic ring may be substituted by 1, 2 or 3 radicals $R^e$.

More preferably $R^1$ is selected from halogen, $C_1$-$C_4$-fluoroalkyl, $CBrF_2$, $C_1$-$C_4$-alkoxy and $C_1$-$C_4$-fluoroalkoxy-$C_1$-$C_4$-alkyl, particularly selected from halogen, $CF_3$, $CHF_2$, $CBrF_2$ and methoxy, and specifically from $CF_3$ and $CHF_2$.

In the compounds of the formulae (I), (II) and (VI), each $R^2$ preferably is independently selected from halogen, $C_1$-$C_4$- alkyl, $C_1$-$C_4$-fluoroalkyl, $C_5$-$C_6$-cycloalkyl, $C_5$-$C_6$-fluorocycloalkyl, $C_2$-$C_4$-alkenyl, $C_2$-$C_4$-fluoroalkenyl, wherein the six last mentioned radicals may be substituted by one or more radicals $R^a$; —$OR^b$, —$SR^b$, —$N(R^{c1})R^{d1}$, phenyl which may be substituted by 1, 2 or 3 radicals $R^e$, and a 5- or 6-membered saturated, partially unsaturated or completely unsaturated heterocyclic ring containing 1 or 2 heteroatoms or heteroatom groups selected from N, O and S, as ring members, where the heterocyclic ring may be substituted by 1, 2 or 3 radicals $R^e$.

More preferably each $R^2$ is independently selected from halogen and halomethyl, in particular from halogen and $CF_3$ and specifically $R^2$ is chlorine.

In the compounds of the formulae (I), (II) and (VI), r is preferably 1, 2 or 3 and especially preferably 1. When r is 1, $R^2$ is preferably located in position 3 of the pyridyl moiety of the compound of the formulae I or II, i.e. is bound to the ring carbon atom of the pyridyl moiety that is ortho to the pyrazole bond.

In the compounds of the formulae (VI) and (VII), $R^3$ and $R^4$ are preferably, independently of each other, selected from halogen, cyano, nitro, $C_1$-$C_4$-alkyl, haloalkyl, $C_5$-$C_6$-cycloalkyl, $C_5$-$C_8$-halocycloalkyl, $C_2$-$C_4$-alkenyl, $C_2$-$C_4$-haloalkenyl, wherein the six last mentioned radicals may be substituted by one or more radicals $R^a$; —$OR^{b1}$, —$OS(O)_nR^{b1}$, $SR^{b1}$, —$N(R^{c1})R^{d1}$, —$C(=O)R^a$, phenyl which may be substituted by 1, 2 or 3 radicals $R^e$, and a 5- or 6-membered saturated, partially unsaturated or completely unsaturated heterocyclic ring containing 1 or 2 heteroatoms selected from N, O and S, as ring members, where the heterocyclic ring may be substituted by 1, 2 or 3 radicals $R^e$.

More preferably $R^3$ and $R^4$ are independently selected from halogen, cyano, $C_1$-$C_4$-haloalkyl. Particularly preferred $R^3$ is selected from halogen, methyl and halomethyl, specifically from chlorine, bromine, methyl, $CF_3$ and $CHF_2$, and $R^4$ is selected from halogen, cyano, methyl and halomethyl, specifically from chlorine, bromine, cyano, $CF_3$ and $CHF_2$.

In the compounds of the formulae (VI) and (VII), $R^{3a}$ and $R^{4a}$ are preferably, independently of each other, selected from hydrogen and the preferred meanings given above for $R^3$ and $R^4$.

More preferably $R^{3a}$ and $R^{4a}$ are both hydrogen.

Therefore, particularly preferred compounds of the formula (VI) are those of the formula (VIa), and particularly preferred compounds of the formula (VII) are those of the formula (VIIa):

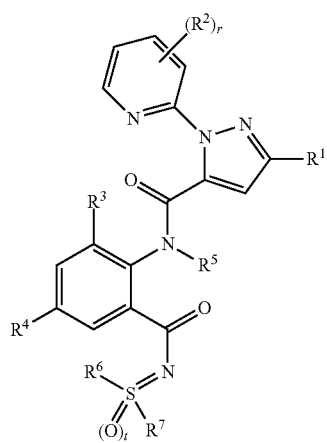

(VIa)

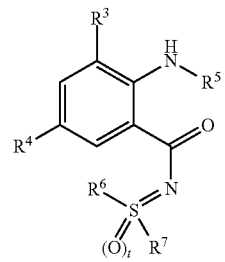

(VIIa)

in which the variables $R^3$, $R^4$, $R^5$, $R^6$, $R^7$, r and t have the meanings defined above, in particular those mentioned as preferred.

In the compounds of the formulae (VI) and (VII), $R^5$ is preferably selected from hydrogen, $C_1$-$C_6$-alkyl, $C_1$-$C_6$-haloalkyl, $C_5$-$C_6$-cycloalkyl, $C_5$-$C_6$-halocycloalkyl, wherein the four last radicals may optionally be substituted by one or more radicals $R^a$; —$C(=O)R^a$; phenyl which may be substituted by 1, 2 or 3 radicals $R^e$; and a 5- or 6-membered saturated, partially unsaturated or completely unsaturated heterocyclic ring containing 1 or 2 heteroatoms selected from N, O and S, as ring members, where the heterocyclic ring may be substituted by 1, 2 or 3 radicals $R^e$.

More preferably each $R^5$ is selected from hydrogen, $C_1$-$C_4$-alkyl, $C_1$-$C_4$-haloalkyl and —$C(C=O)$—$C_1$-$C_4$-alkyl, in particular from hydrogen, $C_1$-$C_3$-alkyl and halomethyl, and specifically $R^5$ is hydrogen.

In the compounds of the formulae (VI) and (VII), $R^6$ and $R^7$ are preferably, independently of each other, selected from hydrogen, $C_1$-$C_6$-alkyl, $C_1$-$C_6$-haloalkyl, $C_3$-$C_6$-cycloalkyl, $C_3$-$C_6$-halocycloalkyl, $C_2$-$C_4$-alkenyl, $C_2$-$C_4$-haloalkenyl, wherein the six last radicals may optionally be substituted by one or more radicals $R^a$;

or $R^6$ and $R^7$ together represent a $C_4$-$C_5$-alkylene or $C_4$-$C_5$-alkenylene chain forming together with the sulfur atom to which they are attached a 5- or 6-membered saturated or partially unsaturated ring, wherein one of the $CH_2$ groups in the $C_4$-$C_5$-alkylene chain or one of the $CH_2$ or CH groups in the $C_4$-$C_5$-alkenylene chain may be replaced by a group independently selected from O, S and N and NH, and wherein the carbon and/or nitrogen atoms in the $C_4$-$C_5$-alkylene or $C_4$-$C_5$-alkenylene chain may be substituted with 1 or 2 substituents independently selected from halogen, cyano, $C_1$-$C_4$-alkyl, $C_1$-$C_4$-haloalkyl, $C_1$-$C_4$-alkoxy, $C_1$-$C_4$-haloalkoxy.

More preferably $R^6$ and $R^7$ are independently selected from $C_1$-$C_4$-alkyl, $C_1$-$C_4$-haloalkyl, or $R^6$ and $R^7$ together represent a $C_4$-$C_5$-alkylene chain forming together with the sulfur atom to which they are attached a 5- or 6-membered ring. Particularly preferred $R^6$ and $R^7$ are each $C_1$-$C_4$-alkyl, or together represent a $C_4$-$C_5$-alkylene chain forming together with the sulfur atom to which they are attached a 5- or 6-membered ring. Specifically $R^6$ and $R^7$ are each methyl, isopropyl or ethyl, or together represent a butylene chain forming together with the sulfur atom to which they are attached a 5-membered ring.

In this context, the variables $R^a$, $R^b$, $R^c$, $R^d$, $R^{b1}$, $R^{c1}$, $R^{d1}$, $R^e$, $R^f$, $R^g$, $R^h$, $R^i$, $R^j$, t, m and n, independently of each other, preferably have one of the following meanings:

$R^a$ is selected from $C_1$-$C_4$-alkyl, $C_1$-$C_4$-fluoroalkyl, $C_3$-$C_6$-cycloalkyl, $C_3$-$C_6$-fluorocycloalkyl, $C_2$-$C_4$-alkenyl, $C_2$-$C_4$-fluoroalkenyl, $C_1$-$C_4$-alkoxy, amino, di-($C_1$-$C_4$-alkyl)-amino, phenyl and a 5- or 6-membered saturated, partially unsaturated or completely unsaturated heterocyclic ring containing 1 or 2 heteroatoms selected from N, O and S, as ring members, where phenyl and the heterocyclic ring may be substituted by 1, 2 or 3 radicals selected from $C_1$-$C_4$-alkyl, $C_1$-$C_4$-fluoroalkyl, $C_5$-$C_6$-cycloalkyl and $C_5$-$C_6$-fluorocycloalkyl.

More preferably $R^a$ is selected from $C_1$-$C_4$-alkyl and $C_1$-$C_4$-fluoroalkyl, alkoxy, di-($C_1$-$C_4$-alkyl)-amino, phenyl and a 5- or 6-membered saturated, partially unsaturated or completely unsaturated heterocyclic ring containing 1 or 2 heteroatoms selected from N, O and S, as ring members, and in particular selected from $C_1$-$C_3$-alkyl and $C_1$-$C_2$-fluoroalkyl and $C_1$-$C_2$-alkoxy.

$R^b$ is selected from $C_1$-$C_4$-alkyl, $C_1$-$C_4$-fluoroalkyl, $C_5$-$C_6$-cycloalkyl, $C_5$-$C_6$-fluorocycloalkyl, $C_1$-$C_4$-alkoxy-$C_1$-$C_4$-alkyl, $C_1$-$C_4$-fluoroalkoxy-$C_1$-$C_4$-alkyl, phenyl-$C_1$-$C_4$-alkyl, phenoxy-$C_1$-$C_4$-alkyl and pyridyl-$C_1$-$C_4$-alkyl, wherein phenyl and pyridyl in the three last mentioned radicals may optionally carry 1 or 2 radicals selected from halogen, substituents $C_1$-$C_2$-fluoroalkyl, $C_1$-$C_4$-alkoxy and $C_1$-$C_2$-fluoroalkoxy.

More preferably $R^b$ is selected from $C_1$-$C_4$-alkyl, $C_1$-$C_4$-fluoroalkyl and benzyl, and in particular selected from $C_1$-$C_3$-alkyl, $C_1$-$C_2$-fluoroalkyl and benzyl.

$R^c$, $R^d$ are, independently from one another and independently of each occurrence, selected from $C_1$-$C_4$-alkyl, $C_1$-$C_4$-fluoroalkyl, $C_5$-$C_6$-cycloalkyl, $C_5$-$C_6$-fluorocycloalkyl, wherein the four last mentioned radicals may optionally carry 1 or 2 radicals selected from $C_1$-$C_4$-alkoxy, $C_1$-$C_4$-fluoroalkoxy, $C_1$-$C_4$-fluoroalkylthio, phenyl, benzyl, pyridyl and phenoxy, wherein the four last mentioned radicals may carry 1 or 2 substituents selected from halogen, $C_1$-$C_4$-alkyl, $C_1$-$C_2$-fluoroalkyl, $C_1$-$C_4$-alkoxy and $C_1$-$C_2$-fluoroalkoxy; or $R^c$ and $R^d$, together with the nitrogen atom to which they are bound, form a 5- or 6-membered saturated, partly unsaturated or completely unsaturated heterocyclic ring which may contain 1 further heteroatom selected from N, O and S as ring members, where the heterocyclic ring may carry 1 or 2 substituents selected from halogen, $C_1$-$C_4$-alkyl and $C_1$-$C_4$-fluoroalkyl.

More preferably $R^c$, $R^d$ are, independently from one another and independently of each occurrence, selected from $C_1$-$C_4$-alkyl, $C_1$-$C_4$-fluoroalkyl and benzyl, or $R^c$ and $R^d$, together with the nitrogen atom to which they are bound, form a 5- or 6-membered saturated or partly unsaturated heterocyclic ring. In particular, $R^c$, $R^d$ are, independently from one another and independently of each occurrence, $C_1$-$C_3$-alkyl, $C_1$-$C_2$-fluoroalkyl, benzyl, or together with the nitrogen atom to which they are bound form a pyrrolidine or a piperidine ring.

$R^{b1}$ is hydrogen or has one of the preferred meanings given for $R^c$.

$R^{c1}$ is hydrogen or has one of the preferred meanings given for $R^c$.

$R^{d1}$ is hydrogen or has one of the preferred meanings given for $R^d$.

$R^e$ is selected from halogen, $C_1$-$C_4$-alkyl, $C_1$-$C_4$-fluoroalkyl, $C_2$-$C_4$-alkenyl, $C_2$-$C_4$-fluoroalkenyl, where the four last mentioned radicals may optionally carry 1 or 2 radicals selected from $C_1$-$C_2$-alkoxy; $C_1$-$C_4$-alkoxy, $C_1$-$C_4$-fluoroalkoxy, phenyl, benzyl, pyridyl and phenoxy, wherein the four last mentioned radicals may carry 1 or 2 substituents selected from halogen, $C_1$-$C_2$-alkyl and $C_1$-$C_2$-fluoroalkyl.

More preferably $R^e$ is selected from $C_1$-$C_4$-alkyl, $C_1$-$C_4$-fluoroalkyl, $C_1$-$C_4$-alkoxy and $C_1$-$C_4$-fluoroalkoxy, and in particular from $C_1$-$C_3$-alkyl, $C_1$-$C_2$-fluoroalkyl, $C_1$-$C_2$-alkoxy, $C_1$-$C_2$-fluoroalkoxy.

$R^f$, $R^g$ are, independently of each other and independently of each occurrence, selected from $C_1$-$C_4$-alkyl, $C_5$-$C_6$-cycloalkyl, $C_1$-$C_2$-alkoxy-$C_1$-$C_2$-alkyl, phenyl and benzyl.

More preferably $R^f$, $R^g$ are, independently of each other and independently of each occurrence, selected from $C_1$-$C_4$-alkyl, $C_5$-$C_6$-cycloalkyl, benzyl and phenyl, and in particular from $C_1$-$C_3$-alkyl, benzyl and phenyl.

$R^h$, $R^i$ are, independently from one another and independently of each occurrence, selected from hydrogen, halogen, $C_1$-$C_4$-alkyl, $C_1$-$C_4$-fluoroalkyl, $C_5$-$C_6$-cycloalkyl, $C_5$-$C_6$-fluorocycloalkyl, where the four last mentioned radicals may optionally carry 1 or 2 radicals selected from $C_1$-$C_3$-alkyl and $C_1$-$C_3$-fluoroalkyl; $C_1$-$C_4$-alkoxy, $C_1$-$C_4$-fluoroalkoxy, phenyl, pyridyl and phenoxy.

More preferably $R^h$, $R^i$ are, independently of each other and independently of each occurrence, selected from hydrogen, $C_1$-$C_3$-alkyl and $C_1$-$C_2$-fluoroalkyl.

$R^j$ is selected from hydrogen, $C_1$-$C_4$-alkyl, $C_1$-$C_4$-haloalkyl, $C_1$-$C_4$-alkoxy, $C_1$-$C_4$-haloalkoxy, $C_5$-$C_6$-cycloalkyl, $C_5$-$C_6$-halocycloalkyl, $C_2$-$C_4$-alkenyl, $C_2$-$C_4$-haloalkenyl, $C_2$-$C_4$-alkynyl, $C_2$-$C_4$-haloalkynyl and $C_5$-$C_6$-cycloalkyl-$C_1$-$C_2$-alkyl More preferably $R^j$ is $C_1$-$C_4$-alkyl, in particular methyl.

t is 0 or 1. More preferably t is 0.

m is 1 or 2, wherein, in the case of several occurrences, m may be identical or different. More preferably m is 2.

n is 1 or 2, wherein, in the case of several occurrences, n may be identical or different. More preferably n is 2.

The conversion in step (i) of the process according to the first aspect of the invention for preparing an N-substituted 1H-pyrazole-5-carbonylchloride compound I is a deprotonation of the carbon atom in position 5 of the pyrazole ring of compound II, i.e. an abstraction of a proton in said position. This transformation is effected by contacting the starting compounds including a compound II and a base, preferably in a solvent and under an inert atmosphere, using suitable reaction conditions.

For the deprotonation reaction in step (i) of the process according to the present invention any base selected from lithium-organic and magnesium-organic compounds, and in particular selected from lithium-organic base having a carbon or nitrogen bound lithium and magnesium-organic base having a carbon bound magnesium, such as alkyl lithium, in particular n-butyl lithium, lithium dialkyl amide, in particular lithium diisopropylamide, and alkyl and cycloalkyl magnesium halides, e.g. isopropyl magnesium chloride can be used.

According to a preferred embodiment of the invention the base in step (i) in the process of the invention is selected from $C_1$-$C_6$-alkyl magnesium halides and $C_5$-$C_6$-cycloalkyl magnesium halides, more preferably selected from $C_1$-$C_4$-alkyl magnesium chlorides, $C_1$-$C_4$-alkyl magnesium bromides, $C_5$-$C_5$-cycloalkyl magnesium chlorides and $C_5$-$C_6$-cycloalkyl magnesium bromides, and in particular selected from methyl magnesium chloride, ethyl magnesium chloride, n-propyl magnesium chloride, isopropyl magnesium chloride, methyl magnesium bromide, ethyl magnesium bromide, n-propyl magnesium bromide, isopropyl magnesium bromide.

The base employed in step (i) is generally used in an amount of 0.8 to 3.5 mol, more preferably of 1.0 to 3.0 mol, in particular of 1.01 to 2.5 mol and especially of 1.1 to 2.2 mol, based in each case on 1 mol of the compound of the formula (II).

According to a particular preferred embodiment of the invention in step (i) of the inventive process a magnesium-organic base is used in an amount of typically 1.0 to 3.5 mol, more preferably of 1.3 to 3.0 mol, in particular of 1.5 to 2.5 mol and especially of 1.7 to 2.2 mol, based in each case on 1 mol of the compound of the formula (II).

The deprotonation of step (i) is usually performed in an aprotic organic solvent. Suitable aprotic organic solvents here include, for example, aliphatic $C_2$-$C_6$ ethers, such as dimethyl ether, dimethoxyethane, diethylene glycol dimethyl ether, dipropyl ether, methyl isobutyl ether, tert-butyl methyl ether and tert-butyl ethyl ether, alicyclic $C_3$-$C_6$ ethers, such as tetrahydrofuran (THF), tetrahydropyran, 2-methyltetrahydrofuran, 3-methyltetrahydrofuran and dioxane, aliphatic hydrocarbons, such as pentane, hexane, heptane and octane, and also petroleum ether, cycloaliphatic hydrocarbons, such as cyclopentane and cyclohexane, aromatic hydrocarbons, such as benzene, toluene, the xylenes and mesitylene, or mixtures of these solvents with one another.

The solvent for the conversion in step (i) is preferably selected from aliphatic and alicyclic ethers, especially form $C_2$-$C_6$-aliphatic ethers and $C_4$-$C_6$ alicyclic ethers, or a mixture thereof. Particular preferably THF is used as solvent. Likewise, particular preferably dimethoxyethane is used as solvent. If compound II is initially present in the reaction vessel in a solvent and also the base is added in a solvent, preferably the same solvent, in particular THF or dimethoxyethane, is used in each case.

The total amount of the solvent used in step (i) of the process according to the invention is typically in the range from 500 to 6000 g and preferably in the range from 1000 to 5000 g, based on 1 mol of the compound II.

Preference is given to using solvents which are essentially anhydrous, i.e. have a water content of less than 1000 ppm and especially not more than 100 ppm.

In general, the reaction of step (i) is performed under temperature control employing a closed or unclosed reaction vessel with stirring and a cooling device.

A suitable temperature profile for the reaction in step (i) is determined by several factors, for example the reactivity of the compound II used and the type of base selected, and can be determined by the person skilled in the art in the individual case, for example by simple preliminary tests. Generally the deprotonation of step (i) will be performed at a temperature in the range from −70 to +100° C., in particular from −50 to +50° C.

The reactants can in principle be contacted with one another in any desired sequence. For example, the compound II, optionally dissolved in a solvent or in dispersed form, can be initially charged and then the base, optionally in dissolved or dispersed form, is added, or, conversely, the base, optionally dissolved or dispersed in a solvent, can be initially charged and admixed with the compound II. Alternatively, the two reactants can also be added simultaneously to the reaction vessel.

It has been found to be appropriate to initially charge the compound II, preferably in a solvent, an then adjust the reaction mixture to a temperature in the range of −70 to 30° C., preferably in the range of −50 to 25° C., depending on the reaction conditions of the individual case and in particular depending on the specific base to be used. Afterwards the base, optionally in a solvent, is added either stepwise, continuously or in one portion and the reaction is allowed to continue for a period of time, possibly at the same temperature, at an elevated temperature or at a gradually rising temperature.

If, according to a particular preferred embodiment of the invention, a magnesium-organic base is used for the conversion in step (i), compound II and the base are brought into contact at a set temperature typically in the range of −30 to 35° C., preferably of −20 to 30° C. and in particular of −10 to 25° C. or ambient temperature. Afterwards the conversion is usually continued either at the set temperature or by applying a temperature gradient with the set temperature as the lower limit and an upper limit in the range of −20 to 35°, preferably of −15 to 30° C. and in particular of −5 to 25° C. or ambient temperature.

The reaction product obtained from the conversion in step (i) of the inventive process is usually subjected without preceding work-up to the conversion in step (ii) of the process according to the first aspect of the invention. To this end, typically the reaction mixture obtained after the completion of the conversion in step (i) is directly introduced to the conversion in step (ii).

The conversion in step (ii) of the process according to the first aspect of the invention for preparing an N-substituted 1H-pyrazole-5-carbonylchloride compound of the formula (I) is a chlorocarbonylation of the intermediate product obtained in step (i) of the process. This conversion comprises an electrophilic attack of a chlorocarbonyl moiety $ClC(O)^+$ on the deprotonated carbon atom in position 5 of the pyrazole ring of the intermediate derived from compound II. Said electrophilic attack results in the covalent attachment of the chlorocarbonyl group and, as a consequence, in the formation of the N-substituted 1H-pyrazole-5-carbonylchloride compound I. This reaction is effected by contacting the intermediate obtained in step (i) with phosgene or a phosgene equivalent, preferably in a solvent and under an inert atmosphere, using suitable reaction conditions.

Suitable phosgene equivalents are compounds which have a chlorocarbonyl moiety, such as in particular diphosgene (i.e. trichloromethyl chloroformiate). However, phosgene is preferred as chlorocarbonylation reagent in step (ii).

The reactants can in principle be contacted with one another in any desired sequence. For example, the reaction mixture obtained from step (i) that includes the intermediate product resulting from the deprotonation in step (i), optionally mixed with additional solvent, can be initially charged and then a reagent selected from phosgene and phosgene equivalents, optionally in dissolved or dispersed form, is added, or, conversely, the reagent, optionally dissolved or dispersed in a solvent, can be initially charged and admixed with said intermediate. Alternatively, the two reactants can also be added simultaneously to the reaction vessel.

In case the reaction mixture of step (i) is admixed with additional solvent before the chlorocarbonylation in step (ii) is initiated, said additional solvent is an aprotic solvent which in particular is selected from the aprotic organic solvents mentioned herein before, especially from those mentioned as preferred. Preferably, the additional solvent is essentially anhydrous, i.e. it has a water content of less than 1000 ppm and especially not more than 100 ppm.

Typically the phosgene or phosgene equivalent is introduced into the reaction of step (ii) dissolved or dispersed in a suitable solvent that is generally selected from the apolar aprotic organic solvents mentioned before.

According to a preferred embodiment of the invention the chlorocarbonylation in step (ii) is effected with a solution of phosgene or phosgene equivalent in an aromatic hydrocarbon solvent, such as benzene, toluene, the xylenes or mesitylene, in particular toluene. The phosgene solution usually has a concentration of 3 to 40% by weight, preferably 10 to 30% by weight and specifically of about 20% by weight.

The chlorocarbonylation reagent, i.e. phosgene or phosgene equivalent, employed in step (ii) is usually used in an amount of 0.5 to 5 mol, preferably of 0.8 to 4.0 mol, more preferably of 0.95 to 2.5 mol and in particular of 1.0 to 2.2 mol, based in each case on 1 mol of the compound of the formula (II) as originally introduced in step (i).

In general, the conversion in step (ii) is performed under temperature control employing a closed or unclosed reaction vessel with stirring and a cooling device.

A suitable temperature profile for the reaction in step (ii) is determined by several factors, in particular the type of base that was used in the deprotonation of step (i), the reactivity of the intermediate obtained in step (i) and the chlorocarbonylation reagent selected, and can be determined by the person skilled in the art for each individual case by conventional measures, such as preliminary tests. Generally the reaction will be performed at temperatures ranging from −70 to +100° C., in particular from −50 to +50° C.

Frequently, the reaction mixture obtained after completion of step (i) is adjusted to a temperature in the range of −30 to 50° C., preferably in the range of −10 to 25° C., if required, and then the chlorocarbonylating reagent, optionally dissolved in a solvent is added. The reaction is allowed to continue for a period of time, possibly at the same temperature, or alternatively at an elevated or gradually rising temperature.

If, according to a preferred embodiment of the invention, a magnesium-organic base has been used for the conversion in step (i), the intermediate from step (i) and the reagent are brought into contact in step (ii) at a set temperature typically in the range of −30 to 35° C., preferably of −10 to 30° C. and in particular of −5 to 25° C. or ambient temperature. Afterwards the conversion is usually continued either at the set temperature or by applying a temperature gradient with the set temperature as the lower limit and an upper limit in the range of −10 to 50°, preferably of −5 to 40° C. and in particular of 0 to 25° C. or ambient temperature, and then optionally allow the reaction to proceed at the upper limit temperature.

The reaction mixture obtained after the conversion in step (ii), that contains the N-substituted 1H-pyrazole-5-carbonylchloride compound of the formula (I) as product, is usually subjected to a workup procedure before introducing it to a subsequent reaction step. The workup is typically effected by non-aqueous means known in the art to be applicable for similar reactions. Preferably, the reaction mixture, optionally after mixing it with an apolar aprotic solvent, that usually is an aliphatic ether, an acyclic ether, an aromatic hydrocarbon, in particular diethyl ether or toluene and specifically toluene, is worked-up by filtering off solids that may be present. The filtered solids, if present, are washed with the solvent, the combined filtrate is concentrated by evaporation and the residue is extracted with an apolar aprotic solvent that typically is the same as used before. Undissolved solids are again filtered off, washed with the solvent and the product is isolated from the resulting filtrate by removing solvents via evaporation. The raw N-substituted 1H-pyrazole-5-carbonylchloride compound I thus obtained can be used directly in step (iii) of the process according to the second aspect of the invention or sent to other uses. Alternatively, it can be retained for a later use or further purified beforehand. For further purification, it is possible to use one or more methods known to those skilled in the art, for example recrystallization, distillation, sublimation, zone melting, melt crystallization or chromatography. It is however preferred to subject compound II to a subsequent synthetic step in the form of the raw material obtained directly after the workup procedure.

The compounds of formula (II) are known e.g. from WO 2003/015519 or WO 2003/106427 or they can be prepared by analogy to the methods described therein or in WO 2008/126858, WO 2008/126933, WO 2008/130021, WO 2007/043677 and Bioorganic and Medicinal Chemistry Letters 2005, 15, 4898-4906.

According to further embodiments of the invention the compounds of formula (II'), that differ from compounds of formula (II) by having a substituent $R^{1a}$ instead of a substituent $R^1$, can e.g. prepared by the reaction sequence depicted in the following scheme 1.

Scheme 1:

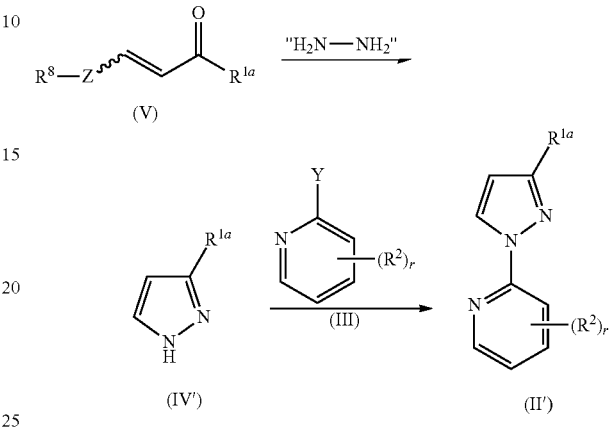

In scheme 1, the variables r and $R^2$ are as defined above. The variables Z, Y, $R^{1a}$ and $R^8$ have the following meanings:

Z is O or S;

Y is a suitable leaving group such as halogen, $C_1$-$C_3$-alkoxy, $C_1$-$C_3$-alkylthio, $C_1$-$C_3$-haloalkoxy, $C_1$-$C_3$-haloalkylthio, —S(O)$R^b$, —S(O)$_2R^b$, —OS(O)$R^b$, —OS(O)$_2R^b$ and —NO$_2$, where $R^b$ has one of the meanings given for $R^b$ above, and where $R^b$ is in particular $C_1$-$C_4$-alkyl, $C_1$-$C_4$-haloalkyl or phenyl, which is unsubstituted or which carries 1, 2 or 3 radicals selected from halogen and $C_1$-$C_4$-alkyl;

$R^{1a}$ has one of the meanings given for $R^1$, as defined herein and in the claims, with the exception of halogen, cyano and —SF$_5$;

$R^8$ is selected from the group consisting of $C_1$-$C_6$-alkyl, $C_1$-$C_6$-cycloalkyl, $C_1$-$C_6$-haloalkyl and $C_1$-$C_6$-halocycloalkyl;

The reaction of scheme 1 is particularly successful, if the variables r, Z, Y, $R^8$, $R^{1a}$ and $R^2$ on their own and in particular in combination have the following meanings:

r is 1;

Z is O;

Y is halogen, —S(O)$_2R^b$ or —OS(O)$R^b$, where $R^b$ is as defined above, and where $R^b$ is in particular $C_1$-$C_4$-alkyl;

$R^8$ is $C_1$-$C_6$-alkyl;

$R^{1a}$ is selected from the group consisting of $C_1$-$C_4$-fluoroalkyl, CBrF$_2$ and $C_1$-$C_4$-fluoroalkoxyalkyl, such as CH$_2$OCHF$_2$, and in particular selected from the group consisting of CF$_3$, CHF$_2$, CBrF$_2$ and CH$_2$OCHF$_2$;

$R^2$ is selected from the group consisting of halogen and $C_1$-$C_4$-fluoroalkyl, in particular selected from the group consisting of halogen and CF$_3$, with particular preference given to compounds of the formula III, wherein r is 1 and where $R^2$ is located in the ortho position with regard to the point of attachment of the substituent Y. In this case, $R^2$ is in particular selected from the group of halogen and $C_1$-$C_4$-fluoroalkyl, especially selected from the group consisting of halogen and CF$_3$, and more particularly $R^2$ is chlorine.

Thus, in a first step the process of scheme 1 comprises reacting a compound of formula V with hydrazine or hydrazine hydrate or a salt thereof. In a second step the thus obtained pyrazole compound of formula IV' is reacted with a pyridine compound III to yield the compound of formula (II'). The reactions of the first and the second step can be performed by analogy to the methods described in WO 2008/126858, WO 2008/126933, WO 2008/130021, WO 2007/043677 and Bioorganic and Medicinal Chemistry Letters 2005, 15, 4898-4906.

According to the first reaction depicted in scheme 1, a compound of formula V is reacted with hydrazine or hydrazine hydrate or a salt thereof. The reaction is usually achieved by contacting the compound of formula V with hydrazine or hydrazine hydrate or a salt thereof in a solvent.

Suitable solvents include water and polar protic organic solvents and mixtures thereof. Examples of suitable polar protic solvents, which can be used in step 1 of scheme 1 are in particular alcohols, such as $C_1$-$C_4$-alkanols, $C_2$-$C_4$-alkandiols, e.g. ethylene glycol or propylene glycol, di- and tri-$C_2$-$C_3$-alkylene ethers, such as diethylene glycol or triethylene glycol, mono-$C_1$-$C_4$-alkylethers, in particular monomethylethers of $C_2$-$C_4$-alkandiols, e.g. ethylene glycol monomethyl ether, or mono-$C_1$-$C_4$-alkylethers, in particular monomethylethers of di- or tri-$C_2$-$C_3$-alkylene ethers and mixtures thereof. Preferred organic solvents are selected from the group of $C_1$-$C_4$-alkanols with particular preference given to ethanol.

The hydrazine or hydrazine salt is preferably employed in an amount of from 0.7 to 10 mol, preferably from 0.9 to 5 mol and in particular from 1 to 3 mol per mol of the compound of formula (V).

It has been found advantageous to carry out the first reaction of scheme 1 in the presence of an acid. The acid may be used in catalytic or stoichiometric amounts. The amount of base may preferably be used in catalytic amounts, e.g. in an amount from 0.001 to 0.2 mol in particular in an amount from 0.01 to 0.1 mol per mol of compound V. Suitable acids are in particular strong acids such as hydrochloric acid, sulphuric acid, nitric acid, or organic sulfonic acids such as alkylsulfonic acids or arylsulfonic acids.

The reaction according to the first reaction depicted in scheme 1 is generally performed at a temperature in the range of from 0 to 150° C., preferably from 10 to 120° C. In principle, the reaction temperature can be as high as the boiling point of the reaction mixture at the given reaction pressure. The reaction pressure is generally not critical and may range from 0.9 to 2 bar, in particular from 0.9 to 1.5 bar and especially from 0.9 to 1.1 bar.

The thus obtained pyrazole can be isolated from the reaction mixture by conventional techniques, e.g. by distillation or extraction. Generally, the acid, if present, is neutralized prior to isolation of the pyrazole compound.

According to the second reaction depicted in scheme 1, a compound of formula (III) is reacted with the pyrazole compound IV. The amount of compound IV is generally from 0.8 to 1.2 mol, in particular from 0.9 to 1.1 mol per mol of compound III.

The reaction is usually achieved by contacting the compound of formula (IV) with the compound III in a solvent. In particular embodiments of the invention, the second reaction depicted in scheme 1 is carried out in an aprotic organic solvent or a mixture of aprotic organic solvents. Examples of suitable aprotic solvents are halogenated alkanes, such as methylene chloride, chloroform or 1,2-dichlorethane, aromatic hydrocarbons, such as toluene, xylenes or chlorobenzene, open-chained ethers, such as diethylether, methyl-tert-butyl ether, diisopropyl ether or methyl-isobutyl ether, cyclic ethers, such as tetrahydrofuran, 1,4-dioxane or 2-methyl tetrahydrofuran, alkylamides of aliphatic carboxylic acids such as N,N-dimethyl formamide, N,N-dimethyl acetamide, N—$C_1$-$C_4$-alkyl lactames such as N-methyl pyrrolidinone, sulfoxides such as dimethylsulfoxide, nitriles such acetonitrile or propionitrile and pyridines such as pyridine, 2,6-dimethylpyridine or 2,4,6-trimethylpyridine. Preferably the reaction is carried out a polar aprotic solvent, in particular in a solvent selected from N,N-di-$C_1$-$C_4$-alkylamides of aliphatic carboxylic acids such as N,N-dimethyl formamide or N,N-dimethyl acetamide, and N—$C_1$-$C_4$-alkyl lactames such as N-methyl pyrrolidinone.

It has been found advantageous to carry out the second reaction of scheme 1 in the presence of a base. The base may be used in catalytic or stoichiometric amounts. The amount of base may preferably be used in at least almost stoichiometric amounts, e.g. in an amount from 0.9 to 5 mol in particular in an amount from 1 to 2 mol per mol of compound IV. Suitable bases are in particular oxo bases. Suitable oxo bases include but are not limited to hydroxides, in particular alkalimetal hydroxides such as lithium, sodium or potassium hydroxide, carbonates, in particular alkalimetal carbonates, such as lithium, sodium or potassium carbonates, hydrogen carbonates, in particular alkalimetal hydrogen carbonates, such as lithium, sodium or potassium hydrogen carbonates, phosphates or hydrogenphosphates, in particular alkalimetal phosphates or hydrogenphosphates, such as lithium, sodium or potassium phosphate, or lithium, sodium or potassium hydrogen phosphate, alkoxides, in particular alkalimetal alkoxides such as sodium or potassium methoxide, sodium or potassium ethoxide or sodium or potassium tert-butanolate, carboxylates, in particular alkalimetal carboxylates, such as lithium, sodium or potassium formiate, lithium, sodium or potassium acetate or lithium, sodium or potassium propionate. Suitable amine bases include but are not limited to ammonia and organic amines, in particular aliphatic or cycloaliphatic amines, e.g. di-$C_1$-$C_4$-alkylamines, tri-$C_1$-$C_4$-alkylamines, $C_3$-$C_6$-cycloalkylamines, $C_3$-$C_6$-cycloalkyl-di-$C_1$-$C_4$-alkylamines or cyclic amines such as dimethylamine, diethylamine, diisopropylamine, cyclohexylamine, dimethylcyclohexylamine, trimethylamine, diethylamine or triethylamine, piperidine and N-methylpiperidine. Preferred bases are alkalimetal carbonates, especially sodium, potassium and cesium carbonate.

The reaction according to the second reaction depicted in scheme 1 is generally performed at a temperature in the range of from 50 to 200° C., preferably from 100 to 180° C. In principle the reaction temperature can be as high as the boiling point of the reaction mixture at the given reaction pressure. The reaction pressure is generally not critical and may range from 0.9 to 2 bar, in particular from 0.9 to 1.5 bar and especially from 0.9 to 1.1 bar.

The compound of formula (II') formed in this reaction can be isolated from the reaction mixture by customary methods, e.g. by distillation or by crystallization or precipitation from the reaction mixture, preferably after having removed insoluble byproducts. The compound of formula II' can also be isolated from the reaction mixture by addition of water to the reaction mixture and extracting the thus obtained mixtures with a suitable solvent. Suitable solvents for extraction purposes are essentially immiscible with water and are capable of dissolving sufficient amounts of compound II'. It is also possible to concentrate the reaction mixture by distilling off the solvent, mixing the thus obtained residue with water and extracting the thus obtained mixture with a suitable solvent. Examples of suitable solvents are aliphatic hydrocarbons, such as alkanes, e.g. pentane, hexane or heptane, cycloaliphatic hydrocarbons, such as cycloalkanes, e.g.

cyclopentane or cyclohexane, halogenated alkanes, such as methylene chloride or chloroform, aromatic hydrocarbons, such as benzene, toluene, the xylenes or chlorobenzene, open-chained ethers, such as diethylether, methyl-tert-butyl ether or methyl-isobutyl ether, or esters, such as ethyl acetate or ethyl propionate.

The isolated product II' can be further purified, e.g. by crystallization or distillation. However, frequently, the product is already obtained in a purity which does not require further purification steps.

Vinyl(thio)ether compounds of formula V are either commercially available on a large scale or easily produced using standard methods of organic chemistry, a skilled person is familiar with. Likewise, the compounds of formula (III) are readily available or can be prepared by analogy to routine methods of organic chemistry.

In step (iii) of the process according to the second aspect of the invention for preparing a sulfimine compound of formula (VI), a compound of formula (VII) is reacted with a pyrazole compound of formula (I) to yield a compound of formula (VI). The reaction of step (iii) can be carried out by analogy to conventional amidation reactions of carboxylic acid chlorides with aromatic amines as described e.g. in WO 2003/015519, WO 2006/062978, WO 2008/07158 or WO 2009/111553.

Surprisingly, the group $N=S(O)_xR^6R^7$ does not interfere with the amidation reaction. Rather, the compounds of formula VI, can be obtained in high yields with high purity.

Usually, the compounds of formula (VII) and the compounds of formula (I) are preferably employed in stoichiometric or almost stoichiometric amount. Generally, the relative molar ratio of the compounds of formula (VII) to the compounds of formula (I) will be in a range from 1.1:1 to 1:2, preferably from 1.1:1 to 1:1.2 and in particular from 1.05:1 to 1:1.1.

It has been found advantageous to carry out the reaction of step (iii) in the presence of a base. Suitable bases include bases which are soluble or insoluble in the reaction medium. The base may be used in catalytic or stoichiometric amounts. The amount of base may preferably be in the range from 0.9 to 2 mol, in particular from 1 to 1.8 mol per mol of compound I.

Suitable bases include but are not limited to oxo bases and amine bases. Suitable oxo bases include but are not limited to carbonates, in particular alkali metal carbonates, such as lithium, sodium or potassium carbonates, phosphates, in particular alkalimetal phosphates, such as lithium, sodium or potassium phosphate. Suitable amine bases include but are not limited to tertiary organic amines, in particular aliphatic or cycloaliphatic tertiary amines, e.g. tri-$C_1$-$C_4$-alkylamines, $C_3$-$C_6$-cycloalkyl-di-$C_1$-$C_4$-alkylamines, tertiary cyclic amines and pyridines such as dimethylcyclohexylamine, trimethylamine, triethylamine, N-methylpiperidine, N-methylmorpholine, pyridine, 2,6-dimethylpyridine, 2,4,6-trimethylpyridine or quinoline. Preferred bases are alkalimetal carbonates, such as lithium, sodium or potassium carbonates and tertiary amines in particular triethylamine, pyridine, 2,6-dimethylpyridine or 2,4,6-trimethylpyridine.

In addition to or instead of the base, an amidation catalyst can be used. Suitable amidation catalysts are dialkylaminopyridines such as 4-(N,N-dimethylamino)pyridine (4-DMAP). The catalyst is usually employed in amounts from 0.001 to 1 mol, in particular from 0.005 to 0.2 mol, especially from 0.01 to 0.1 mol per mol of compound of formula (I).

In particular embodiments of the invention, the reaction of step (iii) is carried out in an organic solvent or a mixture of organic solvents. Suitable solvents for carrying out the reaction of step (iii) are preferably aprotic solvents and mixtures thereof. Examples of aprotic solvents are aliphatic hydrocarbons, such as alkanes, e.g. pentane, hexane or heptane, octane, cycloaliphatic hydrocarbons, such as cycloalkanes, e.g. cyclopentane or cyclohexane, halogenated alkanes, such as methylene chloride, chloroform or 1,2-dichlorethane, aromatic hydrocarbons, such as benzene, toluene, the xylenes, mesitylene or chlorobenzene, open-chained ethers, such as diethylether, methyl-tert-butyl ether, diisopropyl ether or methyl-isobutyl ether, cyclic ethers, such as tetrahydrofuran, 1,4-dioxane or 2-methyl tetrahydrofuran, nitriles, such as acetonitrile or propionitrile, the aforementioned pyridines such as pyridine, 2,6-dimethylpyridine or 2,4,6-trimethylpyridine, N,N-di-$C_1$-$C_4$-alkylamides of aliphatic carboxylic acids such as N,N-dimethylformamide, N,N-dimethylacetamide, and N—$C_1$-$C_4$-alkyl lactames such as N-methyl pyrrolidinone. Particular preferred solvents for carrying out reaction of step (iii) are cyclohexane, dichloromethane, chlorobenzene, toluene, pyridine, tetrahydrofurane and N,N-dimethyl formamide, and mixtures thereof.

The reaction according to step (iii) of the inventive process is generally performed at a temperature in the range of from −40 to +150° C., preferably from 0 to 110° C. and more preferably from 30 to 80° C. In principle the reaction temperature can be as high as the boiling point of the reaction mixture at the given reaction pressure, but is preferably kept at the indicated lower values. The reaction pressure is generally not critical and may range from 0.9 to 2 bar, in particular from 0.9 to 1.5 bar and especially from 0.9 to 1.1 bar.

The reaction of step (iii) is carried out by reacting compound of formula (VII) with a suitable amount of a compound of formula (I) under the above reaction conditions. The reaction can be performed for example in the following manner: a solution or a suspension of the base and of the compound of formula (VII) in a suitable organic solvent is charged to a suitable reaction vessel. To this mixture, the compound of formula (I) is added, preferably as a solution or suspension in an organic solvent. Addition of the compound of formula (I) may be done as a single portion or preferably continuously or in several portions. To the resulting mixture, the catalyst may be added, if desired. The catalyst may be added either neat, in solution or as a suspension in a suitable organic solvent.

The compound of formula (VI) formed in reaction of step (iii) can be isolated from the reaction mixture by customary methods, e.g. by removal of the base from the reaction mixture by either filtration or extraction with water, followed by concentration by distilling off the solvent. Alternatively, the reaction mixture can be diluted with water and cooled to a temperature between −30 and +30° C. to precipitate the amide compound from the solvent or solvent mixture. The precipitated amide compound VI can be separated from the liquid reaction mixture by conventional means, e.g. by filtration, centrifugation etc. The amide compound of formula VI can also be isolated from the reaction mixture by addition of water to the reaction mixture and extracting the thus obtained mixtures with a suitable solvent. Suitable solvents for extraction purposes are essentially immiscible with water and are capable of dissolving sufficient amounts of compound VI. It is also possible to concentrate the reaction mixture by distilling of the solvent, mixing the thus obtained residue with water and extracting the thus obtained mixture with a suitable solvent. Examples of suitable solvents are aliphatic hydrocarbons, such as alkanes, e.g. pentane, hexane or heptane, cycloaliphatic hydrocarbons, such as cycloalkanes, e.g. cyclopentane or cyclohexane, halogenated alkanes, such as methylene chloride or chloroform, aromatic hydrocarbons, such as benzene, toluene, the xylenes or chlorobenzene, open-chained ethers, such as diethylether, methyl-tert-butyl ether or methyl-isobutyl ether, or esters, such as ethyl acetate or ethyl propionate.

The thus obtained compound of formula (VI) can be further purified, e.g. by crystallization or by chromatography or combined measures. However, frequently, the product is already obtained in a purity which does not require further purification steps.

The invention relates to a process for preparing a compound of the formula (VII). This process is hereinafter termed "process VII". According to a first embodiment, process VII comprises reacting a compound of the formula (VIII) with a compound of formula (IX). According to a second embodiment, process VII comprises reacting a compound of the formula (VIII) with a compound of formula (X).

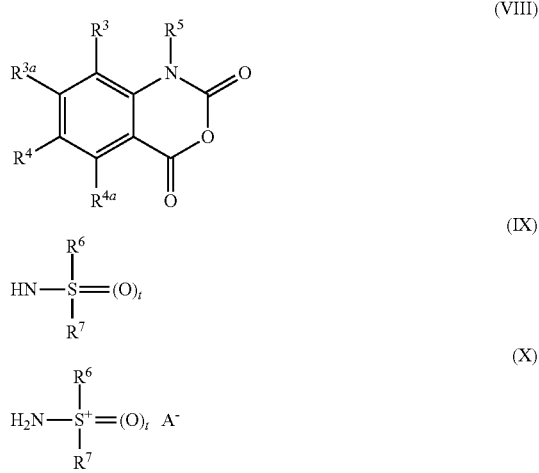

where $R^3$, $R^4$, $R^{3a}$, $R^{4a}$, $R^5$, t, $R^6$ and $R^7$ are as defined herein and in the claims and where $A^-$ is an equivalent of an anion having a $pK_B$ of at least 10, as determined under standard conditions (298 K; 1.013 bar) in water.

For the conversion in process VII particular preference is given to compounds of the formula (VIII) wherein $R^{3a}$ and $R^{4a}$ are both hydrogen, $R^5$ is as defined herein and in the claims and where $R^3$ has one of the meanings given herein and in the claims or is hydrogen, and $R^4$ has one of the meanings given herein and in the claims or is hydrogen. Preferably, the radical $R^3$ and $R^4$ in formula (VIII) are, independently of each other, selected from the group consisting of hydrogen, halogen, $C_1$-$C_4$-alkyl, $C_1$-$C_4$-haloalkyl and cyano, it being possible that $R^3$ and $R^4$ are identical or different.

In the process VII of the present invention, preference is given to compounds of the formulae (IX) and (X), where the variable t is 0 and where $R^6$ and $R^7$, independently of each other, have one of the meanings defined herein.

In the process VII of the present invention, more preference is given to compounds of the formulae (IX) and (X), where the variable t is 0 and where $R^6$ and $R^7$, independently of each other, are selected from the group consisting of $C_1$-$C_6$-alkyl, $C_1$-$C_6$-haloalkyl, $C_3$-$C_6$-cycloalkyl, $C_3$-$C_6$-halocycloalkyl, $C_2$-$C_6$-alkenyl, $C_2$-$C_6$-haloalkenyl, wherein alkyl, alkenyl and cycloalkyl may optionally be substituted by one or more, e.g. 1 or 2 radicals $R^a$, where $R^a$ is as defined above and in particular has one of the preferred meanings given above for $R^a$. Particular preference is given to compounds of the formulae (IX) and (X), where the variable t is 0 and where $R^6$ and $R^7$, independently of each other, are preferably selected from the group consisting of $C_1$-$C_6$-alkyl, $C_3$-$C_6$-cycloalkyl and $C_3$-$C_6$-cycloalkyl-$C_1$-$C_4$-alkyl.

Likewise, preference is given to compounds of the formulae (IX) and (X), where the variable t is 0 and where $R^6$ and $R^7$ together represent a $C_4$-$C_6$-alkylene or $C_4$-$C_6$-alkenylene group forming together with the sulfur atom to which they are attached a 5-, 6- or 7-membered, saturated or partially unsaturated ring, wherein 1 or 2 of the $CH_2$ groups in the $C_4$-$C_6$-alkylene chain or 1 or 2 of any of the $CH_2$ or CH groups in the $C_4$-$C_6$-alkenylene chain may be replaced may be replaced by 1 or 2 groups independently selected from the group consisting of O, S, N and NH. Particular preference is also given to compounds of the formulae (IX) and (X), where the variable t is 0 and where $R^6$ and $R^7$ together preferably represent a $C_4$-$C_6$-alkylene group forming together with the sulfur atom to which they are attached a 5-, 6- or 7-membered saturated ring.

In the process VII of the present invention, preference is also given to compounds of the formulae (IX) and (X), where the variable t is 1 and where $R^6$ and $R^7$, independently of each other, have one of the meanings defined herein, in particular one of the meanings mentioned herein as preferred.

In the compounds of formula (X), $A^-$ is an equivalent of an anion having a $pK_B$ of at least 10, as determined under standard conditions (298 K; 1.013 bar) in water. In this context "equivalent" means the amount of anion required to achieve electroneutrality. For example, if the anion carries one negative charge the equivalent is 1, while if the anione carries two negative charges the equivalent is ½. Suitable anions are those, which have a basicity constant $pK_B$ of at least 10, in particular at least 12 as determined under standard conditions (298 K; 1.013 bar) in water. Suitable anions include inorganic ions such as $SO_4^{2-}$, $HSO4^-$, $Cl^-$, $ClO_4^-$, $BF_4^-$, $PF_6^-$, $HPO_4^-$, and organic anions such as methylsulfonate, trifluoromethylsulfonate, trifluoroacetate, phenylsulfonate, toluenesulfonate, mesitylene sulfonate and the like.

In process VII, the compounds of formulae (IX) or (X), respectively, are typically employed in an amount of from 0.9 to 2 mol, preferably from 0.9 to 1.5 mol, more preferably from 0.9 to 1.2 mol and in particular from 0.95 to 1.1 mol per mol of the compound of formula (XIII) used in process VII.

It has been found advantageous to carry out the reaction of process VII in the presence of a base. Suitable bases include bases which are soluble or insoluble in the reaction medium. The base may be used in catalytic or stoichiometric amounts. The amount of base may preferably be in the range from 0.1 to 2 mol, in particular from 0.9 to 1.5 mol per mol of compound VIII or in the range from 0.1 to 2 mol, in particular from 0.9 to 1.5 mol per mol of compound IX or X. In a particular embodiment the base is used in an amount of at least 0.9 mol, in particular at least 1 mol, e.g. from 0.9 to 2 mol, in particular from 1 to 1.5 mol per mol of compound VIII, in particular, if a compound of formula (X) is used.

Suitable bases include but are not limited to oxo bases and amine bases. Suitable oxo bases include but are not limited to those mentioned in context with the reaction of scheme 1 herein before. Preferred bases are oxo bases, in particular alkalimetal alkoxides, which are also termed alkalimetal alkanolates, especially sodium and potassium alkanolates such as sodium methoxides, potassium methoxide, sodium ethoxide, potassium ethoxide, sodium tert-butanolate or potassium tert-butanolate. Mixtures of oxo bases and amine bases may also be used.

In particular embodiments of the invention, the reaction of process VII is carried out in an organic solvent or a mixture of organic solvents. Suitable solvents for carrying out reaction VII may be protic or aprotic solvents and mixtures thereof, with aprotic solvents being preferred. Examples of aprotic solvents are aliphatic hydrocarbons, such as alkanes, e.g. pentane, hexane or heptane, cycloaliphatic hydrocarbons, such as cycloalkanes, e.g. cyclopentane or cyclohexane, halogenated alkanes, such as methylene chloride, chloroform or 1,2-dichlorethane, aromatic hydrocarbons, such as benzene, toluene, the xylenes or chlorobenzene, open-chained ethers, such as diethylether, methyl-tert-butyl ether, diisopropyl ether or methyl-isobutyl ether, cyclic ethers, such as tetrahydrofuran, 1,4-dioxane or 2-methyl tetrahydrofuran, or esters, such as ethyl acetate or ethyl propionate. Suitable aprotic solvents may also be pyridines such as pyridine, 2,6-dimethylpyridine or 2,4,6-trimethylpyridine, N,N-di-$C_1$-$C_4$-alkylamides of aliphatic carboxylic acids such as N,N-dimethyl formamide, N,N-dimethyl acetamide, and N—$C_1$-$C_4$-alkyl lactames such as N-methyl pyrrolidinone. Examples for polar protic solvents are $C_1$-$C_4$-alkanols, such as methanol, ethanol, propanol or isopropanol, $C_2$-$C_4$-alkandiols, such as ethylene glycol or propylene glycol, ether alkanols, such as diethylene glycol, sulfoxides, such as dimethyl sulfoxide, and mixtures thereof. Preferably the reaction is carried out in an aprotic solvent or a mixture of aprotic solvents.

The reaction according to process VII is generally performed at a temperature in the range of from −40 to +150° C., preferably from 0 to 110° C. and more preferably from 0 to 80° C. In principle the reaction temperature can be as high as the boiling point of the reaction mixture at the given reaction pressure, but is preferably kept at the indicated lower values. The reaction pressure is generally not critical and may range from 0.9 to 2 bar, in particular from 0.9 to 1.5 bar and especially from 0.9 to 1.1 bar.

The reaction of process VII is carried out by reacting compound VIII with a suitable amount of a compound of formulae (IX) or (X) under the above reaction conditions. The reaction can be performed for example in the following manner: a solution or a suspension of the compound of formula (VIII) in a suitable organic solvent is added to a suitable reaction vessel. To this mixture, the compound of formulae (IX) or (X) is added, preferably as a solution or suspension in an organic solvent. Addition of compound IX or X may be done as a single portion or preferably continuously or in several portions. To the resulting mixture, the base may be added, if desired. The base may be added either neat, in solution or as a suspension in a suitable organic solvent. Addition of the base may be done as a single portion or preferably continuously or in several portions. It is also possible to add the compound and, if desired, the base at the same time.

The compound of formula (VII) formed in reaction of process VII can isolated from the reaction mixture by customary methods, e.g. by the addition of water and subsequent extraction with a suitable solvent, followed by concentration by distilling off the solvent. Suitable solvents for extraction purposes are essentially immiscible with water and capable of dissolving the compound of formula VII. Examples are aliphatic hydrocarbons, such as alkanes, e.g. pentane, hexane or heptane, cycloaliphatic hydrocarbons, such as cycloalkanes, e.g. cyclopentane or cyclohexane, halogenated alkanes, such as methylene chloride or chloroform, aromatic hydrocarbons, such as benzene, toluene, the xylenes or chlorobenzene, open-chained ethers, such as diethylether, methyl-tert-butyl ether or methyl-isobutyl ether, or esters, such as ethyl acetate or ethyl propionate.

The isolated product can be further purified, e.g. by crystallization or by chromatography or combined measures. However, frequently, the product is already obtained in a purity which does not require further purification steps.

The compounds of formulae (IX) and (X) are known from prior art, e.g. from WO 2007/006670; WO 2008/141843; Y. Tamura et al, Tetrahedron 1975, 31, 3035-3040; Fujii et al., Heteroatom Chemistry 2004, 15(3), 246-250; Johnson et al., J. Org. Chem. 1989, 54, 986-988; Yoshimura et al., J. Org. Chem. 1976, 41, 1728-1733; Appel et al., Chem. Ber. 1962, 95, 849-854 and Chem. Ber. 1966, 99, 3108-3117; or from Young et al, J. Org. Chem. 1987, 52, 2695-2699; or they can be prepared by analogy to the methods described therein or by analogy to the methods described in WO 2008/141843, U.S. Pat. No. 6,136,983 and the literature cited therein.

A particular suitable method for preparing the compounds of formula (X) is described scheme 2 below.

Scheme 2:

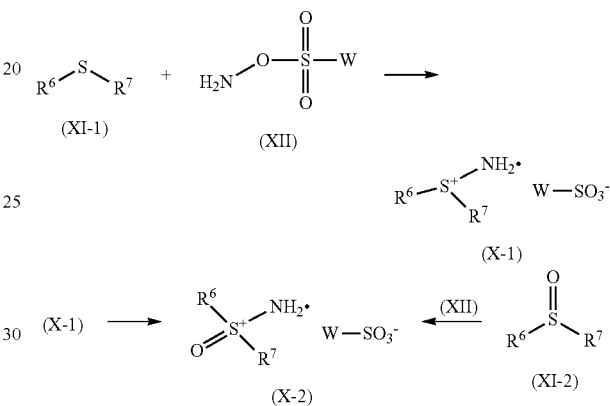

In scheme 2, $R^6$ and $R^7$ are as defined above. W can be any group which does not disturb the reaction, such as OH, $NH_2$, $C_1$-$C_4$-alkyl, $C_1$-$C_4$-haloalkyl, aryl or hetaryl, where the last two radicals are unsubstituted or substituted by 1, 2 or 3 radicals $R^e$, which are preferably selected from halogen and $C_1$-$C_4$-alkyl. W is preferably OH or preferably an aromatic group such as phenyl, optionally substituted with one or more radicals selected from halogen and $C_1$-$C_4$-alkyl, for example phenyl, 4-methylphenyl or 2,4,6-trimethylphenyl. In a particular embodiment W is OH.

According to the first reaction depicted in scheme 2, a sulfonyl hydroxylamine of formula (XII) is reacted with a sulfide of formula (XI-1), yielding a compound of formula (X-1) which corresponds to a compound of formula X, where t=0. The reaction can be performed by contacting the compounds of formula (XI) and (XII).

The compound of formula (XII) is preferably employed in an amount of from 0.7 to 1.1 mol, preferably from 0.8 to 1.0 mol and in particular from 0.85 to 0.99 mol per mol of the compound of formula (XI-1).

It has been found advantageous to carry out the first reaction of scheme 2 in the presence of a base. The base may be used in catalytic or stoichiometric amounts. The amount of base may preferably be in the range from 0.9 to 2 mol, in particular from 0.9 to 1.5 mol per mol of compound II or in the range from 1.0 to 1.2 mol per mol of compound XII.

Suitable bases include in particular oxo bases. Suitable oxo bases include but are not limited to those mentioned in context with the reaction of step (iii). Preferred bases alkalimetal alkoxides, especially sodium and potassium alkanolates, such as sodium methoxides, potassium methoxide, sodium ethoxide, potassium ethoxide, sodium tert-butanolate or potassium tert-butanolate.

In particular embodiments of the invention, the first reaction depicted in scheme 2 is carried out in an organic solvent or a mixture of organic solvents. Suitable solvents include but are not limited to polar protic or aprotic solvents and mixtures thereof, with protic solvents being preferred. Examples of polar aprotic solvents are halogenated alkanes, such as methylene chloride, chloroform or 1,2-dichlorethane, halogenated aromatic hydrocarbons, such as chlorobenzene, open-chained ethers, such as diethylether, methyl-tert-butyl ether, diisopropyl ether or methyl-isobutyl ether, cyclic ethers, such as tetrahydrofuran, 1,4-dioxane or 2-methyl tetrahydrofuran, or esters, such as ethyl acetate or ethyl propionate, N,N-di-$C_1$-$C_4$-alkylamides of aliphatic carboxylic acids such as N,N-dimethyl formamide, N,N-dimethyl acetamide, and lactames such as N-methyl pyrrolidinone. Examples for polar protic solvents are $C_1$-$C_4$-alkanols such as methanol, ethanol, propanol and isopropanol, $C_2$-$C_4$-alkandiols, such as ethylene glycol or propylene glycol, and ether alkanols such as diethylene glycol, and mixtures thereof. Preferably the reaction is carried out in a protic solvent or a mixture thereof with an aprotic solvent. In particular, the solvent is a $C_1$-$C_4$-alkanol or a mixture of $C_1$-$C_4$-alkanols.

The reaction according to the first reaction depicted in scheme 2 is generally performed at a temperature in the range of from −50 to +20° C., preferably from −40 to 10° C. and more preferably from −40 to +5° C. The reaction pressure is generally not critical and may range from 0.9 to 2 bar, in particular from 0.9 to 1.5 bar and especially from 0.9 to 1.1 bar.

The first reaction of scheme 2 is carried out by reacting compound XI-1 with a suitable amount of a compound of formulae XII under the above reaction conditions. The reaction can be performed for example in the following manner: a solution or a suspension of a compound of formula (XI-1), optionally containing a base, in a suitable organic solvent is charged to a suitable reaction vessel. To this mixture the compound XII, preferably as a solution or suspension in an organic solvent is added at the above temperatures. Addition of compound XII may be done as a single portion or preferably continuously or in several portions.

The compound of formula (X-1) formed in this reaction can be isolated from the reaction mixture by customary methods, e.g. by crystallization or precipitation from the reaction mixture, preferably after having removed insoluble by products. Precipitation or crystallization may be achieved by concentration of the reaction mixture, cooling the reaction mixture or addition of an "anti-solvent" to the reaction mixture. Anti-solvents are organic solvents, wherein the compound X-1 is insoluble or only sparingly soluble. Suitable anti-solvents include but are not limited to aliphatic hydrocarbons, such as alkanes, e.g. pentane, hexane or heptane, cycloaliphatic hydrocarbons, such as cycloalkanes, e.g. cyclopentane or cyclohexane, aromatic hydrocarbons, such as benzene, toluene, the xylenes or chlorobenzene and open-chained ethers, such as diethylether, methyl-tert-butyl ether or methyl-isobutyl ether.

The isolated product can be further purified, e.g. by crystallization or tituration with a solvent, e.g. with acetonitrile. However, frequently, the product is already obtained in a purity which does not require further purification steps.

Compounds of formula (X), in which t is 1 (compounds X-2), may be prepared from compounds of formula (X-1) by oxidation with an appropriate oxidant, in analogy to described methods as described by, for example, Dillard et al, Journal of Medicinal Chemistry 1980, 23, 717-722. The compounds of formula (X-2) may also be prepared by reacting a sulfoxide XI-2 with an amination agent, such as a compound XII, in particular aminoxysulfonic acid $NH_2OSO_3H$, under similar conditions as described for the reaction of XI-1 with XII.

The compounds of formula (VIII) are known from prior art, e.g. from WO 2003/016284 and Coppola, Synthesis 1980, pp. 505-536, or they can be prepared by analogy to the methods described therein. The compounds VIII can also be prepared by reacting an anthranilic acid derivative XIII with carbonic ester or an equivalent thereof such as phosgene, diphosgene (trichloromethyl chloroformiate), triphosgene (bis(trichloromethyl)carbonate), dialkyl carbonates, or alkyl chloroformiates as depicted in scheme 3.

Scheme 3:

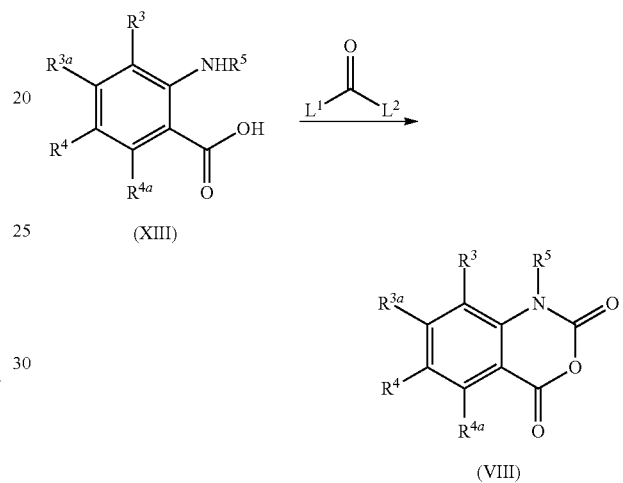

(XIII)

(VIII)

In scheme 3, $R^3$, $R^4$, $R^{3a}$, $R^{4a}$ and $R^5$ are as defined above. $L^1$ is halogen, in particular chlorine, $C_1$-$C_4$-alkoxy, in particular methoxy or ethoxy, or trichloromethoxy. $L^2$ is halogen, in particular chlorine, trichloromethoxy, O—C(O)—Cl or $C_1$-$C_4$-alkoxy, in particular methoxy or ethoxy. Examples of suitable compounds of the formula $C(O)L^1L^2$ are phosgene, diphosgene, triphosgene, methyl or ethyl chloroformate, dimethylcarbonate and diethylcarbonate. The reaction of XIII with $C(O)L^1L^2$ can be achieved by analogy to the processes described in WO 2007/43677.

The reactions described herein are carried out in reaction vessels customary for such reactions, the reaction being configurable continuously, semicontinuously or batchwise.

EXAMPLES

The compounds can be characterized e.g. by coupled High Performance Liquid Chromatography/mass spectrometry (HPLC/MS), by $^1$H-NMR and/or by their melting points. The following analytical procedures were employed:

Method A: Analytical HPLC column: RP-18 column Chromolith Speed ROD from Merck KgaA, Germany). Elution: acetonitrile+0.1% trifluoroacetic acid (TFA)/water+0.1% trifluoroacetic acid (TFA) in a ratio of from 5:95 to 95:5 in 5 minutes at 40° C.

Method B: Analytical UPLC column: Phenomenex Kinetex 1.7 μm XB-C18 100A; 50×2.1 mm; mobile phase: A: water+0.1% trifluoroacetic acid (TFA); B: acetonitrile+0.1% TFA; gradient: 5-100% B in 1.50 minutes; 100% B 0.20 min; flow: 0.8-1.0 mL/min in 1.50 minutes at 60° C.

MS-method: ESI positive

$^1$H-NMR. The signals are characterized by chemical shift (ppm) vs. tetramethylsilane, by their multiplicity and by their integral (relative number of hydrogen atoms given). The following abbreviations are used to characterize the multiplicity of the signals: m=multiplett, q=quartett, t=triplett, d=doublet and s=singulett.

log P determinations were performed via capillary electrophorese on a cePro9600™ from CombiSep.

Starting Materials 6,8-dichloro-1H-benzo[d][1,3]oxazine-2,4-dione and 6-chloro-8-methyl-1H-3,1-benzoxazine-2,4-dione were prepared according to WO 2007/43677

S,S-Diisopropyl-S-aminosulfonium 2,4,6-trimethylphenylsulfonat was prepared according to Y. Tamura et al, Tetrahedron, 1975, 31, 3035-3040.

Example P.1

S,S-Dimethyl sulfinium sulfate (Compound X with t=0 and $R^6=R^7=$methyl, $A^-=½\ SO_4^{2-}$)

To a solution of sodium methylate (15.76 g of a 30% solution in methanol, 87.54 mmol, 1.100 equiv.) in methanol (60 mL) was added dimethyl sulphide (5.44 g, 6.40 mL, 87.6 mmol, 1.10 equiv.) at −5-0° C. To this mixture was added a pre-cooled solution (−20° C.) of hydroxylamine-O-sulfonic acid (9.00 g, 79.6 mmol) in methanol (60 mL) and the internal temperature was maintained at −5-0° C. After stirring at room temperature over night, all solids were removed by filtration. The filtrate was concentrated in vacuo and the residue was triturated with acetonitrile (50 mL) to yield the title compound (7.88 g, 39%).

The following compounds were prepared by analogy to example P.1: S,S-diethyl sulfinium sulfate (Compound X with t=0 and $R^6=R^7=$ethyl, $A^-=½\ SO_4^{2-}$), S-ethyl-S-isopropyl sulfinium sulfate (Compound X with t=0 and $R^6=$ethyl, $R^7=$isopropyl, $A^-=½\ SO_4^{2-}$), S,S-diisopropyl sulfinium sulfate (Compound X with t=0 and $R^6=R^7=$isopropyl, $A^-=½\ SO_4^{2-}$), tetrahydro-$\lambda^4$-thiophen-1-ylamin mesitylsulfonate (Compound X with t=0 and $R^6$-$R^7=$1,4-butandiyl, $A^-=$2,4,6-trimethylphenylsulfonate) was prepared according to Y. Tamura et al, Tetrahedron, 1975, 31, 3035-3040, tetrahydro-$\lambda^4$-thiophen-1-ylamin sulfate (Compound X with t=0 and $R^6$-$R^7=$1,4-butandiyl, $A^-=½\ SO_4^{2-}$), $\lambda^4$-1,3-dithiolan-1-ylamin sulfate (Compound X with t=0 and $R^6$-$R^7=$2-thiabutan-1,4-diyl, $A^-=½\ SO_4^{2-}$), $\lambda^4$-thian-1-ylamin sulfate (Compound X with t=0 and $R^6$-$R^7=$pentan-1,5-diyl, $A^-=½\ SO_4^{2-}$), S,S-bis(cyclopropylmethyl) sulfinium sulfate (Compound X with t=0 and $R^6=R^7=$cyclopropylmethyl, $A^-=½\ SO_4^{2-}$), S,S-bis(2-cyclopropylethyl) sulfinium sulfate (Compound X with t=0 and $R^6=R^7=$2-cyclopropylethyl, $A^-=½\ SO_4^{2-}$), S,S-bis(cyclobutylmethyl) sulfinium sulfate (Compound X with t=0 and $R^6=R^7=$cyclobutylmethyl, $A^-=½\ SO_4^{2-}$), S,S-bis(cyclopentylmethyl) sulfinium sulfate (Compound X with t=0 and $R^6=R^7=$cyclopentylmethyl, $A^-=½\ SO_4^{2-}$), S-cyclopropylmethyl-S-ethyl sulfinium sulfate (Compound X with t=0 and $R^6=$ethyl, $R^7=$cyclopropylmethyl, $A^-=½\ SO_4^{2-}$), S-(2-cyclopropylethyl)-S-ethyl sulfinium sulfate (Compound X with t=0 and $R^6=$ethyl, $R^7=$2-cyclopropylethyl, $A^-=½\ SO_4^{2-}$), S-(2-cyclopropylethyl)-S-isopropyl sulfinium sulfate (Compound X with t=0 and $R^6=$2-propyl, $R^7=$2-cyclopropylethyl, $A^-=½\ SO_4^{2-}$), S-(1-cyclopropylethyl)-S-isopropyl sulfinium sulfate (Compound X with t=0 and $R^6=$2-propyl, $R^7=$1-cyclopropylethyl, $A^-=½\ SO_4^{2-}$), S-cyclobutylmethyl-S-ethyl sulfinium sulfate (Compound X with t=0 and $R^6=$ethyl, $R^7=$cyclobutylmethyl, $A^-=½\ SO_4^{2-}$), S-cyclopentylmethyl-S-ethyl sulfinium sulfate (Compound X with t=0 and $R^6=$ethyl, $R^7=$cyclopentylmethyl, $A^-=½\ SO_4^{2-}$), S-cyclopropylmethyl-S-isopropyl sulfinium sulfate (Compound X with t=0 and $R^6=$2-propyl, $R^7=$cyclopropylmethyl, $A^-=½\ SO_4^{2-}$), S-cyclobutylmethyl-S-isopropyl sulfinium sulfate (Compound X with t=0 and $R^6=$2-propyl, $R^7=$cyclobutylmethyl, $A^-=½\ SO_4^{2-}$), S-cyclopentylmethyl-S-isopropyl sulfinium sulfate (Compound X with t=0 and $R^6=$2-propyl, $R^7=$cyclopentylmethyl, $A^-=½\ SO_4^{2-}$), S,S-di-n-propyl sulfinium sulfate (Compound X with t=0 and $R^6=R^7=$n-propyl, $A^-=½\ SO_4^{2-}$), S-vinyl-S-ethyl sulfinium sulfate (Compound X with t=0 and $R^6=$ethyl, $R^7=$vinyl, $A^-=½\ SO_4^{2-}$), S,S-di-n-butyl sulfinium sulfate (Compound X with t=0 and $R^6=R^7=$n-butyl, $A^-=½\ SO_4^{2-}$), S,S-di-n-pentyl sulfinium sulfate (Compound X with t=0 and $R^6=R^7=$n-pentyl, $A^-=½\ SO_4^{2-}$), S,S-di-n-hexyl sulfinium sulfate (Compound X with t=0 and $R^6=R^7=$n-hexyl, $A^-=½\ SO_4^{2-}$), S,S-bis(2-ethylhexyl) sulfinium sulfate (Compound X with t=0 and $R^6=R^7=$2-ethylhexyl, $A^-=½\ SO_4^{2-}$), S,S-bis(3-methyl-2-butyl) sulfinium sulfate (Compound X with t=0 and $R^6=R^7=$3-methyl-2-butyl, $A^-=½\ SO_4^{2-}$), S,S-bis(3-methyl-1-butyl) sulfinium sulfate (Compound X with t=0 and $R^6=R^7=$3-methyl-1-butyl, $A^-=½\ SO_4^{2-}$), S,S-bis(2-methylpropyl) sulfinium sulfate (Compound X with t=0 and $R^6=R^7=$2-methylpropyl, $A^-=½\ SO_4^{2-}$), S-isopropyl-S-methyl sulfinium sulfate (Compound X with t=0 and $R^6=$methyl, $R^7=$isopropyl $A^-=½\ SO_4^{2-}$), S-2-butyl-S-methyl sulfinium sulfate (Compound X with t=0 and $R^6=$methyl, $R^7=$2-butyl, $A^-=½\ SO_4^{2-}$), S-3-Methyl-2-butyl-S-methyl sulfinium sulfate (Compound X with t=0 and $R^6=$methyl, $R^7=$3-Methyl-2-butyl $A^-=½\ SO_4^{2-}$), S-3-Methyl-2-butyl-S-ethyl sulfinium sulfate (Compound X with t=0 and $R^6=$ethyl, $R^7=$3-Methyl-2-butyl $A^-=½\ SO_4^{2-}$), S-3-Methyl-2-butyl-S-isopropyl sulfinium sulfate (Compound X with t=0 and $R^6=$2-propyl, $R^7=$3-Methyl-2-butyl $A^-=½\ SO_4^{2-}$), S,S-bis(2-hydroxyethyl) sulfinium sulfate (Compound X with t=0 and $R^6=R^7=$2-hydroxyethyl, $A^-=½\ SO_4^{2-}$), S-(4-Fluorophenyl)-S-methyl sulfinium sulfate (Compound X with t=0 and $R^6=$methyl, $R^7=$4-fluorophenyl, $A^-=½\ SO_4^{2-}$), S-n-pentyl-S-2-hydroxyethyl sulfinium sulfate (Compound X with t=0 and $R^6=$n-pentyl, $R^7=$2-hydroxyethyl, $A^-=½\ SO_4^{2-}$), S-ethyl-S-cyclopropyl sulfinium sulfate (Compound X with t=0 and $R^6=$ethyl, $R^7=$cyclopropyl, $A^-=½\ SO_4^{2-}$), S-2-propyl-S-cyclopropyl sulfinium sulfate (Compound X with t=0 and $R^6=$2-propyl, $R^7=$cyclopropyl, $A^-=½\ SO_4^{2-}$), S-methyl-S-ethyl sulfinium sulfate (Compound X with t=0 and $R^6=$methyl, $R^7=$ethyl, $A^-=½\ SO_4^{2-}$), S-methyl-S-n-propyl sulfinium sulfate (Compound X with t=0 and $R^6=$methyl, $R^7=$n-propyl, $A^-=½\ SO_4^{2-}$), S-(2-chloroethyl)-S-ethyl sulfinium sulfate (Compound X with t=0 and $R^6=$2-chloroethyl, $R^7=$ethyl, $A^-=½\ SO_4^{2-}$).

Example P.2

8-Bromo-6-chloro-1H-benzo[d][1,3]oxazine-2,4-dione

To a solution of 2-amino-3-bromo-5-chlorobenzoic acid (10.0 g, 39.9 mmol) in dioxane (170 mL) was added phosgene (20% in toluene, 42.0 mL, 79.9 mmol) over a period of 15 mins. The reaction was stirred at ambient temperature for 48 h and then concentrated in vacuo. The resulting solid was crushed and further dried in vacuo to yield the desired product (12.6 g, 114%) which was used in the subsequent step without further purification.

The following compounds were prepared by analogy to example P.2:
6,8-dichloro-1H-benzo[d][1,3]oxazine-2,4-dione,
6,8-dibromo-1H-benzo[d][1,3]oxazine-2,4-dione,
6-Bromo-8-chloro-1H-benzo[d][1,3]oxazine-2,4-dione,
8-Bromo-6-chloro-1H-benzo[d][1,3]oxazine-2,4-dione,
6-chloro-8-methyl-1H-benzo[d][1,3]oxazine-2,4-dione,
6-bromo-8-methyl-1H-benzo[d][1,3]oxazine-2,4-dione,
6-cyano-8-methyl-1H-benzo[d][1,3]oxazine-2,4-dione,
6-chloro-8-trifluoromethyl-1H-benzo[d][1,3]oxazine-2,4-dione,
8-chloro-6-trifluoromethyl-1H-benzo[d][1,3]oxazine-2,4-dione,
6-bromo-8-trifluoromethyl-1H-benzo[d][1,3]oxazine-2,4-dione,
8-bromo-6-trifluoromethyl-1H-benzo[d][1,3]oxazine-2,4-dione,
8-chloro-6-cyano-1H-benzo[d][1,3]oxazine-2,4-dione,
6-chloro-8-methoxy-1H-benzo[d][1,3]oxazine-2,4-dione,
6-chloro-8-cyclopropyl-1H-benzo[d][1,3]oxazine-2,4-dione,
6-chloro-8-ethyl-1H-benzo[d][1,3]oxazine-2,4-dione,
6-difluoromethoxy-8-methyl-1H-benzo[d][1,3]oxazine-2,4-dione,
6-cyano-8-methoxy-1H-benzo[d][1,3]oxazine-2,4-dione,
6-fluoro-8-methyl-1H-benzo[d][1,3]oxazine-2,4-dione,
6-iodo-8-methyl-1H-benzo[d][1,3]oxazine-2,4-dione,
6-nitro-8-methyl-1H-benzo[d][1,3]oxazine-2,4-dione,
6-(5-chloro-2-thienyl)-8-methyl-1H-benzo[d][1,3]oxazine-2,4-dione,
6-(3-pyrazol-1H-yl)-8-methyl-1H-benzo[d][1,3]oxazine-2,4-dione,
6-(3-isoxazolyl)-8-methyl-1H-benzo[d][1,3]oxazine-2,4-dione,
6-(hydroxyiminomethyl)-8-methyl-1H-benzo[d][1,3]oxazine-2,4-dione,
6-(methoxyiminomethyl)-8-methyl-1H-benzo[d][1,3]oxazine-2,4-dione,
6-(dimethylhydrazonomethyl)-8-methyl-1H-benzo[d][1,3]oxazine-2,4-dione and
6-(2,2,2-trifluoroethylhydrazonomethyl)-8-methyl-1H-benzo[d][1,3]oxazine-2,4-dione.

Example P.3

1-(3-chloro-2-pyridyl)-3-trifluoromethyl-1H-pyrazol a) 2.71 kg of 1,1,1-trifluoro-4-methoxy-but-3-en-2-on, 2.44 kg of ethanol and 3.10 kg of water were charged into a reaction vessel. 20 ml of concentrated hydrochloric acid and 0.80 kg of hydrazine hydrate were successively added and the mixture was heated to reflux for 4 h. The mixtures was allowed to cool and neutralized by addition of 10% aqueous NaOH to about pH 4-5. Then the mixture was evaporated. Toluene was added and the mixture was again evaporated to yield 2 kg of raw 3-trifluoromethylpyrazole with a purity of >85%.

b) 1.72 kg (10.75 mol) of the raw 3-trifluoromethylpyrazole obtained in step a), 1.75 kg (11.83 mol) of 2,3-dichloropyridine and 4.73 kg of dimethyl formamide were charged to a reaction vessel. 2.97 kg (21.50 mol) of potassium carbonate were added, the mixture was heated to 120° C. with stirring and kept at 120-125° C. for further 3 h. The reaction mixtures was cooled to 25° C. and poured into 20 l of water. The thus obtained mixture was extracted twice with 5 L of tert.-butyl-methyl ether. The combined organic phases were washed with 4 l of water and then evaporated to dryness. Toluene was added and the mixture was again evaporated to dryness. Thereby, the 2.7 kg of the title compound was obtained (purity>75% as determined by GC; yield 81.5%). The product can be purified by distillation.

Characterization by $^1$H-NMR (400 MHz, CDCl$_3$): δ [delta]=6.73 (d, 1H), 7.38 (d, 1H), 7.95 (m, 1H), 8.14 (m, 1H), 8.46 (m, 1H).

Preparation of the Compounds of Formula (VII)

Example P.4

2-amino-5-chloro-N-(dimethyl-$\lambda^4$-sulfanylidene)-3-methyl-benzamide

To a solution of 6-chloro-8-methyl-1H-3,1-benzoxazine-2,4-dione (3.00 g, 12.8 mmol) in dichloromethane (40 mL) was added dimethyl sulfinium sulfate (2.25 g, 8.93 mmol, 0.70 equiv.) and potassium tert-butylate (1.58 g, 14.0 mmol, 1.10 equiv.) at room temperature. The mixture was stirred for 1.5 h, upon which water was added and the layers were separated. The aqueous layer was extracted with dichloromethane, combined organic layers were dried over sodium sulphate and concentrated in vacuo. The residue was purified by flash-chromatography on silica gel to yield the title compound (2.63 g, 84%).

Characterization by HPLC-MS: 1.855 min, M=245.00.

Example P.5

2-amino-5-chloro-N-(bis-2-propyl-$\lambda^4$-sulfanylidene)-3-methyl-benzamide To a solution of 6-chloro-8-methyl-1H-3,1-benzoxazine-2,4-dione (3.00 g, 12.8 mmol) in dichloromethane (40 mL) was added bis-2-propyl sulfinium sulfate (3.76 g, 8.93 mmol, 0.70 equiv.) and potassium tert-butylate (1.58 g, 14.0 mmol, 1.10 equiv.) at room temperature. The mixture was stirred for 1.5 h, upon which water was added and the layers were separated. The aqueous layer was extracted with dichloromethane, combined organic layers were dried over sodium sulphate and concentrated in vacuo. The residue was purified by flash-chromatography on silica gel to yield the title compound (2.89 g, 69%).

Characterization by UPLC-MS: 1.044 min, M=329.1;
Characterization by $^1$H-NMR (400 MHz, DMSO-d$_6$): δ [delta]=1.04 (m, 12H), 2.06 (s, 3H), 2.96 (m, 2H), 3.01 (m, 2H), 6.62 (br. s, 2H), 7.03 (s, 1H), 7.72 (s, 1H).

Example P.6a

2-amino-5-chloro-N-(bis-2-methylpropyl-$\lambda^4$-sulfanylidene)-3-methyl-benzamide To a solution of 6-chloro-8-methyl-1H-3,1-benzoxazine-2,4-dione (3.00 g, 12.8 mmol) in dichloromethane (40 mL)

was added bis-2-methylpropyl sulfinium sulfate (3.76 g, 8.93 mmol, 0.70 equiv.) and potassium tert-butylate (1.58 g, 14.0 mmol, 1.10 equiv.) at room temperature. The mixture was stirred for 1.5 h, upon which water was added and the layers were separated. The aqueous layer was extracted with dichloromethane, combined organic layers were dried over sodium sulphate and concentrated in vacuo. The residue was purified by flash-chromatography on silica gel to yield the title compound (2.89 g, 69%).

Characterization by $^1$H-NMR (400 MHz, DMSO-$d_6$): δ [delta]=1.04 (m, 12H), 2.06 (s, 3H), 2.96 (m, 2H), 3.01 (m, 2H), 6.62 (br. s, 2H), 7.03 (s, 1H), 7.72 (s, 1H).

Example P.6b 2-amino-5-chloro-N-(bis-2-methylpropyl-$\lambda^4$-sulfanylidene)-3-methyl-benzamide To a solution of 6-chloro-8-methyl-1H-3,1-benzoxazine-2,4-dione (12.17 g, 0.06 mol) in anhydrous DMSO (100 mL) was added bis-2-methylpropyl sulfinium sulfate (14.56 g, 0.04 mol, 0.70 equiv.) and triethyl amine (9.19 mL, 6.67 g, 0.07 mol, 1.15 equiv.) at room temperature. The mixture was stirred for 4.5 h, and then added dropwise to ice-water. The mixture was extracted with dichloromethane and the combined organic layers were dried over sodium sulphate and concentrated in vacuo. The residue was triturated with ether to yield the title compound (8.3 g, 46%).

Characterization by $^1$H-NMR (400 MHz, DMSO-$d_6$): δ [delta]=1.04 (m, 12H), 2.06 (s, 3H), 2.96 (m, 2H), 3.01 (m, 2H), 6.62 (br. s, 2H), 7.03 (s, 1H), 7.72 (s, 1H).

Example P.7

2-amino-5-chloro-N-(diethyl-$\lambda^4$-sulfanylidene)-3-methyl-benzamide

To a solution of 6-chloro-8-methyl-1H-3,1-benzoxazine-2,4-dione (2 g, 0.01 mol) in anhydrous propylene carbonate (30 mL) was added bis-2-ethyl sulfinium sulfate (2.04 g, 0.01 mol, 0.70 equiv.) and triethyl amine (1.38 mL, 1.0 g g, 0.01 mol, 1.05 equiv.) at room temperature. The mixture was stirred for 4.5 h, and then added dropwise to ice-water. The mixture was extracted with dichloromethane and the combined organic layers were dried over sodium sulphate and concentrated in vacuo. The residue was triturated with ether to yield the title compound (1.43 g, 55%).

Characterization by $^1$H-NMR (400 MHz, CDCl$_3$): δ [delta]=1.39 (t, 6H), 2.13 (s, 3H), 3.02 (q, 4H), 5.95 (br. S, 2H), 7.01 (s, 1H), 7.98 (s, 1H).

Example P.8

2-amino-3,5-dichloro-N-(bis-2-methylpropyl-$\lambda^4$-sulfanylidene)-benzamide

The title compound was prepared by analogy to the method of example P.7.

Yield: 60%

Characterization by $^1$H-NMR (400 MHz, DMSO-$d_6$): δ [delta]=1.23 (d, 6H), 1.38 (d, 6H), 3.42 (m, 2H), 7.02 (br. s, 2H), 7.41 (s, 1H), 7.95 (s, 1H).

By the methods described in examples P.4 to P.8 the compounds P.9 to P.30 of formula VII-1, which are compounds of formula VIIa with t=0 and $R^5$=H, were prepared, as summarized in the following table C.1:

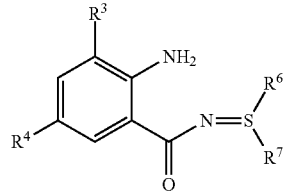

(VIIa-1)

TABLE C.1 compounds of formula VIIa-1

| Ex. | $R^6$ | $R^7$ | $R^3$ | $R^4$ | HPLC/MS (Method) |
|---|---|---|---|---|---|
| P.9 | $C_2H_5$ | $C_2H_5$ | $CH_3$ | Cl | 2.159 min, m/z = 273.0 (A) |
| P.10 | $CH_2CH(CH_3)_2$ | $CH_2CH(CH_3)_2$ | Cl | Cl | |
| P.11 | $CH(CH_3)_2$ | $CH(CH_3)_2$ | Cl | Cl | 3.346 min, m/z = 321.05 (A) |
| P.12 | $C_2H_5$ | $C_2H_5$ | Cl | Cl | 2.821 min, m/z = 292.9 (A) |
| P.13 | $CH_2$—c-Pr | $CH_2$—c-Pr | $CH_3$ | Cl | 1.191 min, m/z = 325.5 (B) |
| P.14 | $CH_2$—c-Pr | $CH_2$—c-Pr | Cl | Cl | 1.391 min, m/z = 320.8 (B) |
| P.15 | $CH_2$—c-Pr | $C_2H_5$ | $CH_3$ | Cl | 1.197 min, m/z = 299.1 (B) |
| P.16 | $CH_2$—c-Pr | $CH(CH_3)_2$ | Cl | Cl | 3.200 min, m/z = 333.0 (A) |
| P.17 | $CH_2$—c-Pr | $CH(CH_3)_2$ | $CH_3$ | Cl | 2.433 min, m/z = 313.0 (A) |
| P.18 | $C_2H_5$ | $C_2H_5$ | $CF_3$ | Cl | 3.218 min, m/z = 327.00 (A) |
| P.19 | $C_2H_5$ | $C_2H_5$ | $CF_3$ | Br | 3.291 min, m/z = 372.90 (A) |
| P.20 | $C_2H_5$ | $C_2H_5$ | Br | Cl | 2.980 min, m/z = 338.90 (A) |
| P.21 | $C_2H_5$ | $C_2H_5$ | Cl | Br | 2.970 min, m/z = 338.90 (A) |
| P.22 | $CH(CH_3)_2$ | $CH(CH_3)_2$ | $CF_3$ | Cl | 3.604 min, m/z = 355.05 (A) |
| P.23 | $CH(CH_3)_2$ | $CH(CH_3)_2$ | $CF_3$ | Br | 3.677 min, m/z = 400.95 (A) |
| P.24 | $CH(CH_3)_2$ | $CH(CH_3)_2$ | Br | Cl | 3.390 min, m/z = 366.95 (A) |
| P.25 | $CH(CH_3)_2$ | $CH(CH_3)_2$ | Cl | Br | 3.381 min, m/z = 366.95 (A) |
| P.26 | $CH(CH_3)_2$ | $CH(CH_3)_2$ | Br | Br | 3.409 min, m/z = 410.90 (A) |
| P.27 | $CH_2CH_2CH_3$ | $CH_2CH_2CH_3$ | $CH_3$ | Cl | 1.046 min, m/z = 301.1 (B) |
| P.28 | $CH_2CH_2CH_3$ | $CH_2CH_2CH_3$ | Cl | Cl | 3.441 min, m/z = 320.95 (A) |
| P.29 | $C_2H_5$ | $C_2H_5$ | Br | Br | 1.102 min, m/z = 383.0 (B) |
| P.30 | $CH(CH_3)_2$ | $CH(CH_3)_2$ | $CH_3$ | Cl | 2.510 min, m/z = 301.05 (A) |

$CH_2$—c-Pr = $CH_2$-cyclopropyl

By the methods described in examples P.4 to P.8 the compounds P.31 to P.165 of formula VIIa-1, summarized in the following table C.2, can be prepared. In table C.2 the following abbreviations are used:
mp: melting point
$R^4$-1: CH(=N—OCH$_3$)
$R^4$-2: 3-pyrazol-1H-yl
$R^4$-3: CH(=N—NHCH$_2$CF$_3$)
$R^4$-4: CH[=N—N(CH$_3$)$_2$]
Me: Methyl
OMe: Methoxy
Et: Ethyl
i-Pr: isopropyl
i-Bu: isobutyl
3-Me-2-Bu: 3-methyl-2-butyl
3-Me-1-Bu: 3-methyl-1-butyl n-Bu: n-butyl
2-Bu: 2-butyl
n-Pe: n-pentyl
n-Hex: n-hexyl
2-EtHex: 2-ethylhexyl
c-Pr: cyclopropyl
c-Bu: cyclobutyl
c-Pe: cyclopentyl
2-Cl-5-Tp: 2-chloro-5-thiophenyl
4-F-Ph: 4-fluorophenyl

TABLE C.2 compounds of formula VIIa-1 (compounds P. 31 to S. 165)

| Cpd. | $R^6$ | $R^7$ | $R^3$ | $R^4$ |
|---|---|---|---|---|
| P.31 | Et | Et | Me | $NO_2$ |
| P.32 | Et | Et | Me | 2-Cl-5-Tp |
| P.33 | $CH_2$—c-P | Et | Me | Cl |
| P.34 | 3-Me-2-Bu | 3-Me-2-Bu | Cl | Cl |
| P.35 | i-Bu | i-Bu | OMe | CN |
| P.36 | Me | n-Pr | Me | Cl |
| P.37 | $CH_2$-c-Pe | $CH_2$-c-Pe | Me | Cl |
| P.38 | Et | Et | Me | F |
| P.39 | Et | $CH_2$—c-Bu | Cl | Cl |
| P.40 | 4-F—Ph | Me | Me | CN |
| P.41 | $CH_2CH_2SCH_2$ | | Me | Cl |
| P.42 | n-Hex | n-Hex | Me | Cl |
| P.43 | $CH_2CH_2OH$ | $CH_2CH_2OH$ | Cl | Cl |
| P.44 | i-Pr | i-Pr | Br | $CF_3$ |
| P.45 | 3-Me-2-Bu | 3-Me-2-Bu | Me | Cl |
| P.46 | i-Pr | i-Pr | Me | Cl |
| P.47 | $(CH_2)_2$—c-Pr | $(CH_2)_2$—c-Pr | Me | CN |
| P.48 | i-Pr | i-Pr | Cl | CN |
| P.49 | i-Pr | i-Pr | Me | F |
| P.50 | n-Pe | n-Pe | Me | CN |
| P.51 | 3-Me-1-Bu | 3-Me-1-Bu | Me | Cl |
| P.52 | i-Pr | c-Pr | Cl | Cl |
| P.53 | Me | Me | Me | I |
| P.54 | $CH_2$—c-Pr | i-Pr | Cl | CN |
| P.55 | Et | Me | Me | I |
| P.56 | Et | Et | Me | CH(=N—OH) |
| P.57 | $CH_2$-c-Pe | $CH_2$-c-Pe | Cl | Cl |
| P.58 | Et | c-Pr | Cl | Cl |
| P.59 | $CH_2$-c-Pt | Et | Me | CN |
| P.60 | $CH_2CH_2CH_2CH_2$ | | Me | CN |
| P.61 | $CH_2$—c-Bu | Et | Me | CN |
| P.62 | Et | c-Pr | Me | Cl |
| P.63 | $CH_2$—c-Bu | $CH_2$—c-Bu | Me | CN |
| P.64 | Me | Me | c-Pr | Cl |
| P.65 | $(CH_2)_2$—c-Pr | Et | Me | Cl |
| P.66 | i-Pr | i-Pr | OMe | Cl |
| P.67 | n-Pe | $CH_2CH_2OH$ | Me | Cl |
| P.68 | Et | Et | Me | $R^4$-1 |
| P.69 | Et | i-Pr | Cl | Cl |
| P.70 | 2-EtHex | 2-EtHex | Cl | Cl |
| P.71 | i-Pr | i-Bu | Cl | Cl |
| P.72 | Et | Et | Me | CN |
| P.73 | $CH_2$-c-Pe | i-Pr | Me | Cl |
| P.74 | $CH_2$-c-Pe | i-Pr | Cl | Cl |
| P.75 | n-Hex | n-Hex | Me | CN |
| P.76 | Et | $CH_2CH_2$—c-Pr | Me | CN |
| P.77 | Et | Et | Me | $R^4$-2 |
| P.78 | Et | Et | c-Pr | Cl |
| P.79 | $CH_2$-c-Pe | Et | Cl | Cl |
| P.80 | $CH_2$—c-Pr | $CH_2$—c-Pr | Cl | CN |
| P.81 | $CH_2CH_2CH_2CH_2$ | | Me | Cl |
| P.82 | $CH_2$—c-BuI | i-Pr | Me | CN |
| P.83 | Et | CH=$CH_2$ | Me | CN |
| P.84 | n-Pe | n-Pe | Me | Cl |
| P.85 | Et | Et | Me | Br |
| P.86 | Me | Me | Me | CN |
| P.87 | $CH_2CH_2CH_2CH_2CH_2$ | | Me | I |
| P.88 | $CH_2CH_2CH_2CH_2CH_2$ | | Me | CN |
| P.89 | Et | Et | Me | 3-isoxazolyl |
| P.90 | i-Pr | $(CH_2)_2$—c-Pr | Me | Cl |
| P.91 | i-Pr | i-Pr | Et | Cl |
| P.92 | Et | Et | Et | Cl |
| P.93 | i-Pr | c-Pr | Me | Cl |
| P.94 | $CH_2CH_2CH_2CH_2$ | | Br | Cl |
| P.95 | Et | Et | Br | $CF_3$ |
| P.96 | i-Pr | i-Pr | Me | $NO_2$ |
| P.97 | 3-Me-2-Bu | Et | Cl | Cl |
| P.98 | $(CH_2)_2$—c-Pr | i-Pr | Me | CN |
| P.99 | Et | Et | Me | Cl |
| P.100 | i-Pr | i-Pr | Me | 3-isoxazolyl |
| P.101 | $CH_2CH_2OH$ | n-Pe | Me | CN |
| P.102 | $(CH_2)_2$—c-Pr | Et | Cl | Cl |
| P.103 | Me | 4-F—Ph | Me | Cl |
| P.104 | i-Pr | i-Pr | Cl | CH(=N—OH) |
| P.105 | $CH_2$—c-Bu | i-Pr | Cl | Cl |
| P.106 | Me | n-Pr | Me | I |
| P.107 | i-Bu | i-Bu | c-Pr | Cl |
| P.108 | 2-EtHex | 2-EtHex | Me | CN |
| P.109 | Et | Et | Me | $R^4$-3 |
| P.110 | 2-Bu | Me | Me | Cl |
| P.111 | $CH_2CH_2SCH_2$ | | Me | CN |
| P.112 | $(CH_2)_2$—c-Pr | i-Pr | Me | Cl |
| P.113 | Me | 4-Fl—Ph | Me | I |
| P.114 | $(CH_2)_2$—c-Pr | $(CH_2)_2$—c-Pr | Cl | Cl |
| P.115 | n-Pe | n-Pe | Cl | Cl |
| P.116 | i-Pr | $CH(CH_3)$—c-Pr | Cl | Cl |
| P.117 | 3-Me-1-Bu | 3-Me-1-Bu | Me | CN |
| P.118 | $(CH_2)_2$—c-Pr | $(CH_2)_2$—c-Pr | Me | Cl |
| P.119 | i-Pr | i-Pr | Me | CH(=N—OH) |
| P.120 | Me | Me | OMe | Cl |
| P.121 | 2-EtHex | 2-EtHex | Me | Cl |
| P.122 | Et | Et | Cl | CN |
| P.123 | n-Pe | $CH_2CH_2OH$ | Me | I |
| P.124 | Me | Me | Et | Cl |
| P.125 | $CH_2$-c-Bu | i-Pr | Me | Cl |
| P.126 | $(CH_2)_2$—c-Pr | i-Pr | Cl | Cl |
| P.127 | i-Bu | i-Bu | Et | Cl |
| P.128 | n-Hex | n-Hex | Cl | Cl |
| P.129 | i-Pr | i-Pr | Me | I |
| P.130 | $CH_2CH_2OH$ | $CH_2CH_2OH$ | Me | CN |
| P.131 | 2-Bu | Me | Me | CN |
| P.132 | $CH_2CH_2Cl$ | Et | Me | I |
| P.133 | $CH_2$—c-Pr | Et | Cl | CN |
| P.134 | $CH_2$-c-Bu | $CH_2$—c-Bu | Cl | Cl |
| P.135 | $CH_2CH_2SCH_2$ | | Cl | Cl |
| P.136 | $CH_2CH_2SCH_2$ | | Me | I |
| P.137 | Me | Et | Me | CN |
| P.138 | Et | Et | Cl | CH(=N—OH) |
| P.139 | $CH_2CH_2CH_2CH_2$ | | Cl | Cl |
| P.140 | Et | i-Pr | Me | Cl |
| P.141 | i-Bu | i-Bu | OMe | Cl |
| P.142 | Me | Me | OMe | CN |
| P.143 | $CH_2$—c-Bu | Et | Me | Cl |
| P.144 | $CH_2CH_2CH_2CH_2$ | | Me | I |
| P.145 | $CH_2$—c-Pr | Et | Cl | Cl |
| P.146 | i-Pr | i-Pr | Cl | $CF_3$ |
| P.147 | $CH_2CH_2OH$ | $CH_2CH_2OH$ | Me | Cl |
| P.148 | $CH_2$-c-Pe | $CH_2$-c-Pe | Me | CN |
| P.149 | Et | Et | Cl | $CF_3$ |
| P.150 | Et | Et | OMe | Cl |
| P.151 | i-Pr | i-Pr | Me | Br |
| P.152 | Et | Et | Me | $R^4$-4 |
| P.153 | i-Pr | i-Pr | Me | 2-Cl-5-Tp |
| P.154 | Et | 3-Me-2-Bu | Me | Cl |
| P.155 | i-Pr | i-Pr | Me | CN |
| P.156 | Et | Me | Me | Cl |
| P.157 | $CH_2$-c-Pe | i-Pr | Me | CN |
| P.158 | i-Pr | i-Pr | c-Pr | Cl |
| P.159 | $CH_2$—c-Bu | $CH_2$—c-Bu | Me | Cl |
| P.160 | i-Pr | 3-Me-2-Bu | Me | Cl |
| P.161 | Me | Me | Cl | Cl |
| P.162 | 3-Me-1-Bu | 3-Me-1-Bu | Cl | Cl |
| P.163 | i-Pr | 3-Me-2-Bu | Cl | Cl |
| P.164 | n-Pr | Me | Me | CN |
| P.165 | Me | Me | $OCHF_2$ | Cl |

PREPARATION EXAMPLES

Preparation of the Compounds of Formula (I)
(Examples S.1 to S.7)

Example S.1a 2-(3-Chloropyridin-2-yl)-5-trifluoromethyl-2H-pyrazole-3-carbonyl chloride In a reaction vessel equipped with a thermometer, septum, nitrogen inlet and stirring bar, 500 mg (2.02 mmol) of 1-(3-chloro-2-pyridyl)-3-trifloromethyl-1H-pyrazole were dissolved in 3 ml of dry tetrahydrofurane. By means of a syringe, 2.0 ml of a 2 M solution of isopropyl magnesium chloride in tetrahydrofurane were added dropwise with stirring, while cooling the vessel with an ice bath and keeping the internal temperature at about 20° C. The ice bath was removed and the mixture was stirred for further 20 minutes at 23° C. Then the mixture was cooled again to −5° C. and 4.25 ml of a 20% (w/w) solution of phosgene in toluene were added dropwise with stirring. The mixture was allowed to war at 23° C. and stirred for further 1 h at 23° C. The thus obtained reaction mixture was evaporated to dryness, redissolved in toluene and stirred for further 30 min. at 50° C. Solids were removed by filtration and washed with toluene. The combined filtrates were evaporated to dryness to yield 0.53 g of the title compound with a purity>85% (yield 84.6%).

Characterization by $^1$H-NMR (400 MHz, CDCl$_3$): δ [delta]=7.43-7.54 (m, 2H), 7.93 (d, 1H), 8.52 (m, 1H).

Example S.1b 2-(3-Chloropyridin-2-yl)-5-trifluoromethyl-2H-pyrazole-3-carbonyl chloride In a reaction vessel equipped with a thermometer, septum, nitrogen inlet and stirring bar 1-(3-chloro-2-pyridyl)-3-methoxy-1H-pyrazole (2.00 g, 8.08 mmol) were dissolved in dry tetrahydrofuran (15 mL) and cooled to 0° C. By means of a syringe isopropyl magnesium chloride (8.1 mL of a 2 M solution in tetrahydrofuran, 16 mmol, 2.0 equiv.) was added dropwise with stirring, while cooling the vessel with an ice bath and keeping the internal temperature below 5° C. After 3 h at this temperature, the reaction mixture was dropwise transferred to a pre-cooled solution of a 20% (w/w) solution of phosgene in toluene (13 mL) while keeping the temperature below 0-5° C. After 15 min, the ice-bath was removed and the thus obtained reaction mixture was evaporated to dryness, redissolved in dichloromethane and stirred for further 5 min. Solids were removed by filtration and washed with dichloromethane. The combined filtrates were evaporated to dryness to yield the title compound (2.66 g, 106%) which was used in the next step without further purification.

Characterization by $^1$H-NMR (400 MHz, CDCl$_3$): δ [delta]=7.43-7.54 (m, 2H), 7.93 (d, 1H), 8.52 (m, 1H).

Example S.1c 2-(3-Chloropyridin-2-yl)-5-trifluoromethyl-2H-pyrazole-3-carbonyl chloride In a reaction vessel equipped with a thermometer, septum, nitrogen inlet and stirring bar 1-(3-chloro-2-pyridyl)-3-methoxy-1H-pyrazole (2.00 g, 8.08 mmol) were dissolved in dry tetrahydrofuran (15 mL) and cooled to 0° C. By means of a syringe isopropyl magnesium chloride complex with lithium chloride (12.4 mL of a 1.3 M solution in tetrahydrofuran, 16 mmol, 2.0 equiv.) was added dropwise with stirring, while cooling the vessel with an ice bath and keeping the internal temperature below 20° C. After 1 h at this temperature, the reaction mixture was dropwise transferred to a pre-cooled solution of a 20% (w/w) solution of phosgene in toluene (13 mL) while keeping the temperature below 5° C. After 2 min, the ice-bath was removed and the thus obtained reaction mixture was evaporated to dryness, redissolved in dichloromethane and stirred for further 5 min. Solids were removed by filtration and washed with dichloromethane. The combined filtrates were evaporated to dryness to yield the title compound (1.75 g, 70%) which was used in the next step without further purification.

Characterization by $^1$H-NMR (400 MHz, CDCl$_3$): δ [delta]=7.43-7.54 (m, 2H), 7.93 (d, 1H), 8.52 (m, 1H).

Example S.2

2-(3-Chloropyridin-2-yl)-5-methoxy-2H-pyrazole-3-carbonyl chloride

In a reaction vessel equipped with a thermometer, septum, nitrogen inlet and stirring bar 1-(3-chloro-2-pyridyl)-3-triflo-romethyl-1H-pyrazole (2.0 g, 0.01 mol) were dissolved in dry 1,2-dimethoxyethane (15 mL) and cooled to 0° C. By means of a syringe isopropyl magnesium chloride (11.4 mL of a 2 M solution in tetrahydrofuran) was added dropwise with stirring, while cooling the vessel with an ice bath and keeping the internal temperature below 5° C. After 3 h at this temperature a 20% (w/w) solution of phosgene in toluene (17 mL) were added dropwise with stirring. The mixture was allowed to warm to 23° C. and stirred for further 1 h at room temperature. The thus obtained reaction mixture was evaporated to dryness, redissolved in toluene and stirred for further 30 min. at 50° C. Solids were removed by filtration and washed with toluene. The combined filtrates were evaporated to dryness to yield 0.63 g of the title compound which was used in the next step without further purification.

Characterization of the corresponding hydrolysis product (carboxylic acid) by UPLC-MS: 1.170 min, M=218

The following compounds were/can be prepared by analogy to examples S.1a to S.1c or S.2:

Example S.3

2-(3-Chloropyridin-2-yl)-5-bromo-2H-pyrazole-3-carbonyl chloride

Example S.4

2-(3-Trifluoromethyl-pyridin-2-yl)-5-trifluoromethyl-2H-pyrazole-3-carbonyl chloride

Example S.5

2-(3-Chloropyridin-2-yl)-5-difluoromethyl-2H-pyrazole-3-carbonyl chloride

Example S.6

2-(3-Trifluoromethyl-pyridin-2-yl)-5-difluoromethyl-2H-pyrazole-3-carbonyl chloride

Example S.7

2-(3-Trifluoromethyl-pyridin-2-yl)-5-methoxy-2H-pyrazole-3-carbonyl chloride

Preparation of the Compounds of Formula (VI)
(Examples 1 to 225)

Example 1a 2-(3-chloro-2-pyridyl)-N-[2,4-dichloro-6-[(diethyl-$\lambda^4$-sulfanylidene)carbamoyl]phenyl]-5-(trifluoromethyl)pyrazole-3-carboxamide To a solution of 2-amino-3,5-dichloro-N-(diethyl-sulfanylidene)benzamide (8.82 g, 25.6 mmol) in pyridine (30 mL) was added N,N-dimethylamino pyridine (312 mg, 2.56 mmol, 10.0 mol %). At 90° C., a solution of 2-(3-chloro-2-pyridyl)-5-(trifluoromethyl)pyrazole-3-carbonyl chloride (10.90 g, 29.12 mmol, 1.100 equiv.) in pyridine (50 mL) was added dropwise and the mixture was stirred for 1 h. The mixture was cooled and concentrated in vacuum. Water was added and the mixture was extracted with ethyl acetate. Combined organic layers were washed with water and brine, dried over sodium sulphate, filtered and concentrated in vacuum. Flash-chromatography on silica gel yielded the title compound (4.12 g, 28%).

Characterization by $^1$H-NMR (400 MHz, DMSO-$d_6$): δ [delta]=1.13 (t, 6H), 2.91 (m, 2H), 3.08 (m, 2H), 7.67 (dd, 1H), 7.77 (s, 2H), 7.89 (s, 1H), 8.22 (d, 1H), 8.51 (d, 1H), 10.73 (s, 1H).

Example 1b 2-(3-chloro-2-pyridyl)-N-[2,4-dichloro-6-[(diethyl-$\lambda^4$-sulfanylidene)carbamoyl]phenyl]-5-(trifluoromethyl)pyrazole-3-carboxamide To a suspension of potassium carbonate (7.78 g, 56.3 mmol, 1.10 equiv.) and 2-amino-3,5-dichloro-N-(diethyl-$\lambda^4$-sulfanylidene)benzamide (15.00 g, 51.16 mmol) in toluene (50 mL) was added a solution of 2-(3-chloro-2-pyridyl)-5-(trifluoromethyl)-pyrazole-3-carbonyl chloride (17.62 g, 51.15 mmol, 1.000 equiv.) in toluene (55 mL) at 60° C. After 1.5 h at this temperature, the mixture was cooled and water was added. The resulting precipitate was collected by filtration, washed with water and petrol ether and dried to obtain the title compound (18.73 g, 65%).

Characterization by $^1$H-NMR (400 MHz, DMSO-$d_6$): δ [delta]=1.13 (t, 6H), 2.91 (m, 2H), 3.08 (m, 2H), 7.67 (dd, 1H), 7.77 (s, 2H), 7.89 (s, 1H), 8.22 (d, 1H), 8.51 (d, 1H), 10.73 (s, 1H).

Example 1c

Synthesis of 2-(3-chloro-2-pyridyl)-N-[2,4-dichloro-6-[(diethyl-$\lambda^4$-sulfanylidene)carbamoyl]phenyl]-5-(trifluoromethyl)pyrazole-3-carboxamide To a suspension of potassium carbonate (7.06 g, 50 mmol, 1.50 equiv.) and 2-amino-3,5-dichloro-N-(diethyl-$\lambda^4$-sulfanylidene)benzamide (9.98 g, 34.05 mmol) in dichloromethane (50 mL) was added a solution of 2-(3-chloro-2-pyridyl)-5-(trifluoromethyl)pyrazole-3-carbonyl chloride (13.8 g, 37.8 mmol, 1.10 equiv.) in dichloromethane (50 mL) at room temperature. After 3 h at this temperature, the solids were filtered off and water was added to the filtrate. The mixture was extracted with dichloromethane and dried over $Na_2SO_4$. After filtration, the filtrate was concentrated in vacuum and the resulting solids were crystallized from diethyl ether to yield the title compound (10.1 g, 52%).

Characterization by $^1$H-NMR (400 MHz, DMSO-$d_6$): δ [delta]=1.13 (t, 6H), 2.91 (m, 2H), 3.08 (m, 2H), 7.67 (dd, 1H), 7.77 (s, 2H), 7.89 (s, 1H), 8.22 (d, 1H), 8.51 (d, 1H), 10.73 (s, 1H).

Example 1d

Synthesis of 2-(3-chloro-2-pyridyl)-N-[2,4-dichloro-6-[(diethyl-$\lambda^4$-sulfanylidene)carbamoyl]phenyl]-5-(trifluoromethyl)pyrazole-3-carboxamide To a suspension of potassium carbonate (1.42 g, 10 mmol, 1.50 equiv.) and 2-amino-3,5-dichloro-N-(diethyl-$\lambda^4$-sulfanylidene)benzamide (2.00 g, 6.83 mmol) in dichloromethane (10 mL) was added a solution of 2-(3-chloro-2-pyridyl)-5-(trifluoromethyl)pyrazole-3-carbonyl chloride (2.77 g, 7.59 mmol, 1.10 equiv.) in dichloromethane (5 mL) at room temperature. After 2 h at this temperature, the solids were filtered off and water was added to the filtrate. The mixture was extracted with dichloromethane and dried over $Na_2SO_4$. After filtration, the filtrate was concentrated in vacuum and the resulting solids were crystallized from diethyl ether to yield the title compound (2.6 g, 67%).

Characterization by $^1$H-NMR (400 MHz, DMSO-$d_6$): δ [delta]=1.13 (t, 6H), 2.91 (m, 2H), 3.08 (m, 2H), 7.67 (dd, 1H), 7.77 (s, 2H), 7.89 (s, 1H), 8.22 (d, 1H), 8.51 (d, 1H), 10.73 (s, 1H).

Example 1e

Synthesis of 2-(3-chloro-2-pyridyl)-N-[2,4-dichloro-6-[(diethyl-$\lambda^4$-sulfanylidene)carbamoyl]phenyl]-5-(trifluoromethyl)pyrazole-3-carboxamide To a suspension of potassium carbonate (8.08 g, 58.5 mmol, 1.50 equiv.) and 2-amino-3,5-dichloro-N-(diethyl-$\lambda^4$-sulfanylidene)benzamide (11.43 g, 38.98 mmol) in acetonitrile (100 mL) was added a solution of 2-(3-chloro-2-pyridyl)-5-(trifluoromethyl)pyrazole-3-carbonyl chloride (15.8 g, 43.31 mmol, 1.10 equiv.) in acetonitrile (50 mL) at room temperature. After 6 h at this temperature, the solids were filtered off. The resulting filtrate was washed with water and dried over $Na_2SO_4$. After filtration, the filtrate was concentrated in vacuum and the resulting solids were crystallized from diisopropyl ether to yield the title compound (19.53 g, 88%).

Characterization by $^1$H-NMR (400 MHz, DMSO-$d_6$): δ [delta]=1.13 (t, 6H), 2.91 (m, 2H), 3.08 (m, 2H), 7.67 (dd, 1H), 7.77 (s, 2H), 7.89 (s, 1H), 8.22 (d, 1H), 8.51 (d, 1H), 10.73 (s, 1H).

Example 2a

Synthesis of 2-(3-chloro-2-pyridyl)-N-[2,4-dichloro-6-[(bis-2-propyl-$\lambda^4$-sulfanylidene)carbamoyl]phenyl]-5-(trifluoromethyl)pyrazole-3-carboxamide To a suspension of potassium carbonate (0.892 g, 6.46 mmol, 1.10 equiv.) and 2-amino-3,5-dichloro-N-(bis-2-propyl-$\lambda^4$-sulfanylidene)benzamide (2.05 g, 5.87 mmol) in toluene (30 mL) was added a solution of 2-(3-chloro-2-pyridyl)-5-(trifluoromethyl)-pyrazole-3-carbonyl chloride (2.02 g, 5.87 mmol, 1.00 equiv.) in toluene (20 mL) at 60° C. After 45 min at this temperature, the mixture was cooled and water was added.

The resulting precipitate was collected by filtration, washed with water and toluene and dried to obtain the title compound (3.07 g, 84%).

Characterization by UPLC-MS: 1.395 min, M=602.1

Example 2b

Synthesis of 2-(3-chloro-2-pyridyl)-N-[2,4-dichloro-6-[(bis-2-propyl-$\lambda^4$-sulfanylidene)carbamoyl]phenyl]-5-(trifluoromethyl)pyrazole-3-carboxamide To a solution of 6,8-dichloro-1H-3,1-benzoxazine-2,4-dione (2.50 g, 10.8 mmol) in anhydrous propylene carbonate (20 mL) was added bis-2-methylpropyl sulfinium sulfate (2.75 g, 7.53 mmol, 0.70 equiv.) and triethyl amine (1.14 g, 11.3 mmol, 1.10 equiv.) at room temperature. The mixture was stirred for 3 h. ⅓ of the resulting mixture was transferred to a separate reaction flask and used for the next transformation as such.

To a solution of the above obtained solution of 2-amino-3,5-dichloro-N-(bis-2-propyl-2$\lambda^4$-sulfanylidene)benzamide (6.7 mL; ~3.6 mmol) was added potassium carbonate (0.60 g, 4.3 mmol, 1.20 equiv.) and a solution of 2-(3-chloro-2-pyridyl)-5-(trifluoromethyl)pyrazole-3-carbonyl chloride (1.34 g, 4.31 mmol, 1.20 equiv.) in toluene (10 mL) at room temperature. After 6 h at this temperature, the mixture pured onto water and treated with a small amount of ethanol under sonification. The resulting precipitate was collected by filtration, washed with water and diisopropyl ether and dried to obtain the title compound (1.29 g, 60%).

Characterization by $^1$H-NMR (400 MHz, DMSO-$d_6$): δ [delta]=1.18 (d, 6H), 1.22 (d, 6H), 3.30 (m, 2H), 7.68 (dd, 1H), 7.75 (m, 2H), 7.81 (s, 1H), 8.21 (d, 1H), 8.54 (d, 1H), 10.76 (s, 1H).

Example 3a

Synthesis of 2-(3-chloro-2-pyridyl)-N-[2-methyl-4-chloro-6-[(bis-2-propyl-$\lambda^4$-sulfanylidene)carbamoyl]phenyl]-5-(trifluoromethyl)pyrazole-3-carboxamide To a suspension of potassium carbonate (1.79 g, 10 mmol, 1.30 equiv) and 2-amino-3-methyl-5-chloro-N-(bis-2-propyl-$\lambda^4$-sulfanylidene)benzamide (3.00 g, 9.97 mmol) in dichloromethane (20 mL) was added a solution of 2-(3-chloro-2-pyridyl)-5-(trifluoromethyl)pyrazole-3-carbonyl chloride (4.000 g, 10.97 mmol, 1.10 equiv.) in dichloromethane (10 mL) at room temperature. After 2 h at this temperature, the solids were filtered off. The resulting filtrate was washed with water and dried over $Na_2SO_4$. After filtration, the filtrate was concentrated in vacuum and the resulting solids were crystallized from diisopropyl ether to yield the title compound (3.1 g, 54%).

Characterization by UPLC-MS: 1.303 min, M=574.3

Example 3b

Synthesis of 2-(3-chloro-2-pyridyl)-N-[2-methyl-4-chloro-6-[(bis-2-propyl-$\lambda^4$-sulfanylidene)carbamoyl]phenyl]-5-(trifluoromethyl)pyrazole-3-carboxamide To a suspension of potassium carbonate (126.01 g, 911.76 mmol, 1.30 equiv.) and 2-amino-3-methyl-5-chloro-N-(bis-2-propyl-$\lambda^4$-sulfanylidene)benzamide (211 g, 701 mmol) in dichloromethane (300 mL) was added a solution of 2-(3-chloro-2-pyridyl)-5-(trifluoromethyl)pyrazole-3-carbonyl chloride (256.78 g, 771.49 mmol, 1.10 equiv.) in dichloromethane (200 mL) at room temperature. After 2 h at this temperature, the solids were filtered off. The resulting filtrate was washed with water and dried over $Na_2SO_4$. After filtration, the filtrate was concentrated in vacuum and the resulting solids were crystallized from diisopropyl ether to yield the title compound (344.2 g, 85%).

Characterization by UPLC-MS: 1.303 min, M=574.3

Example 4a

Synthesis of 2-(3-chloro-2-pyridyl)-N-[2-methyl-4-chloro-6-[(diethyl-$\lambda^4$-sulfanylidene)carbamoyl]phenyl]-5-(trifluoromethyl)pyrazole-3-carboxamide (Compound VIa-1-1)

To a suspension of potassium carbonate (0.71 g, 10 mmol, 1.3 equiv.) and 2-amino-3-methyl-5-chloro-N-(diethyl-2$\lambda^4$-sulfanylidene)benzamide (1.42 g, 3.96 mmol) in propylene carbonate (20 mL) was added a solution of 2-(3-chloro-2-pyridyl)-5-(trifluoromethyl)pyrazole-3-carbonyl chloride (1.35 g, 4.35 mmol, 1.10 equiv.) in propylene carbonate (10 mL) at room temperature. After 24 h at this temperature, the mixture was poured onto water and spiked with ethanol under vigorous stirring. The resulting solids were collected by filtration and contained pure title compound (1.57 g, 73%).

Characterization by HPLC-MS: LCMS (Method B): 1.19 min, m/z 546.1 (M+H)$^+$; m.p. 189° C.;

$^1$H NMR (500 MHz, DMSO) [delta]: 10.87 (s, 1H), 8.53 (d, 1H), 8.22 (d, 1H), 7.75 (s, 1H), 7.65 (m, 2H), 7.40 (s, 1H), 3.09 (m, 2H), 2.92 (m, 2H) 1.15 (m, 6H).

Example 4b 2-(3-chloro-2-pyridyl)-N-[2-methyl-4-chloro-6-[(diethyl-$\lambda^4$-sulfanylidene)carbamoyl]phenyl]-5-(trifluoromethyl)pyrazole-3-carboxamide To a solution of 2-(3-chloro-2-pyridyl)-5-(trifluoromethyl) pyrazole-3-carbonyl chloride (150 g, 435 mmol) in acetonitrile (900 mL) at room temperature was added potassium carbonate (59 g, 427 mmol). A solution of 2-amino-5-chloro-N-(diethyl-sulfanylidene)-3-methyl-benzamide (117 g, 427 mmol) in acetonitrile (100 mL) was added dropwise within 1 hour while maintaining a reaction temperature of 25-28° C. with occasional cooling (slightly exothermic reaction). The mixture was stirred for 16 hours at room temperature. The reaction mixture was then poured on ice-water mixture (5 L) and the pH was adjusted to 7-8 with concentrated HCl. The mixture stirred for an additional 2 hours. The light brown solid was filtered, washed with water and dried under air to give the crude product (229 g).

3 combined batches of crude product (789 g) were suspended in acetonitrile (2.6 L) and dissolved upon heating at 60° C. After 1 hour of stirring at 60° C. the solution was cooled by means of an ice-bath and the thereby formed solid was filtered off. The mother-liquor was concentrated to 300 mL and cooled with ice-bath. Thereby additional solid formed was filtered. The combined solids were washed with cold acetonitrile and dried at 50° C. in a vacuum-oven over night to give the title product (703 g, 89%) as a crystalline white solid.

Example 5

2-(3-chloro-2-pyridyl)-N-[2-methyl-4-chloro-6-[(di-2-propyl-λ⁴-sulfanylidene)carbamoyl]phenyl]-5-(trifluoromethyl)pyrazole-3-carboxamide (Compound VIa-1-2)

To a suspension of bis-2-isopropyl sulfinium sulfate (192 g, 0.53 mol, 0.68 equiv.) in DMSO (700 mL) a solution of 6-chloro-8-methyl-1H-3,1-benzoxazine-2,4-dione (162 g, 0.77 mol) in anhydrous DMSO (300 mL) was added at 22° C. followed by addition of triethylamine (117.4 mL, 84.75 g, 0.85 mol, 1.1 equiv.) at 22° C. The mixture was stirred for 6 h, and then added dropwise to ice-water. The mixture was extracted with dichloromethane and the combined organic layers were dried over sodium sulphate and concentrated in vacuo. The residue was triturated with diisopropyl ether to yield 2-amino-5-chloro-N-(diisopropyl-λ⁴-sulfanylidene)-3-methyl-benzamide (189.9 g, 82%).

Characterization by ¹H-NMR (400 MHz, CDCl₃): δ [delta] =1.40 (2×d, 12H), 2.11 (s, 3H), 3.23 (m, 2H), 6.05 (br. s, 2H), 7.03 (s, 1H), 8.01 (s, 1H).

HPLC: 0.908 min, m/z 301.3

To a suspension of potassium carbonate (9.73 g, 70.0 mmol, 1.10 equiv) and 2-amino-5-chloro-N-(diisopropyl-λ⁴-sulfanylidene)-3-methyl-benzamide (18.7 g, 62.4 mmol, 1.00 equiv) in toluene (80 mL) a solution of 2-(3-chloro-2-pyridyl)-5-(trifluoromethyl)pyrazole-3-carbonyl chloride (20.1 g, 64.1 mmol, 1.03 equiv.) in toluene (40 mL) was added at 60° C. After 35 minutes at 60° C., the reaction mixture was cooled to room temperature and diluted with EtOAc (50 mL) and water (50 mL). The organic phase was washed with water (50 mL), 0.1 M HCl (50 mL), dried over Na₂SO₄ and concentrated. The crude product was recrystallized from methyl tert-butyl ether to yield the title compound (24.4 g, 66%).

Characterization by ¹H-NMR (400 MHz, DMSO-d₆): δ [delta]=1.20 (d, 6H), 1.30 (d, 6H), 2.15 (s, 3H), 3.30 (m, 2H), 7.41 (s, 1H), 7.62 (m, 2H), 7.80 (s, 1H), 8.22 (d, 1H), 8.52 (d, 1H), 10.88 (s, 1H).

HPLC: 3.820 min, m/z 574.1

By the methods described in examples 1 to 5 the compounds of formula (VIa-1) or (VI-1) summarized in the following tables T.1 to T.5, were prepared.

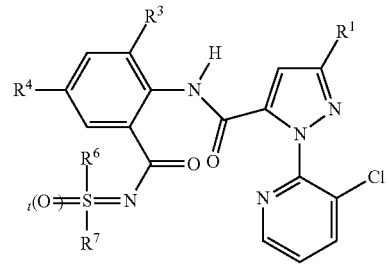

(VIa-1)

Compounds VIa-1 are compounds of the formula VI with $R^2$=Cl, $R^{3a}$=H, $R^{4a}$=H and $R^5$=H.

In tables T.1 to T.5 the following abbreviations are used:
H/M: HPLC/MS method
mp: melting point
$R^4$-1: CH(=N—OCH3)
$R^4$-2: 3-pyrazol-1H-yl
$R^4$-3: CH(=N—NHCH₂CF₃)
$R^4$-4: CH[=N—N(CH₃)₂]
$R^4$-5: CH(=N—OH)
$R^4$-6: 3-isoxazolyl
$R^4$-7: 2-chloro-5-thiophenyl
Me: Methyl
OMe: Methoxy
Et: Ethyl
i-Pr: isopropyl
i-Bu: isobutyl
3Me-2Bu: 3-methyl-2-butyl
3Me-1Bu: 3-methyl-1-butyl
n-Bu: n-butyl
2-Bu: 2-butyl
n-Pe: n-pentyl
n-Hex: n-hexyl
2-EtHex: 2-ethylhexyl
Et-OH: hydroxyethyl
Et-Cl: chloroethyl
OPropi: 1-propinoxy
c-Pr: cyclopropyl
c-Bu: cyclobutyl
c-Pe: cyclopentyl
Me-c-Pr: CH₂-cyclopropyl
Me-c-Bu: CH₂-cyclobutyl
Me-c-Pe: CH₂-cyclopentyl
Et-c-Pr: CH₂CH₂-cyclopropyl
iPr-c-Pr: CH(CH₃)-cyclopropyl
2Cl-5T: 2-chloro-5-thiophenyl
4-F-Ph: 4-fluorophenyl

TABLE T.1

Compounds of formula VIa-1

| Ex. | t | $R^6$ | $R^7$ | $R^3$ | $R^4$ | $R^1$ | H/M | RT [min] | m/z |
|---|---|---|---|---|---|---|---|---|---|
| 1 | 0 | Et | Et | Cl | Cl | CF₃ | A | 3.450 | 565.90 |
| 2 | 0 | i-Pr | i-Pr | Cl | Cl | CF₃ | A | 3.835 | 596.05 |
| 3 | 0 | Me—c-Pr | Me—c-Pr | Cl | Cl | CF₃ | B | 1.518 | 620.0 |
| 4 | 0 | i-Bu | i-Bu | Me | Cl | CF₃ | B | 1.395 | 602.1 |
| 5 | 0 | Et | Et | Me | NO₂ | CF₃ | B | 1.19 | 557 |
| 6 | 0 | CH₂—c-Pr | i-Pr | Me | Cl | CF₃ | B | 1.372 | 586.1 |
| 7 | 0 | Et | Et | Me | 2Cl-5T | CF₃ | A | 3.989 | 628.90 |
| 8 | 0 | Me—c-Pe | Et | Me | Cl | CF₃ | B | 1.372 | 600.3 |
| 9 | 0 | 3Me—2Bu | 3Me—2Bu | Cl | Cl | CF₃ | B | 1.488 | 652.1 |
| 10 | 0 | i-Bu | i-Bu | OMe | CN | CF₃ | A | 3.701 | 611 |
| 11 | 0 | Me | n-Pr | Me | Cl | CF₃ | logP: 3.2 [pH = 10.0] | | |

TABLE T.1-continued

Compounds of formula VIa-1

| Ex. | t | R⁶ | R⁷ | R³ | R⁴ | R¹ | H/M | RT [min] | m/z |
|---|---|---|---|---|---|---|---|---|---|
| 12 | 0 | Me—c-Pe | Me—c-Pe | Me | Cl | CF₃ | B | 1.500 | 654.3 |
| 13 | 0 | Et | Et | Me | F | CF₃ | B | 1.114 | 530 |
| 14 | 0 | Et | Me—c-Bu | Cl | Cl | CF₃ | B | 1.344 | 607.9 |
| 15 | 0 | 4-F—Ph | Me | Me | CN | CF₃ | colspan=3 | m.p: 72° C. | |
| 16 | 0 | colspan=2 | CH₂CH₂SCH₂ | Me | Cl | CF₃ | A | 3.631 | 561.95 |
| 17 | 0 | n-Hex | n-Hex | Me | Cl | CF₃ | B | 1.58 | 660.4 |
| 18 | 0 | Et—OH | Et—OH | Cl | Cl | CF₃ | B | 1.064 | 600 |
| 19 | 0 | n-Pr | n-Pr | Cl | Cl | CF₃ | A | 3.981 | 595.95 |
| 20 | 0 | Me—c-Pr | Et | Me | Cl | CF₃ | A | 3.714 | 571.95 |
| 21 | 1 | n-Pe | Et—OH | Me | Cl | CF₃ | | | |
| 22 | 0 | i-Pr | i-Pr | Br | CF₃ | CF₃ | B | 1.350 | 674.00 |
| 23 | 0 | 3Me—2Bu | 3Me—2Bu | Me | Cl | CF₃ | B | 1.473 | 630.3 |
| 24 | 0 | i-Pr | i-Pr | Me | Cl | CF₃ | colspan=3 | logP: 3.3 [pH = 10.0]; m.p: 142° C. | |
| 25 | 0 | Et—c-Pr | Et—c-Pr | Me | CN | CF₃ | B | 1.376 | 617.5 |
| 26 | 0 | i-Pr | i-Pr | Cl | CN | CF₃ | | 1.262 | 585.3 |
| 27 | 0 | i-Pr | i-Pr | Me | F | CF₃ | A | 3.400 | 558 |
| 28 | 0 | n-Pe | n-Pe | Me | CN | CF₃ | B | 1.443 | 621.5 |
| 29 | 0 | 3Me—1Bu | 3Me—1Bu | Me | Cl | CF₃ | B | 1.491 | 630.4 |
| 30 | 0 | i-Pr | c-Pr | Cl | Cl | CF₃ | B | 1.282 | 593.8 |
| 31 | 0 | Me | Me | Me | I | CF₃ | colspan=3 | logP: 3.2 [pH = 10.0]; m.p: 165° C. | |
| 32 | 0 | Me—c-Pr | i-Pr | Cl | CN | CF₃ | B | 1.271 | 597.1 |
| 33 | 0 | Et | Me | Me | I | CF₃ | colspan=3 | logP: 3.3 [pH = 10.0]; m.p: 181° C. | |
| 34 | 1 | Et | Et | Cl | Cl | CF₃ | B | 1.242 | 584.2 |
| 35 | 0 | Et | Et | Me | R⁴-5 | CF₃ | A | 2.94 | 555 |
| 36 | 0 | Me—c-Pe | Me—c-Pe | Cl | Cl | CF₃ | B | 1.514 | 676.2 |
| 37 | 0 | Et | c-Pr | Cl | Cl | CF₃ | B | 1.253 | 578.1 |
| 38 | 0 | i-Pr | i-Pr | Br | Cl | CF₃ | A | 3.630 | 639.90 |
| 39 | 0 | Me—c-Pe | Et | Me | CN | CF₃ | B | 1.310 | 591.4 |
| 40 | 0 | i-Pr | i-Pr | Br | Br | CF₃ | A | 3.665 | 683.90 |
| 41 | 0 | colspan=2 | CH₂CH₂CH₂CH₂ | Me | CN | CF₃ | colspan=3 | m.p: 194° C. | |
| 42 | 0 | Me—c-Bu | Et | Me | CN | CF₃ | B | 1.282 | 577.4 |
| 43 | 0 | Et | c-Pr | Me | Cl | CF₃ | B | 1.238 | 558.0 |
| 44 | 0 | Me—c-Bu | Me—c-Bu | Me | CN | CF₃ | B | 1.390 | 617.2 |
| 45 | 0 | Me | Me | c-Pr | Cl | CF₃ | A | 3.385 | 545 |
| 46 | 0 | Et—c-Pr | Et | Me | Cl | CF₃ | B | 1.311 | 586.4 |
| 47 | 0 | i-Pr | i-Pr | OMe | Cl | CF₃ | A | 3.343 | 592 |
| 48 | 0 | n-Pe | Et—OH | Me | Cl | CF₃ | colspan=3 | logP: 3.6 [pH = 10.0]; m.p: 133° C. | |
| 49 | 0 | Et | Et | Me | R⁴-1 | CF₃ | A | 3.205 | 570 |
| 50 | 0 | Et | i-Pr | Cl | Cl | CF₃ | B | 1.303 | 581.8 |
| 51 | 0 | 2-EtHex | 2-EtHex | Cl | Cl | CF₃ | B | 1.679 | 461.4 |
| 52 | 0 | i-Bu | i-Bu | Cl | Cl | CF₃ | B | 1.408 | 623.8 |
| 53 | 0 | Et | Et | Me | CN | CF₃ | B | 1.179 | 537.3 |
| 54 | 0 | Me—c-Pe | i-Pr | Me | Cl | CF₃ | B | 1.395 | 616 |
| 55 | 0 | Me—c-Pe | i-Pr | Cl | Cl | CF₃ | B | 1.401 | 636 |
| 56 | 0 | n-Hex | n-Hex | Me | CN | CF₃ | B | 1.534 | 649.2 |
| 57 | 0 | Et | Et—c-Pr | Me | CN | CF₃ | B | 1.264 | 577.4 |
| 58 | 0 | i-Pr | i-Pr | Cl | Br | CF₃ | A | 3.710 | 639.90 |
| 59 | 0 | Et | Et | Br | Cl | CF₃ | A | 3.633 | 611.85 |
| 60 | 0 | Et | Et | Me | R⁴-2 | CF₃ | A | 2.896 | 578.00 |
| 61 | 0 | Et | Et | c-Pr | Cl | CF₃ | A | 3.580 | 573 |
| 62 | 0 | Me—c-Pe | Et | Cl | Cl | CF₃ | B | 1.385 | 620.2 |
| 63 | 0 | Me—c-Pr | Me—c-Pr | Cl | CN | CF₃ | B | 1.287 | 609.1 |
| 64 | 0 | colspan=2 | CH₂CH₂CH₂CH₂ | Me | Cl | CF₃ | A | 3.481 | 544.05 |
| 65 | 0 | Me—c-Bu | i-Pr | Me | CN | CF₃ | B | 1.306 | 591.4 |
| 66 | 0 | Et | CH=CH₂ | Me | CN | CF₃ | colspan=3 | m.p: 60° C. | |
| 67 | 0 | n-Pe | n-Pe | Me | Cl | CF₃ | B | 1.492 | 630.4 |
| 68 | 0 | Et | Et | Me | Br | CF₃ | B | 1.225 | 592 |
| 69 | 0 | Me | Me | Me | CN | CF₃ | colspan=3 | m.p: 225° C. | |
| 70 | 0 | Et | Et | Br | Br | CF₃ | B | 1.218 | 655.9 |
| 71 | 0 | colspan=2 | CH₂CH₂CH₂CH₂CH₂ | Me | I | CF₃ | colspan=3 | logP: 3.6 [pH = 10.0]; m.p: 215° C. | |
| 72 | 0 | colspan=2 | CH₂CH₂CH₂CH₂CH₂ | Me | CN | CF₃ | colspan=3 | m.p: 85° C. | |
| 73 | 0 | Et | Et | Me | R⁴-6 | CF₃ | B | 1.094 | 581 |
| 74 | 0 | i-Pr | iPr—c-Pr | Me | Cl | CF₃ | B | 1.378 | 600.2 |
| 75 | 0 | i-Pr | i-Pr | Et | Cl | CF₃ | A | 3.785 | 589 |
| 76 | 0 | Et | Et | Et | Cl | CF₃ | A | 3.549 | 561 |
| 77 | 0 | i-Pr | c-Pr | Me | Cl | CF₃ | B | 1.257 | 572.1 |
| 78 | 0 | colspan=2 | CH₂CH₂CH₂CH₂ | Br | Cl | CF₃ | A | 3.537 | 609.85 |
| 79 | 0 | Et | Et | Br | CF₃ | CF₃ | B | 1.301 | 646.1 |
| 80 | 0 | i-Pr | i-Pr | Me | NO₂ | CF₃ | B | 1.274 | 585 |
| 81 | 0 | 3Me—2Bu | Et | Cl | Cl | CF₃ | B | 1.351 | 610 |

TABLE T.1-continued

Compounds of formula VIa-1

| Ex. | t | R⁶ | R⁷ | R³ | R⁴ | R¹ | H/M | RT [min] | m/z |
|---|---|---|---|---|---|---|---|---|---|
| 82 | 0 | Et—c-Pr | i-Pr | Me | CN | CF₃ | B | 1.313 | 591.3 |
| 83 | 0 | Et | Et | Me | Cl | CF₃ | B | 1.207 | 546.1 |
| 84 | 0 | i-Pr | i-Pr | Me | R⁴-6 | CF₃ | B | 1.155 | 609.0 |
| 85 | 0 | Et | Et | CF₃ | Br | CF₃ | B | 1.248 | 645.9 |
| 86 | 0 | Et—OH | n-Pe | Me | CN | CF₃ | | m.p: 47° C. | |
| 87 | 1 | Me | Me | Me | Cl | CF₃ | B | 1.191 | 534.0 |
| 88 | 0 | Et—c-Pr | Et | Cl | Cl | CF₃ | B | 1.319 | 608.2 |
| 89 | 0 | Me—c-Pr | Me—c-Pr | Me | Cl | CF₃ | A | 3.735 | 598.0 |
| 90 | 0 | Me | 4-F—Ph | Me | Cl | CF₃ | | m.p: 185° C. | |
| 91 | 0 | i-Pr | i-Pr | Cl | R⁴-5 | CF₃ | A | 3.238 | 603 |
| 92 | 0 | Me—c-Bu | i-Pr | Cl | Cl | CF₃ | B | 1.372 | 622.2 |
| 93 | 0 | Me | n-Pr | Me | I | CF₃ | | logP: 3.6 [pH = 10.0]; m.p: 85° C. | |
| 94 | 0 | i-Bu | i-Bu | c-Pr | Cl | CF₃ | A | 4.135 | 629 |
| 95 | 0 | 2-EtHex | 2-EtHex | Me | CN | CF₃ | B | 1.662 | 705.3 |
| 96 | 0 | Et | Et | Cl | Br | CF₃ | A | 3.704 | 611.85 |
| 97 | 0 | Et | Et | Me | R⁴-3 | CF₃ | A | 3.421 | 637 |
| 98 | 1 | Me | n-Pr | Me | I | CF₃ | | | |
| 99 | 0 | 2-Bu | Me | Me | Cl | CF₃ | | m.p: 88° C. | |
| 100 | 0 | CH₂CH₂SCH₂ | | Me | CN | CF₃ | | m.p: 88° C. | |
| 101 | 0 | Et—c-Pr | i-Pr | Me | Cl | CF₃ | B | 1.365 | 600.3 |
| 102 | 0 | Me | 4-F—Ph | Me | I | CF₃ | | m.p: 182° C. | |
| 103 | 0 | Et—c-Pr | Et—c-Pr | Cl | Cl | CF₃ | B | 1.427 | 648 |
| 104 | 0 | n-Pe | n-Pe | Cl | Cl | CF₃ | B | 1.508 | 652.1 |
| 105 | 0 | i-Pr | iPr—c-Pr | Cl | Cl | CF₃ | B | 1.263 | 553.9 |
| 106 | 0 | 3Me—1Bu | 3Me—1Bu | Me | CN | CF₃ | B | 1.443 | 621.6 |
| 107 | 0 | Et—c-Pr | Et—c-Pr | Me | Cl | CF₃ | B | 1.422 | 626.4 |
| 108 | 0 | i-Pr | i-Pr | Me | R⁴-5 | CF₃ | A | 3.087 | 583 |
| 109 | 0 | Me | Me | OMe | Cl | CF₃ | A | 2.911 | 535 |
| 110 | 0 | Me | Me | Me | Cl | CF₃ | | logP: 2.9 [pH = 10.0]; m.p: 182° C. | |
| 111 | 0 | 2-EtHex | 2-EtHex | Me | Cl | CF₃ | B | 1.604 | 680.5 |
| 112 | 0 | Et | Et | Cl | CN | CF₃ | B | 1.171 | 557.3 |
| 113 | 0 | n-Pe | Et—OH | Me | I | CF₃ | | logP: 3.9 [pH = 10.0]; m.p: 135° C. | |
| 114 | 0 | Me | Me | Et | Cl | CF₃ | A | 3.352 | 533 |
| 115 | 0 | Me—c-Bu | i-Pr | Me | Cl | CF₃ | B | 1.373 | 600.3 |
| 116 | 0 | Et—c-Pr | i-Pr | Cl | Cl | CF₃ | B | 1.374 | 622.2 |
| 117 | 0 | i-Bu | i-Bu | Et | Cl | CF₃ | A | 4.105 | 618 |
| 118 | 0 | n-Hex | n-Hex | Cl | Cl | CF₃ | B | 1.588 | 680.3 |
| 119 | 0 | n-Pr | n-Pr | Me | Cl | CF₃ | B | 1.318 | 574.0 |
| 120 | 0 | i-Pr | i-Pr | Me | I | CF₃ | | logP: 3.4 [pH = 10.0]; m.p: 75° C. | |
| 121 | 0 | Et—OH | Et—OH | Me | CN | CF₃ | B | 1.005 | 569.1 |
| 122 | 0 | 2-Bu | Me | Me | CN | CF₃ | | m.p: 66° C. | |
| 123 | 0 | Et—Cl | Et | Me | I | CF₃ | | m.p: 164° C. | |
| 124 | 0 | Me—c-Pr | Et | Cl | CN | CF₃ | B | 1.236 | 583.2 |
| 125 | 0 | i-Pr | i-Pr | CF₃ | Br | CF₃ | B | 1.308 | 673.9 |
| 126 | 1 | Et | Et | Me | Cl | CF₃ | B | 1.256 | 562.2 |
| 127 | 0 | Me—c-Bu | Me—c-Bu | Cl | Cl | CF₃ | B | 1.449 | 648.1 |
| 128 | 0 | CH₂CH₂SCH₂ | | Cl | Cl | CF₃ | A | 3.613 | 583.85 |
| 129 | 0 | CH₂CH₂SCH₂ | | Me | I | CF₃ | | logP: 3.5 [pH = 10.0]; m.p: 148° C. | |
| 130 | 0 | Me | Et | Me | CN | CF₃ | | m.p: 65° C. | |
| 131 | 0 | Et | Et | Cl | R⁴-5 | CF₃ | A | 3.061 | 575 |
| 132 | 0 | CH₂CH₂CH₂CH₂ | | Cl | Cl | CF₃ | A | 3.543 | 564.00 |
| 133 | 0 | Et | i-Pr | Me | Cl | CF₃ | B | 1.527 | 560.0 |
| 134 | 0 | i-Bu | i-Bu | OMe | Cl | CF₃ | A | 3.742 | 620 |
| 135 | 0 | Me | Me | OMe | CN | CF₃ | A | 2.805 | 526 |
| 136 | 0 | Me—c-Bu | Et | Me | Cl | CF₃ | B | 1.327 | 586.3 |
| 137 | 0 | CH₂CH₂CH₂CH₂ | | Me | I | CF₃ | | logP: 3.1 [pH = 10.0]; m.p: 185° C. | |
| 138 | 0 | Me—c-Pr | Et | Cl | Cl | CF₃ | A | 3.704 | 594.0 |
| 139 | 0 | i-Pr | i-Pr | Cl | CF₃ | CF₃ | B | 1.358 | 628.1 |
| 140 | 0 | Et—OH | Et—OH | Me | Cl | CF₃ | B | 1.065 | 578.3 |
| 141 | 0 | Me—c-Pe | Me—c-Pe | Me | CN | CF₃ | B | 1.459 | 645.4 |
| 142 | 0 | Et | Et | Cl | CF₃ | CF₃ | B | 1.284 | 600.1 |
| 143 | 0 | Et | Et | OMe | Cl | CF₃ | A | 3.117 | 563 |
| 144 | 0 | i-Pr | i-Pr | CF₃ | Cl | CF₃ | B | 1.169 | 628.1 |
| 145 | 0 | i-Pr | i-Pr | Me | Br | CF₃ | B | 1.300 | 620.0 |
| 146 | 0 | Et | Et | Me | R⁴-4 | CF₃ | A | 3.053 | 583 |
| 147 | 0 | Et | Et | CF₃ | Cl | CF₃ | B | 1.231 | 600.0 |
| 148 | 0 | i-Pr | i-Pr | Me | R⁴-7 | CF₃ | A | 4.181 | 666.00 |
| 149 | 0 | Et | 3Me—2Bu | Me | Cl | CF₃ | B | 1.342 | 588.1 |
| 150 | 0 | i-Pr | i-Pr | Me | CN | CF₃ | B | 1.253 | 565.3 |

TABLE T.1-continued

Compounds of formula VIa-1

| Ex. | t | R⁶ | R⁷ | R³ | R⁴ | R¹ | H/M | RT [min] | m/z |
|---|---|---|---|---|---|---|---|---|---|
| 151 | 0 | i-Pr | i-Pr | Me | Cl | CF₃ | B | 1.303 | 574.3 |
| 152 | 0 | Et | Me | Me | Cl | CF₃ | logP: 2.9 [pH = 10.0]; m.p: 181° C. | | |
| 153 | 0 | Me—c-Pe | i-Pr | Me | CN | CF₃ | B | 1.35 | 605.5 |
| 154 | 0 | Me—c-Pr | i-Pr | Cl | Cl | CF₃ | A | 3.993 | 607.95 |
| 155 | 0 | i-Pr | i-Pr | c-Pr | Cl | CF₃ | A | 3.787 | 601 |
| 156 | 0 | Me—c-Bu | Me—c-Bu | Me | Cl | CF₃ | B | 1.444 | 626.3 |
| 157 | 0 | i-Pr | 3Me—2Bu | Me | Cl | CF₃ | B | 1.364 | 602.3 |
| 158 | 0 | Me | Me | Cl | Cl | CF₃ | A | 3.372 | 539.95 |
| 159 | 0 | 3Me—1Bu | 3Me—1Bu | Cl | Cl | CF₃ | B | 1.489 | 652.1 |
| 160 | 0 | i-Pr | 3Me—2Bu | Cl | Cl | CF₃ | B | 1.409 | 623.9 |
| 161 | 0 | n-Pr | Me | Me | CN | CF₃ | m.p: 70° C. | | |
| 162 | 0 | Me | Me | OCHF₂ | Cl | CF₃ | A | 3.31 | 571 |

TABLE T.2

Compounds of formula VIa-1

| Ex. | t | R⁶ | R⁷ | R³ | R⁴ | R¹ | H/M | Rt [min] | m/z |
|---|---|---|---|---|---|---|---|---|---|
| 163 | 0 | Me—c-Pr | Me—c-Pr | Me | Cl | CHF₂ | A | 3.702 | 580.0 |
| 164 | 1 | Et | Et | Me | Cl | CHF₂ | A | 3.473 | 544 |
| 165 | 0 | Me—c-Pr | Me—c-Pr | Br | Cl | CHF₂ | B | 1.275 | 646.1 |
| 166 | 0 | Et | Et | Br | Br | CHF₂ | B | 1.171 | 638.1 |
| 167 | 0 | Me—c-Pr | Me—c-Pr | Cl | Cl | CHF₂ | B | 1.269 | 602.2 |
| 168 | 0 | i-Bu | i-Bu | Br | Cl | CHF₂ | B | 1.333 | 650.2 |
| 169 | 0 | Et | i-Pr | Cl | Cl | CHF₂ | B | 1.174 | 564.2 |
| 170 | 0 | i-Bu | i-Bu | Me | CN | CHF₂ | B | 1.254 | 575.4 |
| 171 | 0 | Et | Et | Br | Cl | CHF₂ | B | 1.148 | 594.1 |
| 172 | 0 | Me | Me | Me | CN | CHF₂ | B | 1.005 | 491.2 |
| 173 | 0 | Et | Et | Me | CN | CHF₂ | B | 3.035 | 519 |
| 174 | 0 | i-Pr | i-Pr | Me | Cl | CHF₂ | B | 1.225 | 556.3 |
| 175 | 0 | i-Bu | i-Bu | Cl | Cl | CHF₂ | B | 1.329 | 606.2 |
| 176 | 0 | Et | Et | Cl | Cl | CHF₂ | B | 1.144 | 549.9 |
| 177 | 0 | n-Pr | n-Pr | Me | Cl | CHF₂ | B | 3.639 | 556.1 |
| 178 | 0 | Me | Me | Br | Br | CHF₂ | B | 1.087 | 610.0 |
| 179 | 0 | i-Pr | i-Pr | Me | CN | CHF₂ | A | 3.277 | 547.1 |
| 180 | 0 | i-Pr | i-Pr | Br | Br | CHF₂ | B | 1.245 | 666.1 |
| 181 | 0 | Et | Et | Me | Cl | CHF₂ | B | 1.134 | 528.2 |
| 182 | 0 | i-Pr | i-Pr | Cl | Cl | CHF₂ | B | 1.24 | 578 |
| 183 | 0 | Me—c-Pr | Me—c-Pr | Br | Br | CHF₂ | B | 1.282 | 690.1 |
| 184 | 0 | i-Bu | i-Bu | Br | Br | CHF₂ | B | 1.346 | 694.2 |
| 185 | 0 | i-Pr | i-Pr | Br | Cl | CHF₂ | B | 1.205 | 622.2 |
| 186 | 0 | Me | Me | Cl | Cl | CHF₂ | B | 1.062 | 520.2 |
| 187 | 0 | i-Bu | i-Bu | Me | Cl | CHF₂ | B | 1.329 | 584.3 |
| 188 | 0 | Me | Me | Me | Cl | CHF₂ | B | 1.06 | 500.2 |
| 189 | 1 | Et | Et | Cl | Cl | CHF₂ | B | 1.163 | 566.1 |

TABLE T.3

Compounds of formula VIa-1

| Ex. | t | R⁶ | R⁷ | R³ | R⁴ | R¹ | H/M | Rt [min] | m/z |
|---|---|---|---|---|---|---|---|---|---|
| 190 | 0 | n-Pe | n-Pe | Me | CN | CN | B | 1.356 | 578.3 |
| 191 | 0 | Et | Et | Me | Cl | CN | B | 1.098 | 503.3 |
| 192 | 0 | Et | Et | Cl | Cl | CN | B | 1.119 | 524.9 |
| 193 | 0 | i-Pr | i-Pr | Me | Cl | CN | B | 1.19 | 531.3 |
| 194 | 0 | i-Pr | i-Pr | Cl | Cl | CN | B | 1.209 | 553.1 |

TABLE T.4

Compounds of formula VIa-1

| Ex. | t | R⁶ | R⁷ | R³ | R⁴ | R¹ | H/M | Rt [min] | m/z |
|---|---|---|---|---|---|---|---|---|---|
| 195 | 0 | Et—OH | n-Pe | Me | I | OPropi | logP: 3.5 [pH = 10.0] | | |
| 196 | 0 | i-Pr | i-Pr | Me | I | OPropi | logP: 3.1 [pH = 10.0] | | |
| 197 | 0 | i-Pr | i-Pr | Me | Cl | OPropi | logP: 2.7 [pH = 10.0] | | |
| 198 | 0 | Et | Et | Me | Cl | CHCl₂ | B | 1.194 | 562.2 |
| 199 | 0 | Me | Me | Me | H | CF₃ | logP: 2.2 [pH = 10.0]; m.p: 206° C. | | |
| 200 | 0 | CH₂CH₂SCH₂ | | Me | Cl | OPropi | logP: 2.5 [pH = 10.0] | | |
| 201 | 0 | Me | 4-F—Ph | Me | Cl | OPropi | logP: 2.9 [pH = 10.0] | | |
| 202 | 0 | i-Pr | i-Pr | Cl | Cl | OCH₃ | A | 3.284 | 557.90 |
| 203 | 0 | Et | Et | Me | Cl | OCH₃ | A | 2.953 | 508.05 |
| 204 | 0 | Me | 4-F—Ph | Me | I | OPropi | logP: 3.4 [pH = 10.0] | | |
| 205 | 0 | CH₂CH₂CH₂CH₂ | | Me | H | CF₃ | A | 2.994 | 510.05 |
| 206 | 0 | Et | CH₂CH₂Cl | Me | H | CF₃ | m.p: 171° C. | | |
| 207 | 0 | Et | Et | Me | Cl | NO₂ | B | 1.154 | 523.2 |
| 208 | 0 | CH₂CH₂SCH₂ | | Me | H | CF₃ | logP: 2.2 [pH = 10.0]; m.p: 188° C. | | |
| 209 | 0 | CH₂CH₂CH₂CH₂CH₂ | | Me | Cl | OPropi | logP: 2.8 [pH = 10.0] | | |
| 210 | 0 | Me | Et | Me | H | CF₃ | logP: 2.5 [pH = 10.0]; m.p: 181° C. | | |

TABLE T.4-continued

Compounds of formula VIa-1

| Ex. | t | $R^6$ | $R^7$ | $R^3$ | $R^4$ | $R^1$ | H/M | Rt [min] | m/z |
|---|---|---|---|---|---|---|---|---|---|
| 211 | 0 | n-Pr | Me | Me | H | $CF_3$ | | logP: 2.8 [pH = 10.0]; m.p: 143° C. | |
| 212 | 0 | Et | Et | Cl | Cl | $OCH_3$ | A | 3.096 | 529.95 |
| 213 | 0 | n-Pe | Et—OH | Me | H | $CF_3$ | | logP: 3.4 [pH = 10.0]; m.p: 106° C. | |
| 214 | 0 | i-Pr | i-Pr | Me | H | $CF_3$ | | logP: 2.7 [pH = 10.0]; m.p: 192° C. | |
| 215 | 0 | Me | 4-F—Ph | Me | H | $CF_3$ | | logP: 3.2 [pH = 10.0]; m.p: 180° C. | |
| 216 | 0 | Et—OH | n-Pe | Me | Cl | OPropi | | logP: 3.3 [pH = 10.0] | |

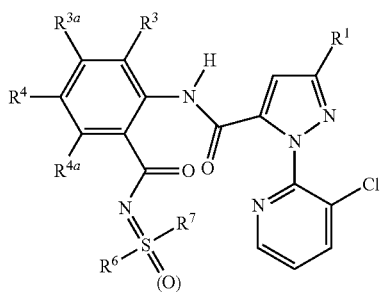

(VI-1)

Compounds VI-1 are compounds of the formula VI with $R^2$=Cl and $R^5$=H.

TABLE T.5

Compounds of formula VI-1

| Ex. | t | $R^6$ | $R^7$ | $R^3$ | $R^{3a}$ | $R^4$ | $R^{4a}$ | $R^1$ | H/M | RT [min] | m/z |
|---|---|---|---|---|---|---|---|---|---|---|---|
| 217 | 0 | Et | Et | Me | Cl | H | H | $CF_3$ | B | 1.208 | 546 |
| 218 | 0 | i-Pr | i-Pr | Me | Me | H | H | $CF_3$ | B | 1.13 | 554 |
| 219 | 0 | i-Pr | i-Pr | Me | Cl | H | H | $CF_3$ | B | 1.298 | 574 |
| 220 | 0 | i-Pr | i-Pr | Me | H | —CH=N—NH— | | OMe | B | 1.076 | 542.2 |
| 221 | 0 | $CH_2CH_2SCH_2$ | | H | H | —CH=N—NH— | | $CF_3$ | A | 3.570 | 554.9 |
| 222 | 0 | Et | Et | Me | H | H | Me | $CF_3$ | B | 1.004 | 526 |
| 223 | 0 | Et | Et | Me | H | —CH=N—NH— | | OMe | B | 0.992 | 514.3 |
| 224 | 0 | i-Pr | i-Pr | Me | H | H | Me | $CF_3$ | B | 1.056 | 554 |
| 225 | 0 | Et | Et | Me | Me | H | H | $CF_3$ | B | 1.073 | 526 |

The invention claimed is:

1. A process for preparing a compound of formula (I)

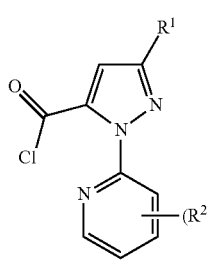

(I)

in which
$R^1$ is selected from the group consisting of hydrogen, halogen, cyano, —$SF_5$, $CBrF_2$, $C_1$-$C_6$-alkyl, $C_1$-$C_6$-fluoroalkyl, $C_3$-$C_8$-cycloalkyl, $C_3$-$C_8$-fluorocycloalkyl, $C_2$-$C_6$-alkenyl, $C_2$-$C_6$-fluoroalkenyl, wherein the six last mentioned radicals may be substituted by one or more radicals $R^a$; —$Si(R^f)_2R^g$, —$OR^b$, —$SR^b$, —$S(O)_mR^b$, —$S(O)_nN(R^c)R^d$,
—$N(R^{c1})R^{d1}$, phenyl which may be substituted by 1, 2, 3, 4 or 5 radicals $R^e$, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^e$;

each $R^2$ is independently selected from the group consisting of halogen, $SF_5$, $C_1$-$C_6$-alkyl, $C_1$-$C_6$-fluoroalkyl, $C_3$-$C_8$-cycloalkyl, $C_3$-$C_8$-fluorocycloalkyl, $C_2$-$C_6$-alkenyl, $C_2$-$C_6$-fluoroalkenyl, wherein the six last mentioned radicals may be substituted by one or more radicals $R^a$; —$Si(R^f)_2R^g$, —$OR^b$, —$SR^b$, —$S(O)_mR^b$, —$S(O)_nN(R^c)R^d$, —$N(R^{c1})R^{d1}$, phenyl which may be substituted by 1, 2, 3, 4 or 5 radicals $R^e$, and a 3-, 4-, 5-, 6- or 7-membered saturated, partially unsaturated or completely unsaturated heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^e$;

$R^a$ is selected from the group consisting of $SF_5$, $C_1$-$C_6$-alkyl, $C_1$-$C_6$-fluoroalkyl, $C_1$-$C_6$-alkoxy-$C_1$-$C_6$-alkyl, $C_3$-$C_8$-cycloalkyl, $C_3$-$C_8$-fluorocycloalkyl, $C_2$-$C_6$-alkenyl, $C_2$-$C_6$-fluoroalkenyl, —$Si(R^f)_2R^g$, —$OR^b$, —$S(O)_mR^b$,
—$S(O)_nN(R^c)R^d$, —$N(R^{c1})R^{d1}$, phenyl which may be substituted by 1, 2, 3, 4 or 5 radicals $R^e$, and a 3-, 4-, 5-, 6- or 7-membered saturated, partially unsaturated or completely unsaturated heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^e$;

or two geminally bound radicals $R^a$ together form a group selected from $=CR^hR^i$, $=NR^{c1}$, $=NOR^b$ and $=NNR^{c1}$, or two radicals $R^a$, together with the carbon atoms to which they are bound, form a 3-, 4-, 5-, 6-, 7- or 8-membered saturated or partially unsaturated carbocyclic or heterocyclic ring containing 1, 2 or 3 heteroatoms or heteroatom groups selected from the group consisting of N, O, S, NO, SO and $SO_2$, as ring members;

wherein, in the case of more than one $R^a$, $R^a$ can be identical or different;

$R^b$ is selected from the group consisting of $C_1$-$C_6$-alkyl, $C_1$-$C_6$-fluoroalkyl, $C_2$-$C_6$-alkenyl, $C_2$-$C_6$-fluoroalkenyl, $C_3$-$C_8$-cycloalkyl, $C_3$-$C_8$-fluorocycloalkyl, wherein the six last mentioned radicals may optionally carry 1 or 2 radicals selected from the group consisting of $C_1$-$C_6$-alkoxy, $C_1$-$C_6$-fluoroalkoxy, $C_1$-$C_6$-alkylthio, $C_1$-$C_6$-fluoroalkylthio, $C_1$-$C_6$-alkylsulfinyl, $C_1$-$C_6$-fluoroalkylsulfinyl, $C_1$-$C_6$-alkylsulfonyl, $C_1$-$C_6$-fluoroalkylsulfonyl, $-Si(R^f)_2R^g$, phenyl, benzyl, pyridyl and phenoxy, wherein the four last mentioned radicals may be unsubstituted, partially or fully halogenated and/or may carry 1, 2 or 3 substituents selected from the group consisting of $C_1$-$C_6$-alkyl, $C_1$-$C_6$-fluoroalkyl, $C_1$-$C_6$-alkoxy and $C_1$-$C_6$-fluoroalkoxy;

wherein, in the case of more than one $R^b$, $R^b$ can be identical or different;

$R^c$, $R^d$ are, independently from one another and independently of each occurrence, selected from the group consisting of cyano, $C_1$-$C_6$-alkyl, $C_1$-$C_6$-fluoroalkyl, $C_2$-$C_6$-alkenyl, $C_2$-$C_6$-fluoroalkenyl, $C_3$-$C_8$-cycloalkyl, $C_3$-$C_8$-fluorocycloalkyl, wherein the six last mentioned radicals may optionally carry 1 or 2 radicals selected from the group consisting of $C_1$-$C_6$-alkoxy, $C_1$-$C_6$-fluoroalkoxy, $C_1$-$C_6$-alkylthio, $C_1$-$C_6$-fluoroalkylthio, $C_1$-$C_6$-alkylsulfinyl, $C_1$-$C_6$-alkylsulfonyl, $-Si(R^f)_2R^g$, phenyl, benzyl, pyridyl and phenoxy, wherein the four last mentioned radicals may be unsubstituted, partially or fully halogenated and/or may carry 1, 2 or 3 substituents selected from the group consisting of $C_1$-$C_6$-alkyl, $C_1$-$C_6$-fluoroalkyl, $C_1$-$C_6$-alkoxy and $C_1$-$C_6$-fluoroalkoxy;

or $R^c$ and $R^d$, together with the nitrogen atom to which they are bound, form a 3-, 4-, 5-, 6- or 7-membered saturated, partly unsaturated or completely unsaturated heterocyclic ring which may contain 1 or 2 further heteroatoms selected from the group consisting of N, O and S as ring members, where the heterocyclic ring may carry 1, 2, 3 or 4 substituents selected from halogen, $C_1$-$C_4$-alkyl, $C_1$-$C_4$-fluoroalkyl, $C_1$-$C_4$-alkoxy and $C_1$-$C_4$-fluoroalkoxy;

$R^{c1}$ is hydrogen or has one of the meanings given for $R^c$;
$R^{d1}$ is hydrogen or has one of the meanings given for $R^d$;
$R^e$ is selected from the group consisting of halogen, $C_1$-$C_6$-alkyl, $C_1$-$C_6$-fluoroalkyl, $C_2$-$C_6$-alkenyl, $C_2$-$C_6$-fluoroalkenyl, $C_3$-$C_8$-cycloalkyl, $C_3$-$C_8$-fluorocycloalkyl, where the six last mentioned radicals may optionally carry 1 or 2 radicals selected from the group consisting of $C_1$-$C_4$-alkoxy; $C_1$-$C_6$-alkoxy, $C_1$-$C_6$-fluoroalkoxy, $C_1$-$C_6$-alkylthio, $C_1$-$C_6$-fluoroalkylthio, $C_1$-$C_6$-alkylsulfinyl, $C_1$-$C_6$-fluoroalkylsulfinyl, $C_1$-$C_6$-alkylsulfonyl, $C_1$-$C_6$-fluoroalkylsulfonyl, $-Si(R^f)_2R^g$, phenyl, benzyl, pyridyl and phenoxy, wherein the four last mentioned radicals may be unsubstituted, partially or fully halogenated and/or may carry 1, 2 or 3 substituents selected from the group consisting of $C_1$-$C_6$-alkyl, $C_1$-$C_6$-fluoroalkyl, $C_1$-$C_6$-alkoxy and $C_1$-$C_6$-fluoroalkoxy;

wherein, in the case of more than one $R^e$, $R^e$ can be identical or different;

$R^f$, $R^g$ are, independently of each other and independently of each occurrence, selected from the group consisting of $C_1$-$C_4$-alkyl, $C_3$-$C_6$-cycloalkyl, $C_1$-$C_4$-alkoxy-$C_1$-$C_4$-alkyl, phenyl and benzyl;

$R^h$, $R^i$ are, independently from one another and independently of each occurrence, selected from the group consisting of hydrogen, halogen, $SF_5$, $C_1$-$C_6$-alkyl, $C_1$-$C_6$-fluoroalkyl, $C_2$-$C_6$-alkenyl, $C_2$-$C_6$-fluoroalkenyl, $C_3$-$C_8$-cycloalkyl, $C_3$-$C_8$-fluorocycloalkyl, where the six last mentioned radicals may optionally carry 1 or 2 radicals selected from the group consisting of $C_1$-$C_4$-alkyl and $C_1$-$C_4$-fluoroalkyl; $C_1$-$C_6$-alkoxy, $C_1$-$C_6$-fluoroalkoxy, $C_1$-$C_6$-alkylthio, $C_1$-$C_6$-fluoroalkylthio, $C_1$-$C_6$-alkylsulfinyl, $C_1$-$C_6$-alkylsulfonyl, $-Si(R^f)_2R^g$, phenyl, benzyl, pyridyl and phenoxy, wherein the four last mentioned radicals may be unsubstituted, partially or fully halogenated and/or may carry 1, 2 or 3 substituents selected from the group consisting of $C_1$-$C_6$-alkyl, $C_1$-$C_6$-fluoroalkyl, $C_1$-$C_6$-alkoxy, $C_1$-$C_6$-fluoroalkoxy, ($C_1$-$C_6$-alkoxy)carbonyl, ($C_1$-$C_6$-alkyl)amino and di-($C_1$-$C_6$-alkyl)amino;

m is 1 or 2, wherein, in the case of several occurrences, m may be identical or different;

n is 0, 1 or 2; wherein, in the case of several occurrences, n may be identical or different;

r is 0, 1, 2, 3 or 4;

comprising
   i) deprotonating a compound of the formula (II)

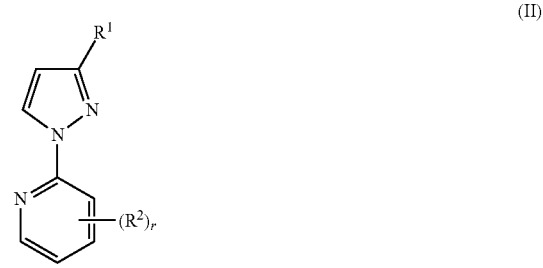

(II)

with a base selected from lithium-organic bases having a carbon or nitrogen bound lithium or with a magnesium-organic base having a carbon bound magnesium; and ii) subjecting the product obtained in step (i) to a chlorocarbonylation by reacting it with a reagent selected from the group consisting of phosgene or a phosgene equivalent which is trichloromethyl chloroformate, to obtain a compound of formula (I).

2. The process according to claim 1, wherein $R^1$ is selected from the group consisting of halogen, $C_1$-$C_4$-fluoroalkyl, $CBrF_2$, $C_1$-$C_4$-alkoxy and $C_1$-$C_4$-fluoroalkoxy-$C_1$-$C_4$-alkyl.

3. The process according to claim 1, wherein $R^1$ is selected from the group consisting of halogen, $CF_3$, $CHF_2$, $CBrF_2$ and methoxy.

4. The process according to claim 1, wherein
r is 1, and
R² is located in position 3 of the pyridyl moiety of the compound of the formula (I).

5. The process according to claim 4, wherein
r is 1, and
R² is selected from halogen and CF₃.

6. The process of claim 1, wherein the base is selected from the group consisting of alkyl magnesium halide and aryl magnesium halide.

7. The process of claim 1, wherein the base is selected from the group consisting of C₁-C₆-alkyl magnesium halide and C₅-C₆-cycloalkyl magnesium halide.

8. The process of claim 1, wherein the base is used in excess in relation to the compound of the formula (II).

9. The process claim 1, wherein the compound of formula II is obtained by reacting a compound of formula (III) with a compound of the formula (IV)

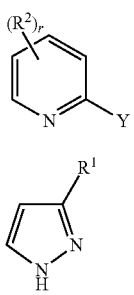

in which
Y is selected from the group consisting of halogen, C₁-C₃-alkoxy, C₁-C₃-alkylthio, C₃-C₃-haloalkoxy, C₁-C₃-haloalkylthio, —S(O)R$^b$, —S(O)₂R$^b$, —OS(O)R$^b$, —OS(O)₂R$^b$ and —NO₂;
in the presence of a base.

10. The process according to claim 9, wherein Y is chlorine.

11. The process according to claim 9, wherein the base is selected from the group consisting of alkali metal and alkaline earth metal carbonates.

12. The process according to claim 9, wherein the compound of formula (IV) is obtained by reacting a compound of formula (V)

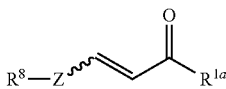

in which
R$^{1a}$a is selected from the group consisting of hydrogen, CBrF₂, C₁-C₆-alkyl, C₁-C₆-fluoroalkyl, C₃-C₈-cycloalkyl, C₃-C₈-fluorocycloalkyl, C₂-C₆-alkenyl, C₂-C₆-fluoroalkenyl, wherein the six last mentioned radicals may be substituted by one or more radicals R$^a$; —Si(R$^f$)₂R$^g$, —OR$^b$, —SR$^b$, —S(O)$_m$R$^b$, —S(O)$_n$N(R$^c$)R$^d$, —N(R$^{c1}$)R$^{d1}$, phenyl which may be substituted by 1, 2, 3, 4 or 5 radicals R$^e$, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and SO₂, as ring members, where the heterocyclic ring may be substituted by one or more radicals R$^e$;

R$^e$ is selected from the group consisting of halogen, C₁-C₆-alkyl, C₁-C₆-fluoroalkyl, C₂-C₆-alkenyl, C₂-C₆-fluoroalkenyl, C₃-C₈-cycloalkyl, C₃-C₈-fluorocycloalkyl, where the six last mentioned radicals may optionally carry 1 or 2 radicals selected from the group consisting of C₁-C₄-alkoxy; C₁-C₆-alkoxy, C₁-C₆-fluoroalkoxy, C₁-C₆-alkylthio, C₁-C₆-fluoroalkylthio, C₁-C₆-alkylsulfinyl, C₁-C₆-fluoroalkylsulfinyl, C₁-C₆-alkylsulfonyl, C₁-C₆-fluoroalkylsulfonyl, Si(R$^f$)₂R$^g$, phenyl, benzyl, pyridyl and phenoxy, wherein the four last mentioned radicals may be unsubstituted, partially or fully halogenated and/or may carry 1, 2 or 3 substituents selected from the group consisting of C₁-C₆-alkyl, C₁-C₆-fluoroalkyl, C₁-C₆-alkoxy and C₁-C₆-fluoroalkoxy;

Z is O or S; and
R⁸ is selected from the group consisting of C₁-C₆-alkyl, C₃-C₈-cycloalkyl, C₁-C₆-haloalkyl and C₁-C₆-cyclohaloalkyl;
with hydrazine, or its salts or its hydrates.

13. The process according to claim 12, wherein
Z is O; and
R⁸ is selected from the group consisting of methyl, ethyl, n-propyl, n-butyl and sec-butyl.

14. A process for preparing a compound of formula (VI)

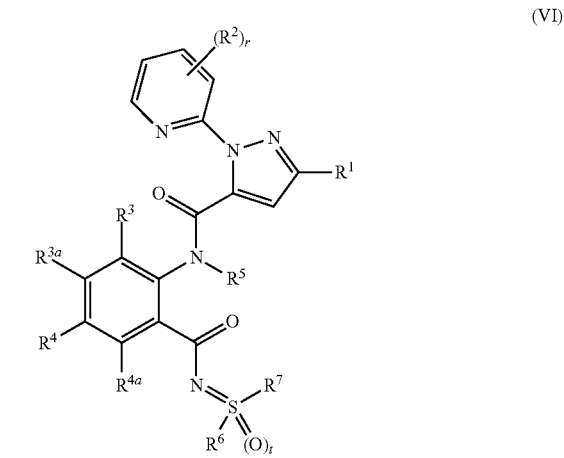

in which
R³ and R⁴ are independently selected from the group consisting of halogen, cyano, azido, nitro, —SCN, SF₅, C₁-C₆-alkyl, C₁-C₆-haloalkyl, C₃-C₈-cycloalkyl, C₃-C₈-halocycloalkyl, C₂-C₆-alkenyl, C₂-C₆-haloalkenyl, C₂-C₆-alkynyl, C₂-C₆-haloalkynyl, wherein the eight last mentioned radicals may be substituted by one or more radicals R$^a$; —Si(R$^f$)₂R$^g$, —OR$^{b1}$, —OS(O)$_n$R$^{b1}$, —SR$^{b1}$, —S(O)$_m$R$^{b1}$, —S(O)$_n$N(R$^{c1}$)R$^{d1}$, —N(R$^{c1}$)R$^{d1}$, —N(R$^{c1}$)C(=O)R$^a$, —C(=O)R$^a$, —C(=O)OR$^{b1}$, —C(=S)R$^a$, —C(=S)OR$^{b1}$, —C(=NR$^{c1}$)R$^a$, —C(=N—OR$^{b1}$)H, —C(=N—N(R$^{c1}$)R$^{d1}$)H, —C(=O)N(R$^{c1}$)R$^{d1}$, —C(=S)N(R$^{c1}$)R$^{d1}$, phenyl which may be substituted by 1, 2, 3, 4 or 5 radicals R$^e$, and a 3-, 4-, 5-, 6- or 7-membered saturated, partially unsaturated or completely unsaturated heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^e$;

or the radicals $R^4$ and $R^{4a}$ may be together a group selected from the group consisting of —$CH_2CH_2CH_2CH_2$—, —CH=CH—CH=CH—, —N=CH—CH=CH—, —CH=N—CH=CH—, —N=CH—N=CH—, —$OCH_2CH_2CH_2$—, —OCH=$CHCH_2$—, —$CH_2OCH_2CH_2$—, —$OCH_2CH_2O$—, —$OCH_2OCH_2$—, —$CH_2CH_2CH_2$—, —CH=$CHCH_2$—, —$CH_2CH_2O$—, —CH=CHO—, —$CH_2OCH_2$—, —$CH_2C(=O)O$—, —C(=O)$OCH_2$—, —O($CH_2$)O—, —$SCH_2CH_2CH_2$—, —SCH=$CHCH_2$—, —$CH_2SCH_2CH_2$—, —$SCH_2CH_2S$—, —$SCH_2SCH_2$—, —$CH_2CH_2S$—, —CH=CHS—, —$CH_2SCH_2$—, —$CH_2C(=S)S$—, —C(=S)$SCH_2$—, —S($CH_2$)S—, —$CH_2CH_2NR^j$—, —$CH_2CH=N$—, —CH=CH—$NR^j$—, —CH=N—$NR^j$—, —OCH=N— and —SCH=N—, thus forming, together with the carbon atoms to which they are bound, a 5- or 6-membered ring, where the hydrogen atoms of the above groups may be replaced by one or more substituents selected from halogen, methyl, halomethyl, hydroxyl, methoxy and halomethoxy or one or more $CH_2$ groups of the above groups may be replaced by a C=0 group;

$R^{3a}$ and $R^{4a}$ are independently selected from hydrogen and the meanings given for $R^3$ and $R^4$; or $R^{4a}$ may be together with the radical $R^4$ one of the groups defined above;

$R^5$ is selected from the group consisting of hydrogen, cyano, $C_1$-$C_{10}$-alkyl, $C_1$-$C_{10}$-haloalkyl, $C_3$-$C_8$-cycloalkyl, $C_3$-$C_8$-halocycloalkyl, $C_2$-$C_{10}$-alkenyl, $C_2$-$C_{10}$-haloalkenyl, $C_2$-$C_{10}$-alkynyl, $C_2$-$C_{10}$-haloalkynyl, wherein the eight last radicals may optionally be substituted by one or more radicals $R^a$; —N($R^{c1}$)$R^{d1}$, —Si($R^f$)$_2R^g$, —$OR^{b1}$, —$SR^{b1}$, —S(O)$_mR^{b1}$, —S(O)$_n$N($R^{c1}$)$R^{d1}$, —C(=O)$R^a$, —C(=O)$OR^{b1}$, —C(=O)N($R^{c1}$)$R^{d1}$, —C(=S)$R^a$, —C(=S)$OR^{b1}$, —C(=S)N($R^{c1}$)$R^{di}$, —C(=$NR^{c1}$)$R^a$, phenyl which may be substituted by 1, 2, 3, 4 or 5 radicals $R^e$, and a 3-, 4-, 5-, 6- or 7-membered saturated, partially unsaturated or completely unsaturated heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^e$;

$R^6$ and $R^7$ are selected independently of one another from the group consisting of hydrogen, $C_1$-$C_{10}$-alkyl, $C_1$-$C_{10}$-haloalkyl, $C_3$-$C_8$-cycloalkyl, $C_3$-$C_8$-halocycloalkyl, $C_2$-$C_{10}$-alkenyl, $C_2$-$C_{10}$-haloalkenyl, $C_2$-$C_{10}$-alkynyl, $C_2$-$C_{10}$-haloalkynyl, wherein the eight last radicals may optionally be substituted by one or more radicals $R^a$;

or $R^6$ and $R^7$ together represent a $C_2$-$C_7$-alkylene, $C_2$-$C_1$-alkenylene or $C_6$-$C_9$-alkynylene chain forming together with the sulfur atom to which they are attached a 3-, 4-, 5-, 6-, 7-, 8-, 9- or 10-membered saturated, partially unsaturated or completely unsaturated ring, wherein 1 to 4 of the $CH_2$ groups in the $C_2$-$C_7$-alkylene chain or 1 to 4 of any of the $CH_2$ or CH groups in the $C_2$-$C_7$-alkenylene chain or 1 to 4 of any of the $CH_2$ groups in the $C_6$-$C_9$-alkynylene chain may be replaced by 1 to 4 groups independently selected from the group consisting of C=O, C=S, O, S, N, NO, SO, $SO_2$ and NH, and wherein the carbon and/or nitrogen atoms in the $C_2$-$C_7$-alkylene, $C_2$-$C_7$-alkenylene or $C_6$-$C_9$-alkynylene chain may be substituted with 1 to 5 substituents independently selected from the group consisting of halogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl; said substituents being identical or different from one another if more than one substituent is present;

$R^{b1}$ is selected from the group consisting of hydrogen, $SF_5$, $C_1$-$C_6$-alkyl, $C_1$-$C_6$-fluoroalkyl, $C_1$-$C_6$-alkoxy-$C_1$-$C_6$-alkyl, $C_3$-$C_8$-cycloalkyl, $C_3$-$C_8$-fluorocycloalkyl, $C_2$-$C_6$-alkenyl, $C_2$-$C_6$-fluoroalkenyl, —Si($R^f$)$_2R^g$, —$OR^b$, —$SR^b$, —S(O)$_mR^b$, —S(O)$_n$N($R^c$)$R^d$, —N($R^{c1}$)$R^{d1}$, phenyl which may be substituted by 1, 2, 3, 4 or 5 radicals $R^e$, and a 3-, 4-, 5-, 6- or 7-membered saturated, partially unsaturated or completely unsaturated heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^e$;

or two geminally bound radicals $R^a$ together form a group selected from =$CR^hR^i$, =$NR^{c1}$, =$NOR^b$ and =$NNR^{c1}$, or two radicals $R^a$, together with the carbon atoms to which they are bound, form a 3-, 4-, 5-, 6-, 7- or 8-membered saturated or partially unsaturated carbocyclic or heterocyclic ring containing 1, 2 or 3 heteroatoms or heteroatom groups selected from the group consisting of N, O, S, NO, SO and $SO_2$, as ring members;

wherein, in the case of more than one $R^e$, $R^a$ can be identical or different;

$R^b$ is selected from the group consisting of $C_1$-$C_6$-alkyl, $C_1$-$C_6$-fluoroalkyl, $C_2$-$C_6$-alkenyl, $C_2$-$C_6$-fluoroalkenyl, $C_3$-$C_8$-cycloalkyl, $C_3$-$C_8$-fluorocycloalkyl, wherein the six last mentioned radicals may optionally carry 1 or 2 radicals selected from the group consisting of $C_1$-$C_6$-alkoxy, $C_1$-$C_6$-fluoroalkoxy, $C_1$-$C_6$-alkylthio, $C_1$-$C_6$-fluoroalkylthio, $C_1$-$C_6$-alkylsulfinyl, $C_1$-$C_6$-fluoroalkylsulfinyl, $C_1$-$C_6$-alkylsulfonyl, $C_1$-$C_6$-fluoroalkylsulfonyl, —Si($R^f$)$_2R^g$, phenyl, benzyl, pyridyl and phenoxy, wherein the four last mentioned radicals may be unsubstituted, partially or fully halogenated and/or may carry 1, 2 or 3 substituents selected from the group consisting of $C_1$-$C_6$-alkyl, $C_1$-$C_6$-fluoroalkyl, $C_1$-$C_6$-alkoxy and $C_1$-$C_6$-fluoroalkoxy;

wherein, in the case of more than one $R^b$, $R^b$ can be identical or different;

$R^c$, $R^d$ are, independently from one another and independently of each occurrence, selected from the group consisting of cyano, $C_1$-$C_6$-alkyl, $C_1$-$C_6$-fluoroalkyl, $C_2$-$C_6$-alkenyl, $C_2$-$C_6$-fluoroalkenyl, $C_3$-$C_8$-cycloalkyl, $C_3$-$C_8$-fluorocycloalkyl, wherein the six last mentioned radicals may optionally carry 1 or 2 radicals selected from the group consisting of $C_1$-$C_6$-alkoxy, $C_1$-$C_6$-fluoroalkoxy, $C_1$-$C_6$-alkylthio, $C_1$-$C_6$-fluoroalkylthio, $C_1$-$C_6$-alkylsulfinyl, $C_1$-$C_6$-alkylsulfonyl, —Si($R^f$)$_2R^g$, phenyl, benzyl, pyridyl and phenoxy, wherein the four last mentioned radicals may be unsubstituted, partially or fully halogenated and/or may carry 1, 2 or 3 substituents selected from the group consisting of $C_1$-$C_6$-alkyl, $C_1$-$C_6$-fluoroalkyl, $C_1$-$C_6$-alkoxy and $C_1$-$C_6$-fluoroalkoxy;

or $R^c$ and $R^d$, together with the nitrogen atom to which they are bound, form a 3-, 4-, 5-, 6- or 7-membered saturated, partly unsaturated or completely unsaturated heterocyclic ring which may contain 1 or 2 further heteroatoms selected from the group consisting of N, O and S as ring members, where the heterocyclic ring may carry 1, 2, 3 or 4 substituents selected from halogen, $C_1$-$C_4$-alkyl, $C_1$-$C_4$-fluoroalkyl, $C_1$-$C_4$-alkoxy and $C_1$-$C_4$-fluoroalkoxy;

$R^{c1}$ is hydrogen or has one of the meanings given for $R^c$;
$R^{d1}$ is hydrogen or has one of the meanings given for $R^d$;
$R^e$ is selected from the group consisting of halogen, $C_1$-$C_6$-alkyl, $C_1$-$C_6$-fluoroalkyl, $C_2$-$C_6$-alkenyl, $C_2$-$C_6$-fluoroalkenyl, $C_3$-$C_8$-cycloalkyl, $C_3$-$C_8$-fluorocycloalkyl, where the six last mentioned radicals may optionally carry 1 or 2 radicals selected from the group consisting of $C_1$-$C_4$-alkoxy; $C_1$-$C_6$-alkoxy, $C_1$-$C_6$-fluoroalkoxy, $C_1$-$C_6$-alkylthio, $C_1$-$C_6$-fluoroalkylthio, $C_1$-$C_6$-alkylsulfinyl, $C_1$-$C_6$-fluoroalkylsulfinyl, $C_1$-$C_6$-alkylsulfonyl, $C_1$-$C_6$-fluoroalkylsulfonyl, —Si($R^f$)$_2$$R^g$, phenyl, benzyl, pyridyl and phenoxy, wherein the four last mentioned radicals may be unsubstituted, partially or fully halogenated and/or may carry 1, 2 or 3 substituents selected from the group consisting of $C_1$-$C_6$-alkyl, $C_1$-$C_6$-fluoroalkyl, $C_1$-$C_6$-alkoxy and $C_1$-$C_6$-fluoroalkoxy;

wherein, in the case of more than one $R^e$, $R^e$ can be identical or different;

$R^f$, $R^g$ are, independently of each other and independently of each occurrence, selected from the group consisting of $C_1$-$C_4$-alkyl, $C_3$-$C_6$-cycloalkyl, $C_1$-$C_4$-alkoxy-$C_1$-$C_4$-alkyl, phenyl and benzyl;

m is 1 or 2, wherein, in the case of several occurrences, m may be identical or different;

n is 0, 1 or 2; wherein, in the case of several occurrences, n may be identical or different;

$R^j$ is selected from the group consisting of hydrogen, cyano, $C_1$-$C_6$-alkyl, $C_1$-$C_6$-haloalkyl, $C_1$-$C_6$-alkoxy, $C_1$-$C_6$-haloalkoxy, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl and $C_3$-$C_8$-cycloalkyl-$C_1$-$C_4$-alkyl; and t is 0 or 1;
which comprises providing a compound of the formula (I), as defined in claim 1, subsequently
iii) reacting the compound of the formula (I) with a compound of the formula (VII)

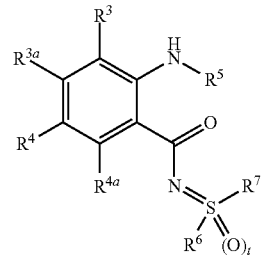

(VII)

in the presence of a base, to obtain a compound of the formula VI.

15. The process according to claim 14, wherein $R^{3a}$ and $R^{4a}$ are both hydrogen and $R^3$ and $R^4$ are independently selected from the group consisting of halogen, cyano, $C_1$-$C_4$-alkyl and $C_1$-$C_4$-haloalkyl.

16. The process according to claim 14, wherein
$R^3$ is selected from the group consisting of halogen, methyl and halomethyl, and
$R^4$ is selected from the group consisting of halogen, cyano, methyl and halomethyl.

17. The process of claim 14, wherein
t is 0, and
$R^6$ and $R^7$ are selected independently of one another from $C_1$-$C_6$-alkyl, or $R^6$ and $R^7$ together represent a $C_3$-$C_0$-alkylene chain forming together with the sulfur atom to which they are attached a 4-, 5-, 6- or 7-membered saturated ring.

* * * * *